United States Patent
McCullough

(10) Patent No.: US 9,266,977 B2
(45) Date of Patent: Feb. 23, 2016

(54) BRIDGED METALLOCENE COMPOUNDS, CATALYST SYSTEMS AND PROCESSES FOR POLYMERIZATION THEREWITH

(71) Applicant: ExxonMobil Chemical Patents Inc., Baytown, TX (US)

(72) Inventor: Laughlin G. McCullough, League City, TX (US)

(73) Assignee: ExxonMobil Chemical Patents Inc., Baytown, TX (US)

( * ) Notice: Subject to any disclaimer, the term of this patent is extended or adjusted under 35 U.S.C. 154(b) by 15 days.

(21) Appl. No.: 14/090,585

(22) Filed: Nov. 26, 2013

(65) Prior Publication Data
US 2014/0179884 A1  Jun. 26, 2014

Related U.S. Application Data

(60) Provisional application No. 61/740,938, filed on Dec. 21, 2012.

(51) Int. Cl.
| | |
|---|---|
| C07F 17/00 | (2006.01) |
| C08F 4/6592 | (2006.01) |
| C08F 10/00 | (2006.01) |
| C08F 4/659 | (2006.01) |

(52) U.S. Cl.
CPC ............ *C08F 4/65927* (2013.01); *C07F 17/00* (2013.01); *C08F 4/65916* (2013.01); *C08F 10/00* (2013.01)

(58) Field of Classification Search
CPC .. C07F 17/00; C08F 4/65927; C08F 4/65916; C08F 10/00
See application file for complete search history.

(56) References Cited

U.S. PATENT DOCUMENTS

2009/0137755 A1 *  5/2009  Yamada et al. ............... 526/112

FOREIGN PATENT DOCUMENTS

| JP | 2007-169341 | 7/2007 |
|---|---|---|
| JP | 2008-050278 | 3/2008 |
| JP | 2011-089019 | 5/2011 |
| JP | 2011-137146 A | 7/2011 |

OTHER PUBLICATIONS

E. Villasenor et al., "Neutral Dimethylzirconocene Complexes as Initiators for the Ring-Opening Polymerization of [epsilon]-Caprolactone", EP Jounal of Inorganic Chemistry, Mar. 1, 2013, vol. 2013, No. 7, pp. 1184-1196.
S. Yoon et al., "Synthesis, structure, and catalytic properties of ansa-Zirconocenes, Me2X (Cp)(Rind) ZrCl₂ (X=C, Si; R=2-p- or 3-p-tolyl)", Journal of Organometallic Chemistry, Apr. 28, 1997, vol. 534, No. 1-2, pp. 81-87.
V. Karttunen et al., "The influence of the ligand structure on activation of hafnocene polymerization catalysts: A theoretical study", Journal of Organometallic Chemistry, Nov. 26, 2007, vol. 693, No. 1, pp. 155-163.
U.S. Appl. No. 61/740,916, filed Dec. 21, 2012, Fiscus et al.

* cited by examiner

*Primary Examiner* — Caixia Lu
(74) *Attorney, Agent, or Firm* — Kevin M. Faulkner

(57) ABSTRACT

This invention relates to bridged metallocene compounds and catalyst systems comprising these bridged metallocene compounds.

38 Claims, No Drawings

BRIDGED METALLOCENE COMPOUNDS, CATALYST SYSTEMS AND PROCESSES FOR POLYMERIZATION THEREWITH

CROSS-REFERENCE TO RELATED APPLICATIONS

This application claims the benefit of Provisional Application No. 61/740,938, filed Dec. 21, 2012 and EP 13167620.7 filed May 14, 2013.

This application relates to U.S. Ser. No. 61/740,916, filed on Dec. 21, 2012.

FIELD OF THE INVENTION

This invention relates to bridged metallocene compounds useful for the polymerization of olefins, in particular ethylene. This invention also relates to polymerization processes using these bridged metallocene compounds, in particular, gas phase polymerization processes.

BACKGROUND OF THE INVENTION

Various types of polyethylenes are known in the art and each type has various applications. For example, low density polyethylene is generally prepared at high pressure using free radical initiators, or in gas phase processes using Ziegler-Natta or vanadium catalysts, and typically has a density in the range of 0.916 to 0.940 g/cm$^3$. This low density polyethylene, produced using free radical initiators, is known in the industry as "LDPE". LDPE is also known as "branched" or "heterogeneously branched" polyethylene because of the relatively large number of long chain branches extending from the main polymer backbone. Polyethylene in the same density range, i.e., 0.916 to 0.940 g/cm$^3$, which is linear and does not contain long chain branching is also known; this "linear low density polyethylene" ("LLDPE") may be produced with conventional Ziegler-Natta catalysts or with metallocene catalysts. Polyethylenes having still greater density are the high density polyethylenes ("HDPEs"), i.e., polyethylenes having densities greater than 0.940 g/cm$^3$, and are generally prepared with Ziegler-Natta catalysts. Very low density polyethylenes ("VLDPEs") are also known. VLDPEs can be produced by a number of different processes yielding polyethylenes having a density less than 0.916 g/cm$^3$, typically 0.890 to 0.915 g/cm$^3$ or 0.900 to 0.915 g/cm$^3$.

About 67% of global LDPE demand includes film, carrying bag, and sack applications. Some examples of these applications include agricultural, multi-layer, and shrink films, as well as reinforcements for levees. LDPE, which is soft, ductile, and flexible, is additionally utilized for strong, elastic goods, such as screw caps, lids, and coatings. There remains a demand for LDPE in the global marketplace, and consequently there is a continued need for improvements that provide cost savings.

Some improvements include using a different catalyst system. For example, some work has been done to provide branched polymers having a density of 0.940 gcm$^{-3}$ or less using metallocene compounds. JP2011089019A discloses a bridged metallocene in combination with a cocatalyst (a modified clay mineral, an alkyl alumoxane, or an ionized ionic compound) and an organoaluminum compound for olefin polymerization which can produce a polyolefin which possesses long chain branching, with high activity.

JP2011137146 discloses a manufacturing method for an ethylenic polymer using a catalyst for polymerization composed essentially of a component (A): a metallocene compound represented by a specified formula; a component (B): a compound to react with the metallocene component (A) to form cationic metallocenes; and a component (C): a fine particle carrier to give ethylene polymers characterized by (i) the existence of inflection points due to strain hardening in double-logarithmic plots of elongational viscosity [η(t); Pa·s; measured at 170° and elongational strain rate [λmax; defined as ηmax(t1)/ηlinear(t1); ηmax(t1)=maximum elongational viscosity after strain hardening; ηlinear(t1)=approximate line of elongational viscosity before hardening]≥2.0. Silica, dimethylsilylene(cyclopentadienyl)(indenyl)zirconium dichloride and methyl alumoxane were reacted to give a solid catalyst, which was used for polymerization of ethylene and 1-hexene in the presence of trimethylaluminum to give a copolymer showing λmax of 17.1.

Accordingly, there is a need for new processes to produce branched polymers having a density of 0.940 g/cm$^3$ or less. More specifically, there is a need for new catalyst systems, particularly metallocene catalyst systems to produce branched polymers having a density of 0.940 g/cm$^3$ or less. It is further desirable that these new metallocene catalyst systems are robust and have high productivity, particularly in gas phase polymerization processes.

SUMMARY OF THE INVENTION

This invention relates to a bridged metallocene compound represented by the following formula:

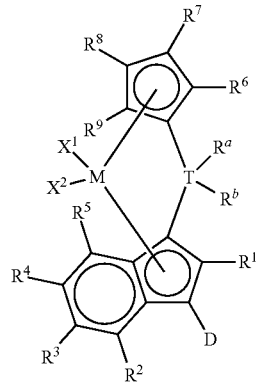

wherein:
M is a group 4 metal;
T is a group 14 atom;
D is a substituted or unsubstituted aromatic group;
$R^a$ and $R^b$ are independently, hydrogen, halogen, or a $C_1$ to $C_{20}$ substituted or unsubstituted hydrocarbyl, and $R^a$ and $R^b$ can form a cyclic structure including substituted or unsubstituted aromatic, partially saturated, or saturated cyclic or fused ring system;
each $X^1$ and $X^2$ is independently selected from the group consisting of $C_1$ to $C_{20}$ substituted or unsubstituted hydrocarbyl groups, hydrides, amides, amines, alkoxides, sulfides, phosphides, halides, dienes, phosphines, and ethers, and $X^1$ and $X^2$ can form a cyclic structure including aromatic, partially saturated, or saturated cyclic or fused ring system;
each of $R^1$, $R^2$, $R^3$, $R^4$, and $R^5$ is, independently, hydrogen, halide, alkoxide or a $C_1$ to $C_{40}$ substituted or unsubstituted hydrocarbyl group, and any of adjacent $R^2$, $R^3$, $R^4$, and/or $R^5$ groups may form a fused ring or multicenter fused ring systems, where the rings may be substituted or unsubstituted, and may be aromatic, partially unsaturated, or unsaturated; and each of $R^6$, $R^7$, $R^8$, and $R^9$ is, each independently, hydrogen or a $C_1$ to $C_{40}$ substituted or unsubstituted hydrocarbyl group; further provided that at least two of $R^6$, $R^7$, $R^8$, and $R^9$ are $C_1$ to $C_{40}$ substituted or unsubstituted hydrocarbyl groups.

This invention also relates to a catalyst system comprising: (i) a bridged metallocene compound represented by the following formula:

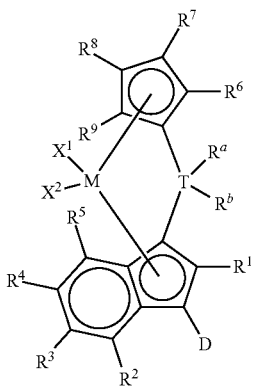

wherein:
M is a group 4 metal;
T is a group 14 atom;
D is a substituted or unsubstituted aromatic group;
$R^a$ and $R^b$ are independently, hydrogen, halogen, or a $C_1$ to $C_{20}$ substituted or unsubstituted hydrocarbyl, and $R^a$ and $R^b$ can form a cyclic structure including substituted or unsubstituted aromatic, partially saturated, or saturated cyclic or fused ring system;
each $X^1$ and $X^2$ is independently selected from the group consisting of $C_1$ to $C_{20}$ substituted or unsubstituted hydrocarbyl groups, hydrides, amides, amines, alkoxides, sulfides, phosphides, halides, dienes, phosphines, and ethers, and $X^1$ and $X^2$ can form a cyclic structure including aromatic, partially saturated, or saturated cyclic or fused ring system;
each of $R^1$, $R^2$, $R^3$, $R^4$, and $R^5$ is, independently, hydrogen, halide, alkoxide or a $C_1$ to $C_{40}$ substituted or unsubstituted hydrocarbyl group, and any of adjacent $R^2$, $R^3$, $R^4$, and/or $R^5$ groups may form a fused ring or multicenter fused ring systems, where the rings may be substituted or unsubstituted, and may be aromatic, partially unsaturated, or unsaturated; and
each of $R^6$, $R^7$, $R^8$, and $R^9$ is, each independently, hydrogen or a $C_1$ to $C_{40}$ substituted or unsubstituted hydrocarbyl group; further provided that at least two of $R^6$, $R^7$, $R^8$, and $R^9$ are $C_1$ to $C_{40}$ substituted or unsubstituted hydrocarbyl groups; and
(ii) at least one activator.

DETAILED DESCRIPTION

LDPE is typically produced in a tubular reactor system using a free radical initiator under conditions of very high pressure and temperature. The inventors have surprisingly found a metallocene compound and a catalyst system comprising said metallocene compound that produce branched low density polyethylene under less extreme conditions. Advantageously, this branched low density polyethylene may be produced in gas phase polymerization processes. The ability to produce branched low density polyethylene using gas phase polymerization systems is particularly advantageous because the production rate can be much greater than that achievable in tubular reactors, at lower pressures and temperatures. This increased productivity coupled with being able to run at reduced temperatures and pressures provides a significant cost advantage for branched low density polyethylene produced by metallocenes in the gas phase over traditional LDPEs. The metallocene compound and catalyst system are disclosed herein. Branched low density polyethylene and processes to make them are disclosed in U.S. Ser. No. 61/740,916, filed on Dec. 21, 2012.

DEFINITIONS

For the purposes of this invention and the claims thereto, the new numbering scheme for the Periodic Table Groups is used as set out in CHEMICAL AND ENGINEERING NEWS, 63(5), 27 (1985). Therefore, a "Group 4 metal" is an element from Group 4 of the Periodic Table.

"Catalyst productivity" is a measure of how many grams of polymer (P) are produced using a polymerization catalyst comprising W g of catalyst (cat), over a period of time of T hours; and may be expressed by the following formula: P/(T×W) and expressed in units of gP/gcat/hr. "Catalyst activity" is a measure of how many grams of polymer of polymer are produced using a polymerization catalyst comprising W g of catalyst (cat) and may be expressed by the following formula: P/W and expressed in units of gP/g(cat), and is typically used for batch processes. Catalyst activity may be converted to catalyst productivity by taking into account the run time of the batch process: catalyst productivity=catalyst activity/T, where T is the run time in hours.

An "olefin," alternatively referred to as "alkene," is a linear, branched, or cyclic compound of carbon and hydrogen having at least one double bond. For the purposes of this invention and the claims thereto, when a polymer is referred to as "comprising an olefin," the olefin present in the polymer is the polymerized form of the olefin. For example, when a copolymer is said to have an "ethylene" content of 35 wt % to 55 wt %, it is understood that the mer unit in the copolymer is derived from ethylene in the polymerization reaction and said derived units are present at 35 wt % to 55 wt %, based upon the weight of the copolymer. A "polymer" has two or more of the same or different mer units. "Polymer," as used herein, includes oligomers (up to 100 mer units) and larger polymers (greater than 100 mer units).

A "homopolymer" is a polymer having mer units that are the same. A "copolymer" is a polymer having two or more mer units that are different from each other. A "terpolymer" is a polymer having three mer units that are different from each other. "Different," as used to refer to mer units, indicates that the mer units differ from each other by at least one atom or are different isomerically. Accordingly, the definition of copolymer, as used herein, includes terpolymers and the like.

As used herein, Mn is number average molecular weight (measured by Gel Permeation Chromatography, GPC), Mw is weight average molecular weight (measured by GPC), and Mz is z average molecular weight (measured by GPC), wt % is weight percent, mol % is mole percent, vol % is volume percent and mol is mole. Molecular weight distribution (MWD) is defined to be Mw (measured by GPC) divided by Mn (measured by GPC), Mw/Mn. Unless otherwise noted, all molecular weights (e.g., Mw, Mn, Mz) have units of g/mol.

A "catalyst system" is combination of at least one metallocene compound, at least one activator, an optional co-activator, and an optional support material. An "anionic ligand" is a negatively charged ligand which donates one or more pairs of electrons to a metal ion. A "neutral donor ligand" is a neutrally charged ligand which donates one or more pairs of electrons to a metal ion.

Metallocene Compounds

A metallocene compound is defined as an organometallic compound with at least one π-bound cyclopentadienyl moiety (or substituted cyclopentadienyl moiety) and more frequently two π-bound cyclopentadienyl-moieties or substituted moieties. This includes other π-bound moieties such as indenyls or fluorenyls or derivatives thereof. The inventors have surprisingly discovered new metallocene compounds described below. These metallocene compounds may be useful in the production of branched, low density polyethylene.

For the purposes of this invention and the claims thereto, when catalyst systems are described as comprising neutral stable forms of the components, it is well understood by one of ordinary skill in the art, that the ionic form of the component is the form that reacts with the monomers to produce polymers.

This invention relates to bridged metallocene compounds represented by the following formula:

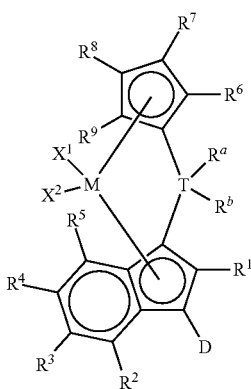

wherein:
M is a group 4 metal (preferably, M is zirconium or hafnium; more preferably, zirconium);
T is a group 14 atom (preferably, silicon or germanium; more preferably, silicon);
D is a substituted or unsubstituted aromatic group (preferably, D is selected from the group consisting of substituted or unsubstituted phenyl, naphthyl, biphenyl, cyclopropenyl, tropylium, cyclooctatetraenyl, furanyl, pyridinyl, borabenzyl, thiophenyl, azolyl, oxazolyl, and imidazolyl; more preferably, D is selected from the group consisting of substituted or unsubstituted phenyl, biphenyl, naphthyl, cyclopropenyl, furanyl, pyridinyl, thiophenyl, azolyl, oxazolyl, and imidazolyl, where "substituted or unsubstituted" refers to all members of the group listed);
$R^a$ and $R^b$ are independently, hydrogen, halogen, or a $C_1$ to $C_{20}$ substituted or unsubstituted hydrocarbyl, and $R^a$ and $R^b$ can form a cyclic structure including substituted or unsubstituted aromatic, partially saturated, or saturated cyclic or fused ring system (preferably, each $R^a$ and $R^b$ is independently selected from the group consisting of halides, $C_1$ to $C_{20}$ substituted or unsubstituted hydrocarbyl groups, and cyclic structures where $R^a$ and $R^b$ form a heterocyclopentyl, heterocyclobutyl, or heterocyclohexyl structure with T being the heteroatom; more preferably, each $R^a$ and $R^b$ is independently selected from the group consisting of chlorides, fluorides, methyl, and ethyl groups; more preferably, each $R^a$ and $R^b$ is, independently, selected from the group consisting of chlorides, fluorides, methyl, and ethyl groups);
each $X^1$ and $X^2$ is independently selected from the group consisting of $C_1$ to $C_{20}$ substituted or unsubstituted hydrocarbyl groups, hydrides, amides, amines, alkoxides, sulfides, phosphides, halides, dienes, phosphines, and ethers; and $X^1$ and $X^2$ can form a cyclic structure including aromatic, partially saturated, or saturated cyclic or fused ring system;
more preferably, each $X^1$ and $X^2$ is independently selected from the group consisting of chlorides, fluorides, methyl, and ethyl groups;
each of $R^1$, $R^2$, $R^3$, $R^4$, and $R^5$ is, independently, hydrogen, halide, alkoxide or a $C_1$ to $C_{40}$ substituted or unsubstituted hydrocarbyl group, and any of adjacent $R^2$, $R^3$, $R^4$, and/or $R^5$ groups may form a fused ring or multicenter fused ring systems, where the rings may be substituted or unsubstituted, and may be aromatic, partially unsaturated, or unsaturated (preferably, each of $R^1$, $R^2$, $R^3$, $R^4$, and $R^5$ is, independently, a $C_1$ to $C_{20}$ substituted or unsubstituted hydrocarbyl group); and
each of $R^6$, $R^7$, $R^8$, and $R^9$ is, each independently, hydrogen or a $C_1$ to $C_{40}$ substituted or unsubstituted hydrocarbyl group (preferably, each of $R^6$, $R^7$, $R^8$, and $R^9$ is, independently, a $C_1$ to $C_{40}$ substituted or unsubstituted hydrocarbyl group; more preferably, each of $R^6$, $R^7$, $R^8$, and $R^9$ is, independently, a $C_1$ to $C_{20}$ substituted or unsubstituted hydrocarbyl group;
more preferably, each of $R^6$, $R^7$, $R^8$, and $R^9$ is, independently, selected from the group consisting of methyl, ethyl, propyl, isopropyl, n-butyl, sec-butyl, t-butyl, pentyl, hexyl, heptyl, octyl, decyl, and undecyl groups; even more preferably, each of $R^6$, $R^7$, $R^8$, and $R^9$ is, independently, selected from the group consisting of methyl, ethyl, and n-propyl groups;
preferably adjacent $R^6$, $R^7$, $R^8$, and/or $R^9$ groups fuse together with the cyclopentadienyl group to form a substituted or unsubstituted fluorene);
further provided that at least two of $R^6$, $R^7$, $R^8$, and $R^9$ are $C_1$ to $C_{40}$ substituted or unsubstituted hydrocarbyl groups.

In preferred embodiments, the metallocene compound is asymmetric, which is defined to mean that the groups that are bridged by the $TR^aR^b$ bridge do not have the same number of fused aromatic rings, for example, the metallocene compound is not a bis-indenyl compound. Instead, the metallocene compound may be a cyclopentadienyl-indenyl compound, a cyclopentadienyl-fluorenyl compound, or a indenyl-fluorenyl compound, etc.

Preferred metallocene compounds may be represented by the following formula:

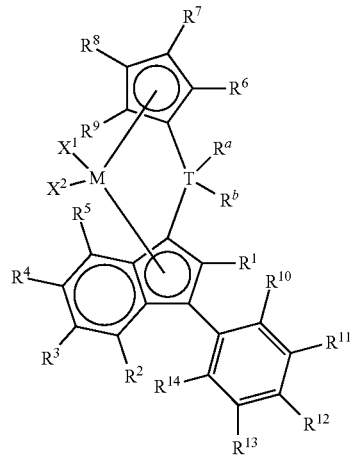

wherein $R^1$, $R^2$, $R^3$, $R^4$, $R^5$, $R^6$, $R^7$, $R^8$, $R^9$, $R^a$, $R^b$, $X^1$, $X^2$, T, and M are as defined above; and $R^{10}$, $R^{11}$, $R^{12}$, $R^{13}$, and $R^{14}$ are each independently H or a $C^1$ to $C^{40}$ substituted or unsubstituted hydrocarbyl.

Other preferred metallocene compounds useful herein may be represented by the formula:

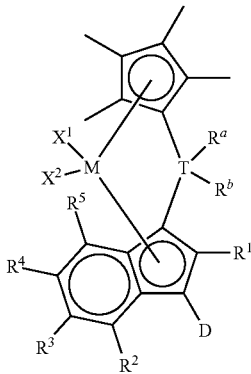

wherein $R^1$, $R^2$, $R^3$, $R^4$, $R^5$, $R^a$, $R^b$, $X^1$, $X^2$, T, D, and M are as defined above.

In particularly preferred embodiments, metallocene compounds useful herein may be represented by the following structure:

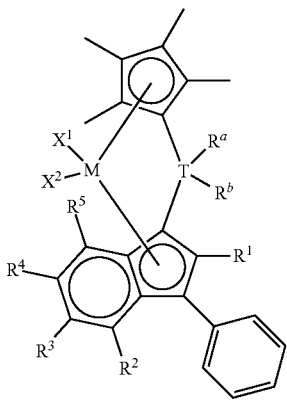

wherein $R^1$, $R^2$, $R^3$, $R^4$, $R^5$, $R^a$, $R^b$, $X^1$, $X^2$, T, and M are as defined above.

Examples of preferred metallocene compounds include:
dimethylsilylene(3-phenyl-1-indenyl)(2,3,4,5-tetramethyl-1-cyclopentadienyl)zirconium dichloride;
dimethylsilylene(3-phenyl-1-indenyl)(2,5-dimethyl-1-cyclopentadienyl)zirconium dichloride;
dimethylsilylene(3-phenyl-1-indenyl)(3,4-dimethyl-1-cyclopentadienyl)zirconium dichloride;
dimethylsilylene(3-phenyl-1-indenyl)(2,3,4,5-tetraethyl-1-cyclopentadienyl)zirconium dichloride;
dimethylsilylene(3-phenyl-1-indenyl)(2,3,4,5-tetrapropyl-1-cyclopentadienyl)zirconium dichloride;
dimethylsilylene(3-phenyl-1-indenyl)(9-fluorenyl)zirconium dichloride; dimethylsilylene(3-phenyl-1-indenyl)(2,7-dimethyl-9-fluorenyl)zirconium dichloride;
dimethylsilylene(3-phenyl-1-indenyl)(2,7-di-t-butyl-9-fluorenyl)zirconium dichloride;
dimethylsilylene(3-phenyl-1-indenyl)(3,6-dimethyl-9-fluorenyl)zirconium dichloride;
dimethylsilylene(3-phenyl-1-indenyl)(3,6-di-t-butyl-9-fluorenyl)zirconium dichloride;
dimethylsilylene(3-phenyl-1-indenyl)(4,7-dimethyl-9-fluorenyl)zirconium dichloride;
diethylsilylene(3-phenyl-1-indenyl)(2,3,4,5-tetramethyl-1-cyclopentadienyl)zirconium dichloride;
dipropylsilylene(3-phenyl-1-indenyl)(2,3,4,5-tetramethyl-1-cyclopentadienyl)zirconium dichloride;
dibutylsilylene(3-phenyl-1-indenyl)(2,3,4,5-tetramethyl-1-cyclopentadienyl)zirconium dichloride;
diphenylsilylene(3-phenyl-1-indenyl)(2,3,4,5-tetramethyl-1-cyclopentadienyl)zirconium dichloride;
silacyclobutylidene(3-phenyl-1-indenyl)(2,3,4,5-tetramethyl-1-cyclopentadienyl)zirconium dichloride;
silacyclopentylidene(3-phenyl-1-indenyl)(2,3,4,5-tetramethyl-1-cyclopentadienyl)zirconium dichloride;
silacyclohexylidene(3-phenyl-1-indenyl)(2,3,4,5-tetramethyl-1-cyclopentadienyl)zirconium dichloride;
dimethylgermylene(3-phenyl-1-indenyl)(2,3,4,5-tetramethyl-1-cyclopentadienyl)zirconium dichloride;
diethylgermylene(3-phenyl-1-indenyl)(2,3,4,5-tetramethyl-1-cyclopentadienyl)zirconium dichloride;
dipropylgermylene(3-phenyl-1-indenyl)(2,3,4,5-tetramethyl-1-cyclopentadienyl)zirconium dichloride;
dibutylgermylene(3-phenyl-1-indenyl)(2,3,4,5-tetramethyl-1-cyclopentadienyl)zirconium dichloride;
diphenylgermylene(3-phenyl-1-indenyl)(2,3,4,5-tetramethyl-1-cyclopentadienyl)zirconium dichloride;
isopropylidene(3-phenyl-1-indenyl)(2,3,4,5-tetramethyl-1-cyclopentadienyl)zirconium dichloride;
diphenylmethylene(3-phenyl-1-indenyl)(2,3,4,5-tetramethyl-1-cyclopentadienyl)zirconium dichloride;
dimethylsilylene(2-methyl-3-phenyl-1-indenyl)(2,3,4,5-tetramethyl-1-cyclopentadienyl)zirconium dichloride;
dimethylsilylene(2-ethyl-3-phenyl-1-indenyl)(2,3,4,5-tetramethyl-1-cyclopentadienyl)zirconium dichloride;
dimethylsilylene(2-propyl-3-phenyl-1-indenyl)(2,3,4,5-tetramethyl-1-cyclopentadienyl)zirconium dichloride;
dimethylsilylene(2-isopropyl-3-phenyl-1-indenyl)(2,3,4,5-tetramethyl-1-cyclopentadienyl)zirconium dichloride;
dimethylsilylene(4-methyl-3-phenyl-1-indenyl)(2,3,4,5-tetramethyl-1-cyclopentadienyl)zirconium dichloride;
dimethylsilylene(4,7-dimethyl-3-phenyl-1-indenyl)(2,3,4,5-tetramethyl-1-cyclopentadienyl)zirconium dichloride;
dimethylsilylene(5,6-dimethyl-3-phenyl-1-indenyl)(2,3,4,5-tetramethyl-1-cyclopentadienyl)zirconium dichloride;
dimethylsilylene(2,4-dimethyl-3-phenyl-1-indenyl)(2,3,4,5-tetramethyl-1-cyclopentadienyl)zirconium dichloride;
dimethylsilylene(2,6-dimethyl-3-phenyl-1-indenyl)(2,3,4,5-tetramethyl-1-cyclopentadienyl)zirconium dichloride;
dimethylsilylene(3-phenyl-2,4,6-trimethyl-1-indenyl)(2,3,4,5-tetramethyl-1-cyclopentadienyl)zirconium dichloride;
dimethylsilylene(3-phenyl-2,4,7-trimethyl-1-indenyl)(2,3,4,5-tetramethyl-1-cyclopentadienyl)zirconium dichloride;
dimethylsilylene(3-phenyl-2,5,6-trimethyl-1-indenyl)(2,3,4,5-tetramethyl-1-cyclopentadienyl)zirconium dichloride;
dimethylsilylene(3-phenyl-4,5,6,7-tetramethyl-1-indenyl)(2,3,4,5-tetramethyl-1-cyclopentadienyl)zirconium dichloride;
dimethylsilylene(2,4,5,6,7-pentamethyl-3-phenyl-1-indenyl)(2,3,4,5-tetramethyl-1-cyclopentadienyl)zirconium dichloride;
dimethylsilylene(6-chloro-3-phenyl-1-indenyl)(2,3,4,5-tetramethyl-1-cyclopentadienyl)zirconium dichloride;
dimethylsilylene(7-chloro-3-phenyl-1-indenyl)(2,3,4,5-tetramethyl-1-cyclopentadienyl)zirconium dichloride;
dimethylsilylene(4,6-dichloro-3-phenyl-1-indenyl)(2,3,4,5-tetramethyl-1-cyclopentadienyl)zirconium dichloride;

dimethylsilylene(5,7-dichloro-2-methyl-3-phenyl-1-indenyl)(2,3,4,5-tetramethyl-1-cyclopentadienyl)zirconium dichloride;
dimethylsilylene(2-butyl-7-chloro-3-phenyl-1-indenyl)(2,3,4,5-tetramethyl-1-cyclopentadienyl)zirconium dichloride;
dimethylsilylene(7-chloro-3-phenyl-2-propyl-1-indenyl)(2,3,4,5-tetramethyl-1-cyclopentadienyl)zirconium dichloride;
dimethylsilylene(7-chloro-2-ethyl-3-phenyl-1-indenyl)(2,3,4,5-tetramethyl-1-cyclopentadienyl)zirconium dichloride;
dimethylsilylene(5-fluoro-3-phenyl-1-indenyl)(2,3,4,5-tetramethyl-1-cyclopentadienyl)zirconium dichloride;
dimethylsilylene(5,7-difluoro-3-phenyl-1-indenyl)(2,3,4,5-tetramethyl-1-cyclopentadienyl)zirconium dichloride;
dimethylsilylene(4,6-difluoro-3-phenyl-1-indenyl)(2,3,4,5-tetramethyl-1-cyclopentadienyl)zirconium dichloride;
dimethylsilylene(5,7-difluoro-2-methyl-3-phenyl-1-indenyl)(2,3,4,5-tetramethyl-1-cyclopentadienyl)zirconium dichloride;
dimethylsilylene(3-phenyl-1,5,6,7-tetrahydro-s-1-indacenyl)(2,3,4,5-tetramethyl-1-cyclopentadienyl)zirconium dichloride;
dimethylsilylene(2-methyl-3-phenyl-1,5,6,7-tetrahydro-s-1-indacenyl)(2,3,4,5-tetramethyl-1-cyclopentadienyl)zirconium dichloride;
dimethylsilylene(6,6-dimethyl-3-phenyl-1,5,6,7-tetrahydro-s-1-indacenyl)(2,3,4,5-tetramethyl-1-cyclopentadienyl)zirconium dichloride;
dimethylsilylene(3-phenyl-2,6,6-trimethyl-1,5,6,7-tetrahydro-s-1-indacenyl)(2,3,4,5-tetramethyl-1-cyclopentadienyl)zirconium dichloride;
dimethylsilylene(3-pheny-5,5,8,8-tetramethyl-5,6,7,8-tetrahydrobenz[f]-1-indenyl)(2,3,4,5-tetramethyl-1-cyclopentadienyl)zirconium dichloride;
dimethylsilylene(3-phenylbenz[f]-1-indenyl)(2,3,4,5-tetramethyl-1-cyclopentadienyl)zirconium dichloride;
dimethylsilylene(2-methyl-3-phenylbenz[f]-1-indenyl)(2,3,4,5-tetramethyl-1-cyclopentadienyl)zirconium dichloride;
dimethylsilylene(2,5,5,8,8-pentamethyl-3-phenyl-5,6,7,8-tetrahydrobenz[f]-1-indenyl)(2,3,4,5-tetramethyl-1-cyclopentadienyl)zirconium dichloride;
dimethylsilylene(3-phenylbenz[e]-1-indenyl)(2,3,4,5-tetramethyl-1-cyclopentadienyl)zirconium dichloride;
dimethylsilylene(2-methyl-3-phenylbenz[e]-1-indenyl)(2,3,4,5-tetramethyl-1-cyclopentadienyl)zirconium dichloride;
dimethylsilylene(3-(4-methylphenyl)-1-indenyl)(2,3,4,5-tetramethyl-1-cyclopentadienyl)zirconium dichloride;
dimethylsilylene(3-(3,5-dimethylphenyl)-1-indenyl)(2,3,4,5-tetramethyl-1-cyclopentadienyl)zirconium dichloride;
dimethylsilylene(3-(2,6-dimethylphenyl)-1-indenyl)(2,3,4,5-tetramethyl-1-cyclopentadienyl)zirconium dichloride;
dimethylsilylene(3-(2,4-dimethylphenyl)-1-indenyl)(2,3,4,5-tetramethyl-1-cyclopentadienyl)zirconium dichloride;
dimethylsilylene(3-(3,4-dimethylphenyl)-1-indenyl)(2,3,4,5-tetramethyl-1-cyclopentadienyl)zirconium dichloride;
dimethylsilylene(3-(2,3-dimethylphenyl)-1-indenyl)(2,3,4,5-tetramethyl-1-cyclopentadienyl)zirconium dichloride;
dimethylsilylene(3-(2,5-dimethylphenyl)-1-indenyl)(2,3,4,5-tetramethyl-1-cyclopentadienyl)zirconium dichloride;
dimethylsilylene(3-(2,4,6-trimethylphenyl)-1-indenyl)(2,3,4,5-tetramethyl-1-cyclopentadienyl)zirconium dichloride;
dimethylsilylene(3-(2,3,4-trimethylphenyl)-1-indenyl)(2,3,4,5-tetramethyl-1-cyclopentadienyl)zirconium dichloride;
dimethylsilylene(3-(3,4,5-trimethylphenyl)-1-indenyl)(2,3,4,5-tetramethyl-1-cyclopentadienyl)zirconium dichloride;
dimethylsilylene(3-(2,3,5-trimethylphenyl)-1-indenyl)(2,3,4,5-tetramethyl-1-cyclopentadienyl)zirconium dichloride;
dimethylsilylene(3-(2,3,6-trimethylphenyl)-1-indenyl)(2,3,4,5-tetramethyl-1-cyclopentadienyl)zirconium dichloride;
dimethylsilylene(3-(2,4,5-trimethylphenyl)-1-indenyl)(2,3,4,5-tetramethyl-1-cyclopentadienyl)zirconium dichloride;
dimethylsilylene(3-(2,3,4,5-tetramethylphenyl)-1-indenyl)(2,3,4,5-tetramethyl-1-cyclopentadienyl)zirconium dichloride;
dimethylsilylene(3-(2,3,4,5-tetramethylphenyl)-1-indenyl)(2,3,4,5-tetramethyl-1-cyclopentadienyl)zirconium dichloride;
dimethylsilylene(3-(2,3,4,6-tetramethylphenyl)-1-indenyl)(2,3,4,5-tetramethyl-1-cyclopentadienyl)zirconium dichloride;
dimethylsilylene(3-(2,3,5,6-tetramethylphenyl)-1-indenyl)(2,3,4,5-tetramethyl-1-cyclopentadienyl)zirconium dichloride;
dimethylsilylene(3-(2,3,4,5,6-pentamethylphenyl)-1-indenyl)(2,3,4,5-tetramethyl-1-cyclopentadienyl)zirconium dichloride;
dimethylsilylene(3-(2-methylphenyl)-1-indenyl)(2,3,4,5-tetramethyl-1-cyclopentadienyl)zirconium dichloride;
dimethylsilylene(3-(2-ethylphenyl)-1-indenyl)(2,3,4,5-tetramethyl-1-cyclopentadienyl)zirconium dichloride;
dimethylsilylene(3-(2-propylphenyl)-1-indenyl)(2,3,4,5-tetramethyl-1-cyclopentadienyl)zirconium dichloride;
dimethylsilylene(3-(2-butylphenyl)-1-indenyl)(2,3,4,5-tetramethyl-1-cyclopentadienyl)zirconium dichloride;
dimethylsilylene(3-(3-methylphenyl)-1-indenyl)(2,3,4,5-tetramethyl-1-cyclopentadienyl)zirconium dichloride;
dimethylsilylene(3-(3-ethylphenyl)-1-indenyl)(2,3,4,5-tetramethyl-1-cyclopentadienyl)zirconium dichloride;
dimethylsilylene(3-(3-propylphenyl)-1-indenyl)(2,3,4,5-tetramethyl-1-cyclopentadienyl)zirconium dichloride;
dimethylsilylene(3-(3-butylphenyl)-1-indenyl)(2,3,4,5-tetramethyl-1-cyclopentadienyl)zirconium dichloride;
dimethylsilylene(3-(3-t-butylphenyl)-1-indenyl)(2,3,4,5-tetramethyl-1-cyclopentadienyl)zirconium dichloride;
dimethylsilylene(3-(4-methylphenyl)-1-indenyl)(2,3,4,5-tetramethyl-1-cyclopentadienyl)zirconium dichloride;
dimethylsilylene(3-(4-ethylphenyl)-1-indenyl)(2,3,4,5-tetramethyl-1-cyclopentadienyl)zirconium dichloride;
dimethylsilylene(3-(4-propylphenyl)-1-indenyl)(2,3,4,5-tetramethyl-1-cyclopentadienyl)zirconium dichloride;
dimethylsilylene(3-(4-butylphenyl)-1-indenyl)(2,3,4,5-tetramethyl-1-cyclopentadienyl)zirconium dichloride;
dimethylsilylene(3-(4-t-butylphenyl)-1-indenyl)(2,3,4,5-tetramethyl-1-cyclopentadienyl)zirconium dichloride;
dimethylsilylene(3-(4-biphenyl)-1-indenyl)(2,3,4,5-tetramethyl-1-cyclopentadienyl)zirconium dichloride;
dimethylsilylene(3-(3-biphenyl)-1-indenyl)(2,3,4,5-tetramethyl-1-cyclopentadienyl)zirconium dichloride;
dimethylsilylene(3-(2-biphenyl)-1-indenyl)(2,3,4,5-tetramethyl-1-cyclopentadienyl)zirconium dichloride;
dimethylsilylene(3-(3,5-diphenylphenyl)-1-indenyl)(2,3,4,5-tetramethyl-1-cyclopentadienyl)zirconium dichloride;
dimethylsilylene(3-(3,5-di-t-butylphenyl)-1-indenyl)(2,3,4,5-tetramethyl-1-cyclopentadienyl)zirconium dichloride;
dimethylsilylene(3-(2-fluorophenyl)-1-indenyl)(2,3,4,5-tetramethyl-1-cyclopentadienyl)zirconium dichloride;
dimethylsilylene(3-(3-fluorophenyl)-1-indenyl)(2,3,4,5-tetramethyl-1-cyclopentadienyl)zirconium dichloride;
dimethylsilylene(3-(4-fluorophenyl)-1-indenyl)(2,3,4,5-tetramethyl-1-cyclopentadienyl)zirconium dichloride;
dimethylsilylene(3-(2,3-difluorophenyl)-1-indenyl)(2,3,4,5-tetramethyl-1-cyclopentadienyl)zirconium dichloride;

dimethylsilylene(3-(2,4-difluorophenyl)-1-indenyl)(2,3,4,5-tetramethyl-1-cyclopentadienyl)zirconium dichloride;

dimethylsilylene(3-(2,5-difluorophenyl)-1-indenyl)(2,3,4,5-tetramethyl-1-cyclopentadienyl)zirconium dichloride;

dimethylsilylene(3-(2,6-difluorophenyl)-1-indenyl)(2,3,4,5-tetramethyl-1-cyclopentadienyl)zirconium dichloride;

dimethylsilylene(3-(3,4-difluorophenyl)-1-indenyl)(2,3,4,5-tetramethyl-1-cyclopentadienyl)zirconium dichloride;

dimethylsilylene(3-(3,5-difluorophenyl)-1-indenyl)(2,3,4,5-tetramethyl-1-cyclopentadienyl)zirconium dichloride;

dimethylsilylene(3-(2,3,4-trifluorophenyl)-1-indenyl)(2,3,4,5-tetramethyl-1-cyclopentadienyl)zirconium dichloride;

dimethylsilylene(3-(2,3,5-trifluorophenyl)-1-indenyl)(2,3,4,5-tetramethyl-1-cyclopentadienyl)zirconium dichloride;

dimethylsilylene(3-(2,3,6-trifluorophenyl)-1-indenyl)(2,3,4,5-tetramethyl-1-cyclopentadienyl)zirconium dichloride;

dimethylsilylene(3-(2,4,5-trifluorophenyl)-1-indenyl)(2,3,4,5-tetramethyl-1-cyclopentadienyl)zirconium dichloride;

dimethylsilylene(3-(2,4,6-trifluorophenyl)-1-indenyl)(2,3,4,5-tetramethyl-1-cyclopentadienyl)zirconium dichloride;

dimethylsilylene(3-(3,4,5-trifluorophenyl)-1-indenyl)(2,3,4,5-tetramethyl-1-cyclopentadienyl)zirconium dichloride;

dimethylsilylene(3-(2,3,4,5-tetrafluorophenyl)-1-indenyl)(2,3,4,5-tetramethyl-1-cyclopentadienyl)zirconium dichloride;

dimethylsilylene(3-(2,3,4,6-tetrafluorophenyl)-1-indenyl)(2,3,4,5-tetramethyl-1-cyclopentadienyl)zirconium dichloride;

dimethylsilylene(3-(2,3,5,6-tetrafluorophenyl)-1-indenyl)(2,3,4,5-tetramethyl-1-cyclopentadienyl)zirconium dichloride;

dimethylsilylene(3-(pentafluorophenyl)-1-indenyl)(2,3,4,5-tetramethyl-1-cyclopentadienyl)zirconium dichloride;

dimethylsilylene(3-(2-chlorophenyl)-1-indenyl)(2,3,4,5-tetramethyl-1-cyclopentadienyl)zirconium dichloride;

dimethylsilylene(3-(3-chlorophenyl)-1-indenyl)(2,3,4,5-tetramethyl-1-cyclopentadienyl)zirconium dichloride;

dimethylsilylene(3-(4-chlorophenyl)-1-indenyl)(2,3,4,5-tetramethyl-1-cyclopentadienyl)zirconium dichloride;

dimethylsilylene(3-(2,6-dichlorophenyl)-1-indenyl)(2,3,4,5-tetramethyl-1-cyclopentadienyl)zirconium dichloride;

dimethylsilylene(3-(3,5-dichlorophenyl)-1-indenyl)(2,3,4,5-tetramethyl-1-cyclopentadienyl)zirconium dichloride;

dimethylsilylene(3-(2,4,6-trichlorophenyl)-1-indenyl)(2,3,4,5-tetramethyl-1-cyclopentadienyl)zirconium dichloride;

dimethylsilylene(3-(2-trifluoromethylphenyl)-1-indenyl)(2,3,4,5-tetramethyl-1-cyclopentadienyl)zirconium dichloride;

dimethylsilylene(3-(3-trifluoromethylphenyl)-1-indenyl)(2,3,4,5-tetramethyl-1-cyclopentadienyl)zirconium dichloride;

dimethylsilylene(3-(4-trifluoromethylphenyl)-1-indenyl)(2,3,4,5-tetramethyl-1-cyclopentadienyl)zirconium dichloride;

dimethylsilylene(3-(3,5-bis(trifluoromethyl)phenyl)-1-indenyl)(2,3,4,5-tetramethyl-1-cyclopentadienyl)zirconium dichloride;

dimethylsilylene(3-(2-methoxyphenyl)-1-indenyl)(2,3,4,5-tetramethyl-1-cyclopentadienyl)zirconium dichloride;

dimethylsilylene(3-(3-methoxyphenyl)-1-indenyl)(2,3,4,5-tetramethyl-1-cyclopentadienyl)zirconium dichloride;

dimethylsilylene(3-(4-methoxyphenyl)-1-indenyl)(2,3,4,5-tetramethyl-1-cyclopentadienyl)zirconium dichloride;

dimethylsilylene(3-(2,6-dimethoxyphenyl)-1-indenyl)(2,3,4,5-tetramethyl-1-cyclopentadienyl)zirconium dichloride;

dimethylsilylene(3-(3,5-dimethoxyphenyl)-1-indenyl)(2,3,4,5-tetramethyl-1-cyclopentadienyl)zirconium dichloride;

dimethylsilylene(3-(2,4,6-trimethoxyphenyl)-1-indenyl)(2,3,4,5-tetramethyl-1-cyclopentadienyl)zirconium dichloride;

dimethylsilylene(3-(1-naphthyl)-1-indenyl)(2,3,4,5-tetramethyl-1-cyclopentadienyl)zirconium dichloride;

dimethylsilylene(3-(2-naphthyl)-1-indenyl)(2,3,4,5-tetramethyl-1-cyclopentadienyl)zirconium dichloride;

dimethylsilylene(2-methyl-3-(2-naphthyl)-1-indenyl)(2,3,4,5-tetramethyl-1-cyclopentadienyl)zirconium dichloride;

dimethylsilylene(3-(1-anthryl)-1-indenyl)(2,3,4,5-tetramethyl-1-cyclopentadienyl)zirconium dichloride;

dimethylsilylene(3-(2-anthryl)-1-indenyl)(2,3,4,5-tetramethyl-1-cyclopentadienyl)zirconium dichloride;

dimethylsilylene(3-(9-anthryl)-1-indenyl)(2,3,4,5-tetramethyl-1-cyclopentadienyl)zirconium dichloride;

dimethylsilylene(3-(9-phenanthryl)-1-indenyl)(2,3,4,5-tetramethyl-1-cyclopentadienyl)zirconium dichloride;

dimethylsilylene(3-(2-furanyl)-1-indenyl)(2,3,4,5-tetramethyl-1-cyclopentadienyl)zirconium dichloride;

dimethylsilylene(3-(2-furanyl)-2-methyl-1-indenyl)(2,3,4,5-tetramethyl-1-cyclopentadienyl)zirconium dichloride;

dimethylsilylene(3-(3-furanyl)-1-indenyl)(2,3,4,5-tetramethyl-1-cyclopentadienyl)zirconium dichloride;

dimethylsilylene(3-(3-furanyl)-2-methyl-1-indenyl)(2,3,4,5-tetramethyl-1-cyclopentadienyl)zirconium dichloride;

dimethylsilylene(3-(2-thiophenyl)-1-indenyl)(2,3,4,5-tetramethyl-1-cyclopentadienyl)zirconium dichloride;

dimethylsilylene(2-methyl-3-(2-thiophenyl)-1-indenyl)(2,3,4,5-tetramethyl-1-cyclopentadienyl)zirconium dichloride;

dimethylsilylene(3-(3-thiophenyl)-1-indenyl)(2,3,4,5-tetramethyl-1-cyclopentadienyl)zirconium dichloride;

dimethylsilylene(2-methyl-3-(3-thiophenyl)-1-indenyl)(2,3,4,5-tetramethyl-1-cyclopentadienyl)zirconium dichloride;

dimethylsilylene(3-(2-pyridyl)-1-indenyl)(2,3,4,5-tetramethyl-1-cyclopentadienyl)zirconium dichloride;

dimethylsilylene(2-methyl-3-(2-pyridyl)-1-indenyl)(2,3,4,5-tetramethyl-1-cyclopentadienyl)zirconium dichloride;

dimethylsilylene(3-(3-pyridyl)-1-indenyl)(2,3,4,5-tetramethyl-1-cyclopentadienyl)zirconium dichloride;

dimethylsilylene(2-methyl-3-(3-pyridyl)-1-indenyl)(2,3,4,5-tetramethyl-1-cyclopentadienyl)zirconium dichloride;

titanium and hafnium analogs of the above zirconium dichloride compounds wherein the zirconium transition metal is replaced with titanium or hafnium; and dimethyl analogs of the above dichloride compounds wherein the chloride groups on the zirconium, hafnium, or titanium transition metal are replaced with methyl groups.

Metallocene Catalyst Systems

This invention also relates to a catalyst system comprising:
(i) a bridged metallocene compound represented by the following formula:

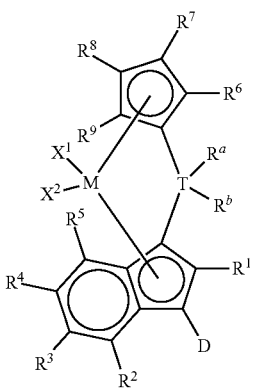

wherein:

M is a group 4 metal (preferably, M is zirconium or hafnium; more preferably, zirconium);

T is a group 14 atom (preferably, silicon or germanium; more preferably, silicon);

D is a substituted or unsubstituted aromatic group (preferably, D is selected from the group consisting of substituted or unsubstituted phenyl, naphthyl, biphenyl, cyclopropenyl, tropylium, cyclooctatetraenyl, furanyl, pyridinyl, borabenzyl, thiophenyl, azolyl, oxazolyl, and imidazolyl; more preferably, D is selected from the group consisting of substituted or unsubstituted phenyl, naphthyl, biphenyl, cyclopropenyl, furanyl, pyridinyl, thiophenyl, azolyl, oxazolyl, and imidazolyl);

$R^a$ and $R^b$ are independently, hydrogen, halogen, or a $C_1$ to $C_{20}$ substituted or unsubstituted hydrocarbyl, and $R^a$ and $R^b$ can form a cyclic structure including substituted or unsubstituted aromatic, partially saturated, or saturated cyclic or fused ring system (preferably each $R^a$ and $R^b$ is independently selected from the group consisting of halides, $C_1$ to $C_{20}$ substituted or unsubstituted hydrocarbyl groups, and cyclic structures where $R^a$ and $R^b$ form a heterocyclopentyl, heterocyclobutyl, or heterocyclohexyl structure with T being the heteroatom; more preferably each $R^a$ and $R^b$ is independently selected from the group consisting of chlorides, fluorides, methyl, and ethyl groups; more preferably, each $R^a$ and $R^b$ is, independently, selected from the group consisting of chlorides, fluorides, methyl, and ethyl groups);

each $X^1$ and $X^2$ is independently selected from the group consisting of $C_1$ to $C_{20}$ substituted or unsubstituted hydrocarbyl groups, hydrides, amides, amines, alkoxides, sulfides, phosphides, halides, dienes, phosphines, and ethers; and $X^1$ and $X^2$ can form a cyclic structure including aromatic, partially saturated, or saturated cyclic or fused ring system; more preferably, each $X^1$ and $X^2$ is independently selected from the group consisting of chlorides, fluorides, methyl, and ethyl groups;

each of $R^1$, $R^2$, $R^3$, $R^4$, and $R^5$ is, independently, hydrogen, halide, alkoxide or a $C_1$ to $C_{40}$ substituted or unsubstituted hydrocarbyl group, and any of adjacent $R^2$, $R^3$, $R^4$, and/or $R^5$ groups may form a fused ring or multicenter fused ring systems, where the rings may be substituted or unsubstituted, and may be aromatic, partially unsaturated, or unsaturated (preferably, each of $R^1$, $R^2$, $R^3$, $R^4$, and $R^5$ is, independently, a $C_1$ to $C_{20}$ substituted or unsubstituted hydrocarbyl group); and each of $R^6$, $R^7$, $R^8$, and $R^9$ is, each independently, hydrogen or a $C_1$ to $C_{40}$ substituted or unsubstituted hydrocarbyl group (preferably, each of $R^6$, $R^7$, $R^8$, and $R^9$ is, a $C_1$ to $C_{40}$ substituted or unsubstituted hydrocarbyl group; more preferably, each of $R^6$, $R^7$, $R^8$, and $R^9$ is, independently, a $C_1$ to $C_{20}$ substituted or unsubstituted hydrocarbyl group;

more preferably, each of $R^6$, $R^7$, $R^8$, and $R^9$ is, independently, selected from the group consisting of methyl, ethyl, propyl, isopropyl, n-butyl, sec-butyl, t-butyl, pentyl, hexyl, heptyl, octyl, decyl, and undecyl groups; even more preferably, each of $R^6$, $R^7$, $R^8$, and $R^9$ is, independently, selected from the group consisting of methyl, ethyl, and n-propyl groups;

preferably, adjacent $R^6$, $R^7$, $R^8$, and/or $R^9$ groups fuse together with the cyclopentadienyl group to form a substituted or unsubstituted fluorene);

further provided that at least two of $R^6$, $R^7$, $R^8$, and $R^9$ are $C_1$ to $C_{40}$ substituted or unsubstituted hydrocarbyl groups;

(ii) at least one activator (preferably, an alumoxane or a stoichiometric activator);

(iii) optionally, a support material; and (iv) optionally, a cocatalyst.

The metallocene catalyst system of this invention comprises a metallocene compound, an activator, an optional support material, and an optional cocatalyst/scavenger. The metallocene compound was discussed above. The activator, optional support material, and optional cocatalyst/scavenger are discussed below.

Activators

The term "activator" is used herein to be any compound which can activate any one of the metallocene compounds described above by converting the neutral catalyst compound to a catalytically active metallocene compound cation. Activators useful herein include alumoxanes and stoichiometric activators.

Alumoxanes

Preferred activators typically include alumoxane compounds (or "alumoxanes") and modified alumoxane compounds. Alumoxanes are generally oligomeric compounds containing —Al($R^1$)—O— sub-units, where $R^1$ is an alkyl group. Examples of alumoxanes include methylalumoxane (MAO), modified methylalumoxane (MMAO), ethylalumoxane, isobutylalumoxane, and mixtures thereof. Alkylalumoxanes and modified alkylalumoxanes are suitable as catalyst activators, particularly when the abstractable ligand is an alkyl, halide, alkoxide, or amide. Mixtures of different alumoxanes and modified alumoxanes may also be used. It may be preferable to use a visually clear methylalumoxane. A cloudy or gelled alumoxane can be filtered to produce a clear solution or clear alumoxane can be decanted from the cloudy solution. Another useful alumoxane is a modified methylalumoxane (MMAO) cocatalyst type 3A (commercially available from Akzo Chemicals, Inc. under the trade name Modified Methylalumoxane type 3A, covered under U.S. Pat. No. 5,041,584). In preferred embodiments of this invention, the activator is an alkylalumoxane, preferably methylalumoxane or isobutylalumoxane.

The minimum activator metal-to-zirconium (preferably, aluminum from the alumoxane to zirconium from the zirconocene catalyst of the catalyst system) ratio is a 1:1 molar ratio. Alternate preferred ratios include up to 5000:1, preferably up to 500:1, preferably up to 200:1, preferably up to 100:1, or preferably from 1:1 to 50:1.

In some embodiments of this invention, the alumoxane activator may be supported on a support material prior to contact with the metallocene compound. In other embodiments, the alumoxane activator is combined with the metallocene compound prior to being placed upon a support material. In yet other embodiments, the alumoxane activator may be combined with the metallocene compound in the absence of a support material.

Stoichiometric Activators

In preferred embodiments, the catalyst system of this invention further comprises one or more stoichiometric activators. A stoichiometric activator is a non-alumoxane compound which when combined in a reaction with the metallocene compound forms a catalytically active species at a molar ratio of stoichiometric activator to metallocene compound of 10:1 or less (preferably 5:1, more preferably 2:1, or even more preferably 1:1). It is within the scope of this invention to use a molar ratio of stoichiometric activator to metallocene compound of greater than 10:1. However, one of skill in the art would appreciate that the stoichiometric activator would be in excess and that a catalytically active species may be obtained using a molar ratio of stoichiometric activator to metallocene compound of 10:1 or less.

The typical stoichiometric (or non-alumoxane) activator-to-catalyst ratio is a 1:1 molar ratio. A particularly useful range is from 0.5:1 to 10:1, preferably 1:1 to 5:1. Alternate preferred ranges include from 0.1:1 to 100:1, alternately from 0.5:1 to 200:1, alternately from 1:1 to 500:1 alternately from 1:1 to 1000:1.

Stoichiometric activators are non-alumoxane compounds which may be neutral or ionic, such as tri(n-butyl)ammonium tetrakis(pentafluorophenyl)borate, a tris perfluorophenyl boron metalloid precursor, or a tris perfluoronaphthyl boron metalloid precursor, polyhalogenated heteroborane anions (WO 98/43983), boric acid (U.S. Pat. No. 5,942,459), or a combination thereof. It is also within the scope of this invention to use stoichiometric activators alone or in combination with alumoxane or modified alumoxane activators.

Neutral Stoichiometric Activators

Examples of neutral stoichiometric activators include tri-substituted boron, tellurium, aluminum, gallium, indium, or mixtures thereof. The three substituent groups are each independently selected from alkyls, alkenyls, halogens, substituted alkyls, aryls, arylhalides, alkoxy, and halides. Preferably, the three groups are independently selected from halogen, mono or multicyclic (including halosubstituted) aryls, alkyls, alkenyl compounds, and mixtures thereof; preferred are alkenyl groups having 1 to 20 carbon atoms, alkyl groups having 1 to 20 carbon atoms, alkoxy groups having 1 to 20 carbon atoms, and aryl groups having 3 to 20 carbon atoms (including substituted aryls). More preferably, the three groups are alkyls having 1 to 4 carbon groups, phenyl, naphthyl, or mixtures thereof. Even more preferably, the three groups are halogenated, preferably fluorinated, aryl groups. Most preferably, the neutral stoichiometric activator is tris perfluorophenyl boron or tris perfluoronaphthyl boron.

Ionic Stoichiometric Activators

Ionic stoichiometric activators may contain an active proton, or some other cation associated with, but not coordinated to, or only loosely coordinated to, the remaining anion of the activator. Such compounds and the like are described in European publications EP 0 570 982 A; EP 0 520 732 A; EP 0 495 375 A; EP 0 500 944 B1; EP 0 277 003 A; EP 0 277 004 A; U.S. Pat. Nos. 5,153,157; 5,198,401; 5,066,741; 5,206,197; 5,241,025; 5,384,299; 5,502,124; and U.S. patent application Ser. No. 08/285,380, filed Aug. 3, 1994; all of which are herein fully incorporated by reference.

Ionic stoichiometric activators comprise a cation, which is preferably a Bronsted acid capable of donating a proton, and a compatible non-coordinating anion. Preferably, the anion is relatively large (bulky), capable of stabilizing the catalytically active species (preferably a group 4 catalytically active species) which is formed when the metallocene compound and the stoichiometric activator are combined. Preferably the anion will be sufficiently labile to be displaced by olefinic, diolefinic, and acetylenically unsaturated substrates or other neutral Lewis bases, such as ethers, amines, and the like. Two classes of compatible non-coordinating anions have been disclosed in EP 0 277,003 A and EP 0 277,004 A: 1) anionic coordination complexes comprising a plurality of lipophilic radicals covalently coordinated to and shielding a central charge-bearing metal or metalloid core, and 2) anions comprising a plurality of boron atoms, such as carboranes, metallacarboranes, and boranes.

Ionic stoichiometric activators comprise an anion, preferably a non-coordinating anion. The term "non-coordinating anion" (NCA) means an anion which either does not coordinate to said cation or which is only weakly coordinated to said cation thereby remaining sufficiently labile to be displaced by a neutral Lewis base. "Compatible" non-coordinating anions are those which are not degraded to neutrality when the initially formed complex decomposes. Further, the anion will not transfer an anionic substituent or fragment to the cation so as to cause it to form a neutral four coordinate metallocene compound and a neutral by-product from the anion. Non-coordinating anions useful in accordance with this invention are those that are compatible, stabilize the metallocene cation in the sense of balancing its ionic charge at +1, yet retain sufficient lability to permit displacement by an ethylenically or acetylenically unsaturated monomer during polymerization.

In a preferred embodiment of this invention, the ionic stoichiometric activators are represented by the following formula (I):

$$(Z)_d^+ A^{d-} \qquad (1)$$

wherein $(Z)_d^+$ is the cation component and $A^{d-}$ is the anion component; where Z is (L-H) or a reducible Lewis Acid, L is an neutral Lewis base; H is hydrogen; $(L-H)^+$ is a Bronsted acid; $A^{d-}$ is a non-coordinating anion having the charge d+; and d is an integer from 1 to 3.

When Z is (L-H) such that the cation component is $(L-H)_d^+$, the cation component may include Bronsted acids such as protonated Lewis bases capable of protonating a moiety, such as an alkyl or aryl, from the bulky ligand metallocene containing transition metal catalyst precursor, resulting in a cationic transition metal species. Preferably, the activating cation $(L-H)_d^+$ is a Bronsted acid, capable of donating a proton to the transition metal catalytic precursor resulting in a transition metal cation, including ammoniums, oxoniums, phosphoniums, silyliums, and mixtures thereof, preferably ammoniums of methylamine, aniline, dimethylamine, diethylamine, N-methylaniline, diphenylamine, trimethylamine, triethylamine, N,N-dimethylaniline, methyldiphenylamine, pyridine, p-bromo N,N-dimethylaniline, p-nitro-N, N-dimethylaniline, phosphoniums from triethylphosphine, triphenylphosphine, and diphenylphosphine, oxoniums from ethers, such as dimethyl ether diethyl ether, tetrahydrofuran, and dioxane, sulfoniums from thioethers, such as diethyl thioethers and tetrahydrothiophene, and mixtures thereof.

When Z is a reducible Lewis acid, $(Z)_d^+$ is preferably represented by the formula: $(Ar_3C)^+$, where Ar is aryl or aryl substituted with a heteroatom, a $C_1$ to $C_{40}$ hydrocarbyl, or a substituted $C_1$ to $C_{40}$ hydrocarbyl, preferably $(Z)_d^+$ is represented by the formula: $(Ph_3C)^+$, where Ph is phenyl or phenyl substituted with a heteroatom, a $C_1$ to $C_{40}$ hydrocarbyl, or a substituted $C_1$ to $C_{40}$ hydrocarbyl. In a preferred embodiment, the reducible Lewis acid is triphenyl carbenium.

The anion component $A^{d-}$ includes those having the formula $[M^{k+}Q_n]^{d-}$ wherein k is 1, 2, or 3; n is 1, 2, 3, 4, 5, or 6, preferably 3, 4, 5, or 6; (n−k)=d; M is an element selected from group 13 of the Periodic Table of the Elements, preferably boron or aluminum; and each Q is, independently, a hydride, bridged or unbridged dialkylamido, halide, alkoxide, aryloxide, hydrocarbyl, substituted hydrocarbyl, halocarbyl, substituted halocarbyl, and halosubstituted-hydrocarbyl radicals, said Q having up to 20 carbon atoms with the proviso that in not more than one occurrence is Q a halide, and two Q groups may form a ring structure. Preferably, each Q is a fluorinated hydrocarbyl group having 1 to 20 carbon atoms, more preferably each Q is a fluorinated aryl group, and most preferably each Q is a pentafluoryl aryl group. Examples of suitable $A^{d-}$ components also include diboron compounds as disclosed in U.S. Pat. No. 5,447,895, which is fully incorporated herein by reference.

In other embodiments of this invention, the ionic stoichiometric activator may be an activator comprising expanded anions, represented by the formula:

$$(A^{*+a})_b(Z^*J^*_J)^{-c}_d;$$

wherein $A^*$ is a cation having charge +a; $Z^*$ is an anion group of from 1 to 50 atoms not counting hydrogen atoms, further containing two or more Lewis base sites; $J^*$ independently each occurrence is a Lewis acid coordinated to at least one Lewis base site of $Z^*$, and optionally two or more such $J^*$ groups may be joined together in a moiety having multiple Lewis acid functionality; J is a number from 2 to 12; and a, b, c, and d are integers from 1 to 3, with the proviso that a×b is equal to c×d. Examples of such activators comprising expandable anions may be found in U.S. Pat. No. 6,395,671, which is fully incorporated herein by reference.

Examples of ionic stoichiometric activators useful in the catalyst system of this invention are:
trimethylammonium tetraphenylborate, triethylammonium tetraphenylborate, tripropylammonium tetraphenylborate, tri(n-butyl)ammonium tetraphenylborate, tri(t-butyl)ammonium tetraphenylborate, N,N-dimethylanilinium tetraphenylborate, N,N-diethylanilinium tetraphenylborate, N,N-dimethyl-(2,4,6-trimethylanilinium)tetraphenylborate,
tropillium tetraphenylborate, triphenylcarbenium tetraphenylborate, triphenylphosphonium tetraphenylborate triethylsilylium tetraphenylborate, benzene(diazonium)tetraphenylborate, trimethylammonium tetrakis(pentafluorophenyl)borate, triethylammonium tetrakis(pentafluorophenyl)borate, tripropylammonium tetrakis(pentafluorophenyl)borate, tri(n-butyl)ammonium tetrakis(pentafluorophenyl)borate, tri(sec-butyl)ammonium tetrakis(pentafluorophenyl)borate, N,N-dimethylanilinium tetrakis(pentafluorophenyl)borate, N,N-diethylanilinium tetrakis(pentafluorophenyl)borate, N,N-dimethyl-(2,4,6-trimethylanilinium)tetrakis(pentafluorophenyl)borate, tropillium tetrakis(pentafluorophenyl)borate, triphenylcarbenium tetrakis(pentafluorophenyl)borate, triphenylphosphonium tetrakis(pentafluorophenyl)borate, triethylsilylium tetrakis(pentafluorophenyl)borate, benzene(diazonium)tetrakis(pentafluorophenyl)borate, trimethylammonium tetrakis-(2,3,4,6-tetrafluorophenyl)borate, triethylammonium tetrakis-(2,3,4,6-tetrafluorophenyl)borate, tripropylammonium tetrakis-(2,3,4,6-tetrafluorophenyl)borate, tri(n-butyl)ammonium tetrakis-(2,3,4,6-tetrafluoro-phenyl)borate, dimethyl(t-butyl)ammonium tetrakis-(2,3,4,6-tetrafluorophenyl)borate, N,N-dimethylanilinium tetrakis-(2,3,4,6-tetrafluorophenyl)borate, N,N-diethylanilinium tetrakis-(2,3,4,6-tetrafluorophenyl)borate, N,N-dimethyl-(2,4,6-trimethylanilinium)tetrakis-(2,3,4,6-tetrafluorophenyl)borate, tropillium tetrakis-(2,3,4,6-tetrafluorophenyl)borate, triphenylcarbenium tetrakis-(2,3,4,6-tetrafluorophenyl)borate, triphenylphosphonium tetrakis-(2,3,4,6-tetrafluorophenyl)borate, triethylsilylium tetrakis-(2,3,4,6-tetrafluorophenyl)borate, benzene(diazonium)tetrakis-(2,3,4,6-tetrafluorophenyl)borate, trimethylammonium tetrakis(perfluoronaphthyl)borate, triethylammonium tetrakis(perfluoronaphthyl)borate, tripropylammonium tetrakis(perfluoronaphthyl)borate, tri(n-butyl)ammonium tetrakis(perfluoronaphthyl)borate, tri(t-butyl)ammonium tetrakis(perfluoronaphthyl)borate, N,N-dimethylanilinium tetrakis(perfluoronaphthyl)borate, N,N-diethylanilinium tetrakis(perfluoronaphthyl)borate, N,N-dimethyl-(2,4,6-trimethylanilinium)tetrakis(perfluoronaphthyl)borate, tropillium tetrakis(perfluoronaphthyl)borate, triphenylcarbenium tetrakis(perfluoronaphthyl)borate, triphenylphosphonium tetrakis(perfluoronaphthyl)borate, triethylsilylium tetrakis(perfluoronaphthyl)borate, benzene(diazonium)tetrakis(perfluoronaphthyl)borate, trimethylammonium tetrakis(perfluorobiphenyl)borate, triethylammonium tetrakis(perfluorobiphenyl)borate, tripropylammonium tetrakis(perfluorobiphenyl)borate, tri(n-butyl)ammonium tetrakis(perfluorobiphenyl)borate, tri(t-butyl)ammonium tetrakis(perfluorobiphenyl)borate, N,N-dimethylanilinium tetrakis(perfluorobiphenyl)borate, N,N-diethylanilinium tetrakis(perfluorobiphenyl)borate, N,N-dimethyl-(2,4,6-trimethylanilinium)tetrakis(perfluorobiphenyl)borate, tropillium tetrakis(perfluorobiphenyl)borate, triphenylcarbenium tetrakis(perfluorobiphenyl)borate, triphenylphosphonium tetrakis(perfluorobiphenyl)borate, triethylsilylium tetrakis(perfluorobiphenyl)borate, benzene(diazonium)tetrakis(perfluorobiphenyl)borate, trimethylammonium tetrakis(3,5-bis(trifluoromethyl)phenyl)borate, triethylammonium tetrakis(3,5-bis(trifluoromethyl)phenyl)borate, tripropylammonium tetrakis(3,5-bis(trifluoromethyl)phenyl)borate, tri(n-butyl)ammonium tetrakis(3,5-bis(trifluoromethyl)phenyl)borate, tri(t-butyl)ammonium tetrakis(3,5-bis(trifluoromethyl)phenyl)borate, N,N-dimethylanilinium tetrakis(3,5-bis(trifluoromethyl)phenyl)borate, N,N-diethylanilinium tetrakis(3,5-bis(trifluoromethyl)phenyl)borate, N,N-dimethyl-(2,4,6-trimethylanilinium)tetrakis(3,5-bis(trifluoromethyl)phenyl)borate, tropillium tetrakis(3,5-bis(trifluoromethyl)phenyl)borate, triphenylcarbenium tetrakis(3,5-bis(trifluoromethyl)phenyl)borate, triphenylphosphonium tetrakis(3,5-bis(trifluoromethyl)phenyl)borate, triethylsilylium tetrakis(3,5-bis(trifluoromethyl)phenyl)borate, benzene(diazonium)tetrakis(3,5-bis(trifluoromethyl)phenyl)borate, and dialkyl ammonium salts such as: di-(i-propyl)ammonium tetrakis(pentafluorophenyl)borate, and dicyclohexylammonium tetrakis(pentafluorophenyl)borate; and additional tri-substituted phosphonium salts such as tri(o-tolyl)phosphonium tetrakis(pentafluorophenyl)borate, and tri(2,6-dimethylphenyl)phosphonium tetrakis(pentafluorophenyl)borate.

Most preferably, the ionic stoichiometric activator is N,N-dimethylanilinium tetrakis(perfluoronaphthyl)borate, N,N-dimethylanilinium tetrakis(perfluorobiphenyl)borate, N,N-dimethylanilinium tetrakis(3,5-bis(trifluoromethyl)phenyl)borate, triphenylcarbenium tetrakis(perfluoronaphthyl)borate, triphenylcarbenium tetrakis(perfluorobiphenyl)borate, triphenylcarbenium tetrakis(3,5-bis(trifluoromethyl)phenyl)borate, or triphenylcarbenium tetrakis(perfluorophenyl)borate.

Bulky Ionic Stoichiometric Activators

"Bulky activator" as used herein refers to ionic stoichiometric activators represented by the formula:

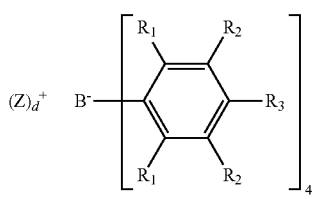

where:
each $R_1$ is, independently, a halide, preferably a fluoride;
each $R_2$ is, independently, a halide, a $C_6$ to $C_{20}$ substituted aromatic hydrocarbyl group or a siloxy group of the formula —O—Si—$R_a$, where $R_a$ is a $C_1$ to $C_{20}$ substituted or unsubstituted hydrocarbyl or hydrocarbylsilyl group (preferably, $R_2$ is a fluoride or a perfluorinated phenyl group);
each $R_3$ is a halide, $C_6$ to $C_{20}$ substituted aromatic hydrocarbyl group or a siloxy group of the formula —O—Si—$R_a$, where $R_a$ is a $C_1$ to $C_{20}$ substituted or unsubstituted hydrocarbyl or hydrocarbylsilyl group (preferably, $R_3$ is a fluoride or a $C_6$ perfluorinated aromatic hydrocarbyl group); wherein $R_2$ and $R_3$ can form one or more saturated or unsaturated, substituted or unsubstituted rings (preferably, $R_2$ and $R_3$ form a perfluorinated phenyl ring); $(Z)_d^+$ is the cation component; where Z is (L-H) or a reducible Lewis Acid, L is an neutral Lewis base; H is hydrogen; $(L-H)^+$ is a Bronsted acid; and d is an integer from 1 to 3;
wherein the boron anion component has a molecular weight of greater than 1020 g/mol; and
wherein at least three of the substituents on the B atom each have a molecular volume of greater than 250 cubic Å, alternately greater than 300 cubic Å, or alternately greater than 500 cubic Å.

"Molecular volume" is used herein as an approximation of spatial steric bulk of an activator molecule in solution. Comparison of substituents with differing molecular volumes allows the substituent with the smaller molecular volume to be considered "less bulky" in comparison to the substituent with the larger molecular volume. Conversely, a substituent with a larger molecular volume may be considered "more bulky" than a substituent with a smaller molecular volume.

Molecular volume may be calculated as reported in "A Simple 'Back of the Envelope' Method for Estimating the Densities and Molecular Volumes of Liquids and Solids," Journal of Chemical Education, Vol. 71, No. 11, November 1994, pp. 962-964. Molecular volume (MV), in units of cubic Å, is calculated using the formula: $MV=8.3V_s$, where $V_s$ is the scaled volume. $V_s$ is the sum of the relative volumes of the constituent atoms, and is calculated from the molecular formula of the substituent using the following table of relative volumes. For fused rings, the $V_s$ is decreased by 7.5% per fused ring.

| Element | Relative Volume |
|---|---|
| H | 1 |
| $1^{st}$ short period, Li to F | 2 |
| $2^{nd}$ short period, Na to Cl | 4 |
| $1^{st}$ long period, K to Br | 5 |
| $2^{nd}$ long period, Rb to I | 7.5 |
| $3^{rd}$ long period, Cs to Bi | 9 |

Exemplary bulky substituents of activators suitable herein and their respective scaled volumes and molecular volumes are shown in the table below. The dashed bonds indicate binding to boron, as in the general formula above.

| Activator | Structure of boron substituents | Molecular Formula of each substituent | $V_s$ | MV Per subst. (Å³) | Total MV (Å³) |
|---|---|---|---|---|---|
| Dimethylanilinium tetrakis(perfluoronaphthyl)borate | | $C_{10}F_7$ | 34 | 261 | 1044 |
| Dimethylanilinium tetrakis(perfluorobiphenyl)borate | | $C_{12}F_9$ | 42 | 349 | 1396 |

| Activator | Structure of boron substituents | Molecular Formula of each substituent | MV Per subst. ($Å^3$) $V_s$ | Total MV ($Å^3$) |
|---|---|---|---|---|
| [4-tButyl-PhNMe$_2$H] [(C$_6$F$_3$(C$_6$F$_5$)$_2$)$_4$B] | | $C_{18}F_{13}$ | 62 515 | 2060 |

Exemplary bulky ionic stoichiometric activators useful in catalyst systems herein include: trimethylammonium tetrakis (perfluoronaphthyl)borate, triethylammonium tetrakis(perfluoronaphthyl)borate, tripropylammonium tetrakis(perfluoronaphthyl)borate, tri(n-butyl)ammonium tetrakis (perfluoronaphthyl)borate, tri(t-butyl)ammonium tetrakis (perfluoronaphthyl)borate, N,N-dimethylanilinium tetrakis (perfluoronaphthyl)borate, N,N-diethylanilinium tetrakis (perfluoronaphthyl)borate, N,N-dimethyl-(2,4,6-trimethylanilinium)tetrakis(perfluoronaphthyl)borate, tropillium tetrakis(perfluoronaphthyl)borate, triphenylcarbenium tetrakis(perfluoronaphthyl)borate, triphenylphosphonium tetrakis(perfluoronaphthyl)borate, triethylsilylium tetrakis(perfluoronaphthyl)borate, benzene(diazonium)tetrakis (perfluoronaphthyl)borate, trimethylammonium tetrakis (perfluorobiphenyl)borate, triethylammonium tetrakis (perfluorobiphenyl)borate, tripropylammonium tetrakis (perfluorobiphenyl)borate, tri(n-butyl)ammonium tetrakis (perfluorobiphenyl)borate, tri(t-butyl)ammonium tetrakis (perfluorobiphenyl)borate, N,N-dimethylanilinium tetrakis (perfluorobiphenyl)borate, N,N-diethylanilinium tetrakis (perfluorobiphenyl)borate, N,N-dimethyl-(2,4,6-trimethylanilinium)tetrakis(perfluorobiphenyl)borate, tropillium tetrakis(perfluorobiphenyl)borate, triphenylcarbenium tetrakis(perfluorobiphenyl)borate, triphenylphosphonium tetrakis(perfluorobiphenyl)borate, triethylsilylium tetrakis(perfluorobiphenyl)borate, benzene(diazonium)tetrakis (perfluorobiphenyl)borate, [4-t-butyl-PhNMe$_2$H][(C$_6$F$_3$ (C$_6$F$_5$)$_2$)$_4$B], (where Ph is phenyl and Me is methyl), and the types disclosed in U.S. Pat. No. 7,297,653.

In another embodiment of this invention, an activation method using ionic compounds not containing an active proton but capable of producing a bulky ligand metallocene catalyst cation and their non-coordinating anion are also contemplated, and are described in EP 0 426 637 A, EP 0 573 403 A, and U.S. Pat. No. 5,387,568, which are all herein incorporated by reference.

In another embodiment of this invention, inventive processes also can employ stoichiometric activator compounds that are initially neutral Lewis acids but form a cationic metal complex and a noncoordinating anion, or a zwitterionic complex upon reaction with the metallocene compounds. For example, tris(pentafluorophenyl) boron or aluminum may act to abstract a hydrocarbyl or hydride ligand to yield an invention cationic metal complex and stabilizing noncoordinating anion, see EP 0 427 697 A and EP 0 520 732 A for illustrations of analogous group 4 metallocene compounds. Also, see the methods and compounds of EP 0 495 375 A. For formation of zwitterionic complexes using analogous group 4 compounds, see U.S. Pat. Nos. 5,624,878; 5,486,632; and 5,527,929.

In another embodiment of this invention, another suitable ionic stoichiometric activator comprises a salt of a cationic oxidizing agent and a noncoordinating, compatible anion represented by the formula:

$$(X^{e+})_d(A^{d-})_e \qquad (3)$$

wherein $X^{e+}$ is a cationic oxidizing agent having a charge of e+; e is 1, 2, or 3; $A^{d-}$ is a non-coordinating anion having the charge d−; and d is 1, 2, or 3. Examples of $X^{e+}$ include: ferrocenium, hydrocarbyl-substituted ferrocenium, $Ag^+$, or $Pb^{+2}$. Preferred embodiments of $A^{d-}$ are those anions previously defined with respect to the Bronsted acid containing activators, especially tetrakis(pentafluorophenyl)borate.

Activator Combinations

It is within the scope of this invention that metallocene compounds can be combined with one or more activators or activation methods described above. For example, a combination of activators have been described in U.S. Pat. Nos. 5,153,157; 5,453,410; European Publication No. EP 0 573 120 B1; PCT Publication Nos. WO 94/07928; and WO 95/14044. These documents all discuss the use of an alumoxane in combination with a stoichiometric activator.

Optional Cocatalysts

In addition to these alumoxane activator compounds, cocatalysts may be used. Aluminum alkyl or organometallic compounds which may be utilized as cocatalysts (or scavengers) include, for example, triethylaluminum, tri-isobutylaluminum, tri-n-hexylaluminum, tri-n-octylaluminum, diethyl aluminum chloride, dibutyl zinc, diethyl zinc, and the like.

Preferably, cocatalyst is present at a molar ratio of cocatalyst metal to transition metal of less than 100:1, preferably less than 50:1, preferably less than 15:1, preferably less than 10:1. In alternate embodiments, the cocatalyst is present at 0 wt %.

Other additives may also be used, as desired, such as one or more scavengers, promoters, modifiers, reducing agents, oxidizing agents, aluminum alkyls, or silanes.

Support Material

In preferred embodiments of the invention herein, the catalyst system comprises an inert support material. Preferably, the supported material is a porous support material, for example, talc, and inorganic oxides. Other support materials include zeolites, clays, organoclays, or any other organic or inorganic support material, or mixtures thereof.

Preferably, the support material is an inorganic oxide in a finely divided form. Suitable inorganic oxide materials for use in metallocene catalyst systems herein include Groups 2, 4, 13, and 14 metal oxides such as silica, alumina, and mixtures thereof. Other inorganic oxides that may be employed, either alone or in combination, with the silica or alumina are magnesia, titania, zirconia, and the like. Other suitable support materials, however, can be employed, for example, finely divided functionalized polyolefins such as finely divided polyethylene. Particularly useful supports include magnesia, titania, zirconia, montmorillonite, phyllosilicate, zeolites, talc, clays, and the like. Also, combinations of these support materials may be used, for example, silica-chromium, silica-alumina, silica-titania, and the like. Preferred support materials include $Al_2O_3$, $ZrO_2$, $SiO_2$, and combinations thereof, more preferably $SiO_2$, $Al_2O_3$, or $SiO_2/Al_2O_3$.

It is preferred that the support material, most preferably an inorganic oxide, has a surface area in the range of from about 10 $m^2/g$ to about 700 $m^2/g$, pore volume in the range of from about 0.1 cc/g to about 4.0 cc/g, and average particle size in the range of from about 5 μm to about 500 μm. More preferably, the surface area of the support material is in the range of from about 50 $m^2/g$ to about 500 $m^2/g$, pore volume of from about 0.5 cc/g to about 3.5 cc/g, and average particle size of from about 10 μm to about 200 μm. Most preferably, the surface area of the support material is in the range is from about 100 $m^2/g$ to about 400 $m^2/g$, pore volume from about 0.8 cc/g to about 3.0 cc/g, and average particle size is from about 5 μm to about 100 μm. The average pore size of the support material useful in the invention is in the range of from 10 to 1000 Å, preferably 50 to about 500 Å, and most preferably 75 to about 350 Å. In some embodiments, the support material is a high surface area, amorphous silica (surface area≥300 $m^2/gm$, pore volume≥1.65 $cm^3/gm$), and is marketed under the tradenames of DAVISON™ 952 or DAVISON™ 955 by the Davison Chemical Division of W. R. Grace and Company, are particularly useful. In other embodiments, DAVISON™ 948 is used.

In some embodiments of this invention, the support material may be dry, that is, free of absorbed water. Drying of the support material can be achieved by heating or calcining at about 100° C. to about 1000° C., preferably at least about 600° C. When the support material is silica, it is typically heated to at least 200° C., preferably about 200° C. to about 850° C., and most preferably at about 600° C.; and for a time of about 1 minute to about 100 hours, from about 12 hours to about 72 hours, or from about 24 hours to about 60 hours.

Methods of Making the Catalyst System

The catalyst system may be may be supported or unsupported. In embodiments where the catalyst system is unsupported, the metallocene compound may be activated with the activator in situ in the reactor, or may be pre-activated before addition to the reactor. Preactivation may involve contacting the metallocene compound with the activator, in solution, at a temperature in the range of from about 0° C. to about 100° C., preferably to about 25° C. to about 60° C., preferably at room temperature (25° C.) for a time period of from about 2 minutes to about 24 hours, preferably from about 0.5 hours to about 24 hours, from about 2 hours to about 16 hours, or from about 4 hours to about 8 hours. Such unsupported catalysts systems may be useful in solution polymerizations. Preferred activators for solution polymerizations are the stoichiometric activators, preferably ionic stoichiometric activators. Suitable solvents are materials in which all of the reagents used herein, i.e., the activator, and the metallocene compound, are at least partially soluble and which are liquid at reaction temperatures. Preferred solvents are alkanes, such as isopentane, hexane, n-heptane, octane, nonane, and decane, although a variety of other materials including cycloalkanes, such as cyclohexane, aromatics, such as benzene, toluene, and ethylbenzene, alone or in combination, may also be employed.

In embodiments where the catalyst system is a supported catalyst system, any method of supporting the metallocene compound and activator may be used. In some embodiments of this invention, the support material, typically having reactive surface groups, typically hydroxyl groups, is slurried in a non-polar solvent and the resulting slurry is contacted with a solution of an activator. The slurry mixture may be heated to about 0° C. to about 70° C., preferably to about 25° C. to about 60° C., preferably at room temperature (25° C.). Contact times typically range from about 0.5 hours to about 24 hours, from about 2 hours to about 16 hours, or from about 4 hours to about 8 hours.

Suitable non-polar solvents are materials in which all of the reagents used herein, i.e., the activator, and the metallocene compound, are at least partially soluble and which are liquid at reaction temperatures. Preferred non-polar solvents are alkanes, such as isopentane, hexane, n-heptane, octane, nonane, and decane, although a variety of other materials including cycloalkanes, such as cyclohexane, aromatics, such as benzene, toluene, and ethylbenzene, alone or in combination, may also be employed.

In particular embodiments of the invention, where the activator is an alumoxane, the support material is contacted with a solution of an alumoxane activator to form a supported alumoxane activator. The period of time for contact between the activator and the support material is as long as is necessary to titrate the reactive groups on the support material. To "titrate" is meant to react with available reactive groups on the surface of the support material, thereby reducing the surface hydroxyl groups by at least 80%, at least 90%, at least 95%, or at least 98%. The surface reactive group concentration may be determined based on the calcining temperature and the type of support material used. The support material calcining temperature affects the number of surface reactive groups on the support material available to react with the metallocene compound and an alumoxane activator: the higher the drying temperature, the lower the number of sites. For example, where the support material is silica which, prior to the use thereof in the first catalyst system synthesis step, is dehydrated by fluidizing it with nitrogen and heating at about 600° C. for about 16 hours, a surface hydroxyl group concentration of about 0.5 to about 0.9 millimoles per gram, preferably about 0.7 (mmols/gm) is typically achieved. Thus, the exact molar ratio of the activator to the surface reactive groups on the carrier will vary. Preferably, this is determined on a case-by-case basis to assure that only so much of the activator is added to the solution as will be deposited onto the support material without leaving excess of the activator in the solution.

The amount of the activator which will be deposited onto the support material without leaving excess in the solution can be determined in any conventional manner, e.g., by adding the activator to the slurry of the carrier in the solvent, while stirring the slurry, until the activator is detected as a solution in the solvent by any technique known in the art, such as by $^1$H NMR. For example, for the silica support material heated at about 600° C., the amount of the alumoxane activator added to the slurry is such that the molar ratio of Al to the hydroxyl groups (OH) on the silica is about 0.5:1 to about 4:1, preferably about 0.8:1 to about 3:1, more preferably about 0.9:1 to about 2:1, and most preferably about 1:1. The amount of Al in/on the silica may be determined by using ICPES (Inductively Coupled Plasma Emission Spectrometry), which is described in J. W. Olesik, "Inductively Coupled Plasma-Optical Emission Spectroscopy," in the Encyclopedia of Materials Characterization, C. R. Brundle, C. A. Evans, Jr. and S. Wilson, eds., Butterworth-Heinemann, Boston, Mass., 1992, pp. 633-644. In another embodiment, it is also possible to add such an amount of the activator which is in excess of that which will be deposited onto the support material, and then remove, e.g., by filtration and washing.

The supported activator is then slurried into an appropriate solvent, preferably a non-polar solvent. Preferred non-polar solvents are alkanes, such as isopentane, hexane, n-heptane, octane, nonane, and decane, although a variety of other materials including cycloalkanes, such as cyclohexane, aromatics, such as benzene, toluene, and ethylbenzene, may also be employed. The metallocene compound is added to the slurry mixture and heated to a temperature in the range of from 0° C. to about 70° C., preferably from about 25° C. to about 60° C., most preferably at 25° C. Contact times typically range from about 0.5 hours to about 24 hours, from about 2 hours to about 16 hours, or from about 4 hours to about 8 hours. The volatiles are removed to yield the supported catalyst system, preferably as a free-flowing solid.

In other embodiments, the metallocene compound is contacted with the alumoxane activator in solution, preferably in a solution of non-polar solvent, such as those above. The solution may be heated to 0° C. to about 70° C., preferably from about 25° C. to about 60° C., preferably at 25° C. Contact times may range from about 0.5 hours to about 24 hours, from about 2 hours to about 16 hours, or from about 4 hours to about 8 hours. The metallocene-activator solution is then contacted with the support material to form a slurry mixture. The slurry mixture may be heated to 0° C. to about 70° C., preferably from about 25° to about 60° C., preferably at 25° C. Contact times may range from about 0.5 hours to about 24 hours, from about 2 hours to about 16 hours, or from about 4 hours to about 8 hours. The volatiles are removed, preferably under vacuum, to yield the supported catalyst system, preferably as a free-flowing solid.

In some embodiments, the weight ratio of the zirconocene catalyst to the solid support material may be from about 10:1 to about 0.0001:1, from about 1:1 to about 0.001:1, or from about 0.1:1 to about 0.001:1. The weight ratio of the support material to the alumoxane activator compound may range from about 1:10 to about 100:1, from about 1:1 to about 100:1, or from about 1:1 to about 10:1.

In some embodiments, the supported catalyst system is suspended in a paraffinic agent, such as mineral oil, for easy addition to a reactor system, for example a gas phase polymerization system.

Polymerization Processes

This invention also relates to polymerization processes comprising: contacting one or more olefins with the metallocene catalyst system of the present invention under polymerization conditions; and obtaining an olefin polymer.

The metallocene catalyst systems described herein are useful in the polymerization of all types of olefins. This includes polymerization processes which produce homopolymers, copolymers, terpolymers, and the like, as well as block copolymers and impact copolymers.

Monomers useful herein include substituted or unsubstituted $C_2$ to $C_{40}$ olefins, preferably $C_2$ to $C_{20}$ olefins, preferably $C_2$ to $C_{12}$ olefins, preferably ethylene, propylene, butene, pentene, hexene, heptene, octene, nonene, decene, undecene, dodecene and isomers thereof, preferably alpha olefins. In a preferred embodiment of the invention, the monomer comprises propylene and optional comonomers comprising one or more ethylene or $C_4$ to $C_{40}$ olefins, preferably $C_4$ to $C_{20}$ olefins, or preferably $C_6$ to $C_{12}$ olefins. The $C_4$ to $C_{40}$ olefin monomers may be linear, branched, or cyclic. The $C_4$ to $C_{40}$ cyclic olefins may be strained or unstrained, monocyclic or polycyclic, and may optionally include heteroatoms and/or one or more functional groups. In another preferred embodiment, the monomer comprises ethylene and optional comonomers comprising one or more $C_3$ to $C_{40}$ olefins, preferably $C_4$ to $C_{20}$ olefins, or preferably $C_6$ to $C_{12}$ olefins. The $C_3$ to $C_{40}$ olefin monomers may be linear, branched, or cyclic. The $C_3$ to $C_{40}$ cyclic olefins may be strained or unstrained, monocyclic or polycyclic, and may optionally include heteroatoms and/or one or more functional groups.

Examples of $C_2$ to $C_{40}$ olefin monomers and optional comonomers include ethylene, propylene, butene, pentene, hexene, heptene, octene, nonene, decene, undecene, dodecene, norbornene, norbornadiene, dicyclopentadiene, cyclopentene, cycloheptene, cyclooctene, cyclooctadiene, cyclododecene, 7-oxanorbornene, 7-oxanorbornadiene, substituted derivatives thereof, and isomers thereof, preferably hexene, heptene, octene, nonene, decene, dodecene, cyclooctene, 1,5-cyclooctadiene, 1-hydroxy-4-cyclooctene, 1-acetoxy-4-cyclooctene, 5-methylcyclopentene, cyclopentene, dicyclopentadiene, norbornene, norbornadiene, and their respective homologs and derivatives, preferably norbornene, norbornadiene, and dicyclopentadiene. Preferably, the polymerization or copolymerization is carried out using olefins such as ethylene, propylene, 1-butene, 1-hexene, 4-methyl-1-pentene, and 1-octene, vinylcyclohexane, norbornene and norbornadiene. In particular, propylene and ethylene are polymerized.

In some embodiments, where butene is the comonomer, the butene source may be a mixed butene stream comprising various isomers of butene. The 1-butene monomers are expected to be preferentially consumed by the polymerization process. Use of such mixed butene streams will provide an economic benefit, as these mixed streams are often waste streams from refining processes, for example, $C_4$ raffinate streams, and can therefore be substantially less expensive than pure 1-butene.

Polymerization processes of this invention can be carried out in any manner known in the art, in solution, in suspension or in the gas phase, continuously or batchwise, or any combination thereof, in one or more steps. Homogeneous polymerization processes, slurry, and gas phase processes are preferred. (A homogeneous polymerization process is defined to be a process where at least 90 wt % of the product is soluble in the reaction media.) A bulk homogeneous process is particularly preferred. (A bulk process is defined to be a process where monomer concentration in all feeds to the reactor is 70 vol % or more.) Alternately, no solvent or diluent is present or added in the reaction medium (except for the small amounts used as the carrier for the catalyst system or other additives, or amounts typically found with the monomer; e.g., propane in propylene). In another embodiment, the process is a slurry process. As used herein the term "slurry polymerization process" means a polymerization process where a supported catalyst is employed and monomers are polymerized on the supported catalyst particles and at least 95 wt % of polymer products derived from the supported catalyst are in granular form as solid particles (not dissolved in the diluent).

If the polymerization is carried out as a suspension or solution polymerization, an inert solvent may be used, for example, the polymerization may be carried out in suitable diluents/solvents. Suitable diluents/solvents for polymerization include non-coordinating, inert liquids. Examples include straight and branched-chain hydrocarbons, such as isobutane, butane, pentane, isopentane, hexanes, isohexane, heptane, octane, dodecane, and mixtures thereof; cyclic and alicyclic hydrocarbons, such as cyclohexane, cycloheptane, methylcyclohexane, methylcycloheptane, and mixtures thereof, such as can be found commercially (Isopar™); perhalogenated hydrocarbons, such as perfluorinated $C_{4-10}$ alkanes, chlorobenzene, and aromatic and alkylsubstituted aromatic compounds, such as benzene, toluene, mesitylene, and xylene. Suitable solvents also include liquid olefins which may act as monomers or comonomers including ethylene, propylene, 1-butene, 1-hexene, 1-pentene, 3-methyl-1-pentene, 4-methyl-1-pentene, 1-octene, 1-decene, and mixtures thereof. In a preferred embodiment, aliphatic hydrocarbon solvents are used as the solvent, such as isobutane, butane, pentane, isopentane, hexanes, isohexane, heptane, octane, dodecane, and mixtures thereof; cyclic and alicyclic hydrocarbons, such as cyclohexane, cycloheptane, methylcyclohexane, methylcycloheptane, and mixtures thereof. In another embodiment, the solvent is not aromatic, preferably aromatics are present in the solvent at less than 1 wt %, preferably less than 0.5 wt %, preferably less than 0 wt %, based upon the weight of the solvents. It is also possible to use mineral spirit or a hydrogenated diesel oil fraction as a solvent. Toluene may also be used. The polymerization is preferably carried out in the liquid monomer(s). If inert solvents are used, the monomer(s) is (are) metered in gas or liquid form.

In a preferred embodiment, the feed concentration of the monomers and comonomers for the polymerization is 60 vol % solvent or less, preferably 40 vol % or less, or preferably 20 vol % or less, based on the total volume of the feedstream. Preferably, the polymerization is run in a bulk process.

Preferred polymerizations can be run at any temperature and/or pressure suitable to obtain the desired polymers. Typical temperatures and/or pressures include a temperature greater than 30° C., preferably greater than 50° C., preferably greater than 65° C., alternately less than 200° C., preferably less than 150° C., most preferably less than 140° C., and at a pressure in the range of from about 0.35 MPa to about 10 MPa, preferably from about 0.45 MPa to about 6 MPa, or preferably from about 0.5 MPa to about 4 MPa.

In a typical polymerization, the run time of the reaction is up to 300 minutes, preferably in the range of from about 5 to 250 minutes, or preferably from about 10 to 120 minutes.

If necessary, hydrogen is added as a molecular-weight regulator and/or in order to increase the activity. The overall pressure in the polymerization system usually is at least about 0.5 bar, preferably at least about 2 bar, most preferred at least about 5 bar. Pressures higher than about 100 bar, e.g., higher than about 80 bar and, in particular, higher than about 64 bar, are usually not preferred. In some embodiments, hydrogen is present in the polymerization reactor at a partial pressure of from 0.001 to 100 psig (0.007 to 690 kPa), preferably from 0.001 to 50 psig (0.007 to 345 kPa), preferably from 0.01 to 25 psig (0.07 to 172 kPa), more preferably 0.1 to 10 psig (0.7 to 70 kPa).

In an alternate embodiment, the productivity of the catalyst is at least 50 gpolymer/g (cat)/hour, preferably 500 or more gpolymer/g (cat)/hour, preferably 5000 or more gpolymer/g (cat)/hour, preferably 50,000 or more gpolymer/g (cat)/hour.

In an alternate embodiment, the conversion of olefin monomer is at least 10%, based upon polymer yield and the weight of the monomer entering the reaction zone, preferably 20% or more, preferably 30% or more, preferably 50% or more, preferably 80% or more. A "reaction zone", also referred to as a "polymerization zone", is a vessel where polymerization takes place, for example, a batch reactor. When multiple reactors are used in either series or parallel configuration, each reactor is considered as a separate polymerization zone. For a multi-stage polymerization in both a batch reactor and a continuous reactor, each polymerization stage is considered as a separate polymerization zone. In preferred embodiments, the polymerization occurs in one, two, three, four, or more reaction zones.

In a preferred embodiment, the catalyst system used in the polymerization comprises no more than one catalyst compound.

Other additives may also be used in the polymerization, as desired, such as one or more scavengers, promoters, modifiers, chain transfer agents (such as diethyl zinc), reducing agents, oxidizing agents, hydrogen, aluminum alkyls, or silanes.

Polyolefin Products

This invention also relates to polyolefins produced using the metallocene catalyst systems of this invention, particularly propylene and ethylene homopolymers and copolymers. In some embodiments, the invention relates to polyolefins produced using the metallocene catalyst systems of this invention, particularly polyethylene, having a density in the range of 0.916 to 0.940 g/cc, preferably in the range of from about 0.920 to 0.940 g/cc, preferably 0.920 to 0.935 g/cc.

In a preferred embodiment, the process described herein produces propylene homopolymers or propylene copolymers, such as propylene-ethylene and/or propylene-α-olefin (preferably $C_2$, and/or $C_4$ to $C_{20}$) copolymers (such as propylene-hexene copolymers, propylene-octene copolymers, or propylene-ethylene-hexene terpolymers) having a Mw/Mn of greater than 1 to 40 (preferably greater than 1 to 5). Preferably, copolymers of propylene have from 0 wt % to 25 wt % (alternately from 0.5 wt % to 20 wt %, alternately from 1 wt % to 15 wt %, preferably from 3 wt % to 10 wt %, preferably less than 1 wt %, preferably 0 wt %) of one or more of $C_2$ or $C_4$ to $C_{40}$ olefin comonomer (preferably ethylene or $C_4$ to $C_{20}$ or $C_4$ to $C_{12}$ alpha olefin comonomer, preferably ethylene, butene, hexene, octene, decene, dodecene, preferably ethylene, butene, hexene, or octene).

In another preferred embodiment, the process described herein produces ethylene homopolymers or copolymers, such as ethylene-propylene and/or ethylene-α-olefin (preferably $C_3$ and/or $C_4$ to $C_{20}$) copolymers (such as ethylene-hexene copolymers, ethylene-octene copolymers, or ethylene-propylene-hexene terpolymers) having a Mw/Mn of greater than 1 to 40 (preferably greater than 1 to 5). Preferably, copolymers of ethylene have from 0 wt % to 25 wt % (alternately from 0.5 wt % to 20 wt %, alternately from 1 wt % to 15 wt %, preferably from 3 wt % to 10 wt %, preferably less than 1 wt %, preferably 0 wt %) of one or more of $C_3$ to $C_{40}$ olefin comonomer (preferably propylene or $C_3$ to $C_{20}$ or $C_4$ to $C_{12}$ alpha olefin comonomer, preferably propylene, butene, hexene, octene, decene, dodecene, preferably ethylene, butene, hexene, and octene).

Uses of Polyolefins

Polyolefins prepared using the processes described herein find uses in all applications including fibers, injection molded parts, films, pipes, and wire and cable applications. Examples include carpet fibers and primary and secondary carpet backing; slit tape applications such as tarpaulins, erosion abatement screens, sand bags, fertilizer and feed bags, swimming pool covers, intermediate bulk container (IBC) bags; nonwoven applications for spun-bonded, melt blown and thermobonded fibers; carded web applications such as disposable diaper liners, feminine hygiene products, tarpaulins and tent fabrics, and hospital garments; apparel applications such as socks, T-shirts, undergarments, bicycle shorts, sweat bands, football undershirts, hiking socks, and other outdoor sporting apparel; cordage applications such as mooring and towing lines and rope; netting applications such as safety fences and geogrids for soil stabilization; injection molded applications such as appliance parts in automatic dishwashers and clothes washers, hand tools, and kitchen appliances; consumer product applications such as outdoor furniture, luggage, infant car seats, ice coolers, yard equipment; medical applications such as disposable syringes and other hospital and laboratory devices; rigid packaging made by injection molding, blow molding, or thermoforming such as margarine tubs, yogurt containers and closures, commercial bottles, and ready-to-eat food containers; transportation applications such as automotive interior trim, instrument panels, bumper fascia, grills and external trim parts, battery cases; film applications such as snack packages and other food packaging and film labels, packing tapes and pressure sensitive labels; wire and cable applications such as wire insulation.

The polyolefins described herein may be used by themselves or blended with one or more additional polymers. In another embodiment, the polyolefin (preferably propylene or ethylene homopolymer or copolymer) produced herein is combined with one or more additional polymers prior to being formed into a film, molded part, or other article. Useful additional polymers include polyethylene, isotactic polypropylene, highly isotactic polypropylene, syndiotactic polypropylene, random copolymer of propylene and ethylene, and/or butene, and/or hexene, polybutene, ethylene vinyl acetate, LDPE (low density polyethylene), LLDPE (linear low density polyethylene), HDPE (high density polyethylene), ethylene vinyl acetate, ethylene methyl acrylate, copolymers of acrylic acid, polymethylmethacrylate or any other polymers polymerizable by a high-pressure free radical process, polyvinylchloride, polybutene-1, isotactic polybutene, ABS resins, ethylene-propylene rubber (EPR), vulcanized EPR, EPDM (ethylene-propylene-diene monomer rubber), block copolymer, styrenic block copolymers, polyamides, polycarbonates, PET (polyethylene terephthalate) resins, cross linked polyethylene, copolymers of ethylene and vinyl alcohol (EVOH), polymers of aromatic monomers such as polystyrene, poly-1 esters, polyacetal, polyvinylidine fluoride, polyethylene glycols, and/or polyisobutylene.

In other embodiments, this invention relates to:

1. A bridged metallocene compound represented by the following formula:

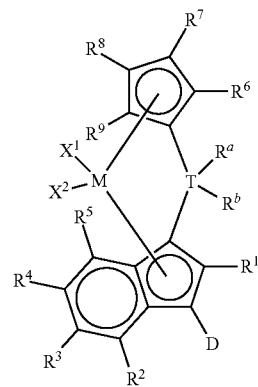

wherein:
M is a group 4 metal (preferably M is zirconium or hafnium, more preferably zirconium);
T is a group 14 atom (preferably silicon or germanium, more preferably silicon);
D is a substituted or unsubstituted aromatic group (preferably D is selected from the group consisting of substituted or unsubstituted phenyl, naphthyl, biphenyl, cyclopropenyl, tropylium, cyclooctatetraenyl, furanyl, pyridinyl, borabenzyl, thiophenyl, azolyl, oxazolyl, and imidazolyl; more preferably D is selected from the group consisting of substituted or unsubstituted phenyl, biphenyl, naphthyl, cyclopropenyl, furanyl, pyridinyl, thiophenyl, azolyl, oxazolyl, and imidazolyl);
$R^a$ and $R^b$ are independently, hydrogen, halogen, or a $C_1$ to $C_{20}$ substituted or unsubstituted hydrocarbyl, and $R^a$ and $R^b$ can form a cyclic structure including substituted or unsubstituted aromatic, partially saturated, or saturated cyclic or fused ring system (preferably each $R^a$ and $R^b$ is independently selected from the group consisting of halides, $C_1$ to $C_{20}$ substituted or unsubstituted hydrocarbyl groups, and cyclic structures where $R^a$ and $R^b$ form a heterocyclopentyl, heterocyclobutyl, or heterocyclohexyl structure with T being the heteroatom; more preferably each $R^a$ and $R^b$ is independently selected from the group consisting of chlorides, fluorides, methyl and ethyl groups); more preferably each $R^a$ and $R^b$ is, independently, selected from the group consisting of chlorides, fluorides, methyl and ethyl groups);
each $X^1$ and $X^2$ is independently selected from the group consisting of $C_1$ to $C_{20}$ substituted or unsubstituted hydrocarbyl groups, hydrides, amides, amines, alkoxides, sulfides, phosphides, halides, dienes, phosphines, and ethers; and $X^1$ and $X^2$ can form a cyclic structure including aromatic, partially saturated, or saturated cyclic or fused ring system; more preferably, each $X^1$ and $X^2$ is independently selected from the group consisting of chlorides, fluorides, methyl, and ethyl groups;
each of $R^1$, $R^2$, $R^3$, $R^4$, and $R^5$ is, independently, hydrogen, halide, alkoxide or a $C_1$ to $C_{40}$ substituted or unsubstituted hydrocarbyl group, and any of adjacent $R^2$, $R^3$, $R^4$, and/or $R^5$ groups may form a fused ring or multicenter fused ring systems, where the rings may be substituted or unsubstituted, and may be aromatic, partially unsaturated, or unsaturated (preferably, each of $R^1$, $R^2$, $R^3$, $R^4$, and $R^5$ is, independently, a $C_1$ to $C_{20}$ substituted or unsubstituted hydrocarbyl group); and
each of $R^6$, $R^7$, $R^8$, and $R^9$ is, each independently, hydrogen or a $C_1$ to $C_{40}$ substituted or unsubstituted hydrocarbyl group (preferably each of $R^6$, $R^7$, $R^8$, and $R^9$ is, independently, a $C_1$ to $C_{40}$ substituted or unsubstituted hydrocarbyl group; more preferably each of $R^6$, $R^7$, $R^8$, and $R^9$ is, independently, a $C_1$ to $C_{20}$ substituted or unsubstituted hydrocarbyl group;

more preferably, each of $R^6$, $R^7$, $R^8$, and $R^9$ is, independently, selected from the group consisting of methyl, ethyl, propyl, isopropyl, n-butyl, sec-butyl, t-butyl, pentyl, hexyl, heptyl, octyl, decyl, and undecyl groups; even more preferably, each of $R^6$, $R^7$, $R^8$, and $R^9$ is, independently, selected from the group consisting of methyl, ethyl, and n-propyl groups;

preferably, adjacent $R^6$, $R^7$, $R^8$, and/or $R^9$ groups fuse together with the cyclopentadienyl group to form a substituted or unsubstituted fluorene);

further provided that at least two of $R^6$, $R^7$, $R^8$, and $R^9$ are $C_1$ to $C_{40}$ substituted or unsubstituted hydrocarbyl groups; and (preferably, the metallocene compound is asymmetric, which is defined to mean that the groups that are bridged by the $TR^aR^b$ bridge do not have the same number of fused aromatic rings, for example, the metallocene compound is not a bis-indenyl compound. Instead, the metallocene compound may be a cyclopentadienyl-indenyl compound, a cyclopentadienyl-fluorenyl compound, or an indenyl-fluorenyl compound).

2. The metallocene compounds of paragraphs 1, represented by the formula:

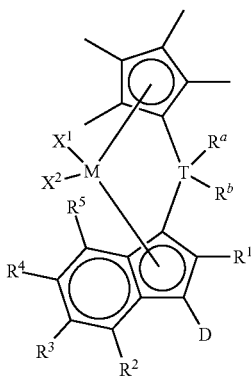

wherein $R^1$, $R^2$, $R^3$, $R^4$, $R^5$, $R^a$, $R^b$, $X^1$, $X^2$, T, D, and M are as defined in paragraph 1.

3. The metallocene compounds of paragraphs 1 and 2, represented by the following structure:

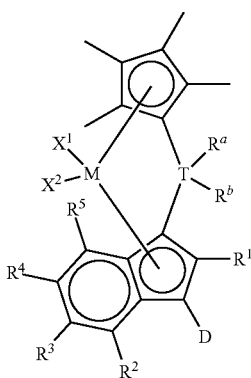

wherein $R^1$, $R^2$, $R^3$, $R^4$, $R^5$, $R^a$, $R^b$, $X^1$, $X^2$, T, and M are as defined above in paragraph 1.

4. The metallocene compounds of paragraphs 1 to 3, represented by the following structure:

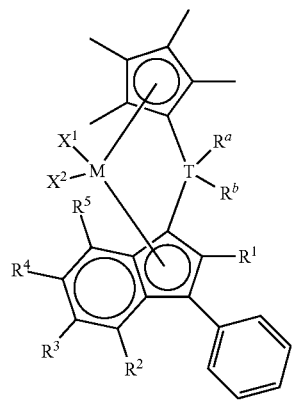

wherein $R^1$, $R^2$, $R^3$, $R^4$, $R^5$, $R^a$, $R^b$, $X^1$, $X^2$, T, and M are as defined above in paragraph 1.

5. The metallocene compounds of paragraph 1, including:
dimethylsilylene(3-phenyl-1-indenyl)(2,3,4,5-tetramethyl-1-cyclopentadienyl)zirconium dichloride;
dimethylsilylene(3-phenyl-1-indenyl)(2,5-dimethyl-1-cyclopentadienyl)zirconium dichloride;
dimethylsilylene(3-phenyl-1-indenyl)(3,4-dimethyl-1-cyclopentadienyl)zirconium dichloride;
dimethylsilylene(3-phenyl-1-indenyl)(2,3,4,5-tetraethyl-1-cyclopentadienyl)zirconium dichloride;
dimethylsilylene(3-phenyl-1-indenyl)(2,3,4,5-tetrapropyl-1-cyclopentadienyl)zirconium dichloride;
dimethylsilylene(3-phenyl-1-indenyl)(9-fluorenyl)zirconium dichloride;
dimethylsilylene(3-phenyl-1-indenyl)(2,7-dimethyl-9-fluorenyl)zirconium dichloride;
dimethylsilylene(3-phenyl-1-indenyl)(2,7-di-t-butyl-9-fluorenyl)zirconium dichloride;
dimethylsilylene(3-phenyl-1-indenyl)(3,6-dimethyl-9-fluorenyl)zirconium dichloride;
dimethylsilylene(3-phenyl-1-indenyl)(3,6-di-t-butyl-9-fluorenyl)zirconium dichloride;
dimethylsilylene(3-phenyl-1-indenyl)(4,7-dimethyl-9-fluorenyl)zirconium dichloride; diethylsilylene(3-phenyl-1-indenyl)(2,3,4,5-tetramethyl-1-cyclopentadienyl)zirconium dichloride;
dipropylsilylene(3-phenyl-1-indenyl)(2,3,4,5-tetramethyl-1-cyclopentadienyl)zirconium dichloride;
dibutylsilylene(3-phenyl-1-indenyl)(2,3,4,5-tetramethyl-1-cyclopentadienyl)zirconium dichloride;
diphenylsilylene(3-phenyl-1-indenyl)(2,3,4,5-tetramethyl-1-cyclopentadienyl)zirconium dichloride;
silacyclobutylidene(3-phenyl-1-indenyl)(2,3,4,5-tetramethyl-1-cyclopentadienyl)zirconium dichloride;
silacyclopentylidene(3-phenyl-1-indenyl)(2,3,4,5-tetramethyl-1-cyclopentadienyl)zirconium dichloride;
silacyclohexylidene(3-phenyl-1-indenyl)(2,3,4,5-tetramethyl-1-cyclopentadienyl)zirconium dichloride;
dimethylgermylene(3-phenyl-1-indenyl)(2,3,4,5-tetramethyl-1-cyclopentadienyl)zirconium dichloride;
diethylgermylene(3-phenyl-1-indenyl)(2,3,4,5-tetramethyl-1-cyclopentadienyl)zirconium dichloride;
dipropylgermylene(3-phenyl-1-indenyl)(2,3,4,5-tetramethyl-1-cyclopentadienyl)zirconium dichloride;
dibutylgermylene(3-phenyl-1-indenyl)(2,3,4,5-tetramethyl-1-cyclopentadienyl)zirconium dichloride;
diphenylgermylene(3-phenyl-1-indenyl)(2,3,4,5-tetramethyl-1-cyclopentadienyl)zirconium dichloride;

isopropylidene(3-phenyl-1-indenyl)(2,3,4,5-tetramethyl-1-cyclopentadienyl)zirconium dichloride;
diphenylmethylene(3-phenyl-1-indenyl)(2,3,4,5-tetramethyl-1-cyclopentadienyl)zirconium dichloride;
dimethylsilylene(2-methyl-3-phenyl-1-indenyl)(2,3,4,5-tetramethyl-1-cyclopentadienyl)zirconium dichloride;
dimethylsilylene(2-ethyl-3-phenyl-1-indenyl)(2,3,4,5-tetramethyl-1-cyclopentadienyl)zirconium dichloride;
dimethylsilylene(2-propyl-3-phenyl-1-indenyl)(2,3,4,5-tetramethyl-1-cyclopentadienyl)zirconium dichloride;
dimethylsilylene(2-isopropyl-3-phenyl-1-indenyl)(2,3,4,5-tetramethyl-1-cyclopentadienyl)zirconium dichloride;
dimethylsilylene(4-methyl-3-phenyl-1-indenyl)(2,3,4,5-tetramethyl-1-cyclopentadienyl)zirconium dichloride;
dimethylsilylene(4,7-dimethyl-3-phenyl-1-indenyl)(2,3,4,5-tetramethyl-1-cyclopentadienyl)zirconium dichloride;
dimethylsilylene(5,6-dimethyl-3-phenyl-1-indenyl)(2,3,4,5-tetramethyl-1-cyclopentadienyl)zirconium dichloride;
dimethylsilylene(2,4-dimethyl-3-phenyl-1-indenyl)(2,3,4,5-tetramethyl-1-cyclopentadienyl)zirconium dichloride;
dimethylsilylene(2,6-dimethyl-3-phenyl-1-indenyl)(2,3,4,5-tetramethyl-1-cyclopentadienyl)zirconium dichloride;
dimethylsilylene(3-phenyl-2,4,6-trimethyl-1-indenyl)(2,3,4,5-tetramethyl-1-cyclopentadienyl)zirconium dichloride;
dimethylsilylene(3-phenyl-2,4,7-trimethyl-1-indenyl)(2,3,4,5-tetramethyl-1-cyclopentadienyl)zirconium dichloride;
dimethylsilylene(3-phenyl-2,5,6-trimethyl-1-indenyl)(2,3,4,5-tetramethyl-1-cyclopentadienyl)zirconium dichloride;
dimethylsilylene(3-phenyl-4,5,6,7-tetramethyl-1-indenyl)(2,3,4,5-tetramethyl-1-cyclopentadienyl)zirconium dichloride;
dimethylsilylene(2,4,5,6,7-pentamethyl-3-phenyl-1-indenyl)(2,3,4,5-tetramethyl-1-cyclopentadienyl)zirconium dichloride;
dimethylsilylene(6-chloro-3-phenyl-1-indenyl)(2,3,4,5-tetramethyl-1-cyclopentadienyl)zirconium dichloride;
dimethylsilylene(7-chloro-3-phenyl-1-indenyl)(2,3,4,5-tetramethyl-1-cyclopentadienyl)zirconium dichloride;
dimethylsilylene(4,6-dichloro-3-phenyl-1-indenyl)(2,3,4,5-tetramethyl-1-cyclopentadienyl)zirconium dichloride;
dimethylsilylene(5,7-dichloro-2-methyl-3-phenyl-1-indenyl)(2,3,4,5-tetramethyl-1-cyclopentadienyl)zirconium dichloride;
dimethylsilylene(2-butyl-7-chloro-3-phenyl-1-indenyl)(2,3,4,5-tetramethyl-1-cyclopentadienyl)zirconium dichloride;
dimethylsilylene(7-chloro-3-phenyl-2-propyl-1-indenyl)(2,3,4,5-tetramethyl-1-cyclopentadienyl)zirconium dichloride;
dimethylsilylene(7-chloro-2-ethyl-3-phenyl-1-indenyl)(2,3,4,5-tetramethyl-1-cyclopentadienyl)zirconium dichloride;
dimethylsilylene(5-fluoro-3-phenyl-1-indenyl)(2,3,4,5-tetramethyl-1-cyclopentadienyl)zirconium dichloride;
dimethylsilylene(5,7-difluoro-3-phenyl-1-indenyl)(2,3,4,5-tetramethyl-1-cyclopentadienyl)zirconium dichloride;
dimethylsilylene(4,6-difluoro-3-phenyl-1-indenyl)(2,3,4,5-tetramethyl-1-cyclopentadienyl)zirconium dichloride;
dimethylsilylene(5,7-difluoro-2-methyl-3-phenyl-1-indenyl)(2,3,4,5-tetramethyl-1-cyclopentadienyl)zirconium dichloride;
dimethylsilylene(3-phenyl-1,5,6,7-tetrahydro-s-1-indacenyl)(2,3,4,5-tetramethyl-1-cyclopentadienyl)zirconium dichloride;
dimethylsilylene(2-methyl-3-phenyl-1,5,6,7-tetrahydro-s-1-indacenyl)(2,3,4,5-tetramethyl-1-cyclopentadienyl)zirconium dichloride;
dimethylsilylene(6,6-dimethyl-3-phenyl-1,5,6,7-tetrahydro-s-1-indacenyl)(2,3,4,5-tetramethyl-1-cyclopentadienyl)zirconium dichloride;
dimethylsilylene(3-phenyl-2,6,6-trimethyl-1,5,6,7-tetrahydro-s-1-indacenyl)(2,3,4,5-tetramethyl-1-cyclopentadienyl)zirconium dichloride;
dimethylsilylene(3-pheny-5,5,8,8-tetramethyl-5,6,7,8-tetrahydrobenz[f]-1-indenyl)(2,3,4,5-tetramethyl-1-cyclopentadienyl)zirconium dichloride;
dimethylsilylene(3-phenylbenz[f]-1-indenyl)(2,3,4,5-tetramethyl-1-cyclopentadienyl)zirconium dichloride;
dimethylsilylene(2-methyl-3-phenylbenz[f]-1-indenyl)(2,3,4,5-tetramethyl-1-cyclopentadienyl)zirconium dichloride;
dimethylsilylene(2,5,5,8,8-pentamethyl-3-phenyl-5,6,7,8-tetrahydrobenz[f]-1-indenyl)(2,3,4,5-tetramethyl-1-cyclopentadienyl)zirconium dichloride;
dimethylsilylene(3-phenylbenz[e]-1-indenyl)(2,3,4,5-tetramethyl-1-cyclopentadienyl)zirconium dichloride;
dimethylsilylene(2-methyl-3-phenylbenz[e]-1-indenyl)(2,3,4,5-tetramethyl-1-cyclopentadienyl)zirconium dichloride;
dimethylsilylene(3-(4-methylphenyl)-1-indenyl)(2,3,4,5-tetramethyl-1-cyclopentadienyl)zirconium dichloride;
dimethylsilylene(3-(3,5-dimethylphenyl)-1-indenyl)(2,3,4,5-tetramethyl-1-cyclopentadienyl)zirconium dichloride;
dimethylsilylene(3-(2,6-dimethylphenyl)-1-indenyl)(2,3,4,5-tetramethyl-1-cyclopentadienyl)zirconium dichloride;
dimethylsilylene(3-(2,4-dimethylphenyl)-1-indenyl)(2,3,4,5-tetramethyl-1-cyclopentadienyl)zirconium dichloride;
dimethylsilylene(3-(3,4-dimethylphenyl)-1-indenyl)(2,3,4,5-tetramethyl-1-cyclopentadienyl)zirconium dichloride;
dimethylsilylene(3-(2,3-dimethylphenyl)-1-indenyl)(2,3,4,5-tetramethyl-1-cyclopentadienyl)zirconium dichloride;
dimethylsilylene(3-(2,5-dimethylphenyl)-1-indenyl)(2,3,4,5-tetramethyl-1-cyclopentadienyl)zirconium dichloride;
dimethylsilylene(3-(2,4,6-trimethylphenyl)-1-indenyl)(2,3,4,5-tetramethyl-1-cyclopentadienyl)zirconium dichloride;
dimethylsilylene(3-(2,3,4-trimethylphenyl)-1-indenyl)(2,3,4,5-tetramethyl-1-cyclopentadienyl)zirconium dichloride;
dimethylsilylene(3-(3,4,5-trimethylphenyl)-1-indenyl)(2,3,4,5-tetramethyl-1-cyclopentadienyl)zirconium dichloride;
dimethylsilylene(3-(2,3,5-trimethylphenyl)-1-indenyl)(2,3,4,5-tetramethyl-1-cyclopentadienyl)zirconium dichloride;
dimethylsilylene(3-(2,3,6-trimethylphenyl)-1-indenyl)(2,3,4,5-tetramethyl-1-cyclopentadienyl)zirconium dichloride;
dimethylsilylene(3-(2,4,5-trimethylphenyl)-1-indenyl)(2,3,4,5-tetramethyl-1-cyclopentadienyl)zirconium dichloride;
dimethylsilylene(3-(2,3,4,5-tetramethylphenyl)-1-indenyl)(2,3,4,5-tetramethyl-1-cyclopentadienyl)zirconium dichloride;
dimethylsilylene(3-(2,3,4,5-tetramethylphenyl)-1-indenyl)(2,3,4,5-tetramethyl-1-cyclopentadienyl)zirconium dichloride;
dimethylsilylene(3-(2,3,4,6-tetramethylphenyl)-1-indenyl)(2,3,4,5-tetramethyl-1-cyclopentadienyl)zirconium dichloride;
dimethylsilylene(3-(2,3,5,6-tetramethylphenyl)-1-indenyl)(2,3,4,5-tetramethyl-1-cyclopentadienyl)zirconium dichloride;
dimethylsilylene(3-(2,3,4,5,6-pentamethylphenyl)-1-indenyl)(2,3,4,5-tetramethyl-1-cyclopentadienyl)zirconium dichloride;
dimethylsilylene(3-(2-methylphenyl)-1-indenyl)(2,3,4,5-tetramethyl-1-cyclopentadienyl)zirconium dichloride;
dimethylsilylene(3-(2-ethylphenyl)-1-indenyl)(2,3,4,5-tetramethyl-1-cyclopentadienyl)zirconium dichloride;
dimethylsilylene(3-(2-propylphenyl)-1-indenyl)(2,3,4,5-tetramethyl-1-cyclopentadienyl)zirconium dichloride;

dimethylsilylene(3-(2-butylphenyl)-1-indenyl)(2,3,4,5-tetramethyl-1-cyclopentadienyl)zirconium dichloride;
dimethylsilylene(3-(3-methylphenyl)-1-indenyl)(2,3,4,5-tetramethyl-1-cyclopentadienyl)zirconium dichloride;
dimethylsilylene(3-(3-ethylphenyl)-1-indenyl)(2,3,4,5-tetramethyl-1-cyclopentadienyl)zirconium dichloride;
dimethylsilylene(3-(3-propylphenyl)-1-indenyl)(2,3,4,5-tetramethyl-1-cyclopentadienyl)zirconium dichloride;
dimethylsilylene(3-(3-butylphenyl)-1-indenyl)(2,3,4,5-tetramethyl-1-cyclopentadienyl)zirconium dichloride;
dimethylsilylene(3-(3-t-butylphenyl)-1-indenyl)(2,3,4,5-tetramethyl-1-cyclopentadienyl)zirconium dichloride;
dimethylsilylene(3-(4-methylphenyl)-1-indenyl)(2,3,4,5-tetramethyl-1-cyclopentadienyl)zirconium dichloride;
dimethylsilylene(3-(4-ethylphenyl)-1-indenyl)(2,3,4,5-tetramethyl-1-cyclopentadienyl)zirconium dichloride;
dimethylsilylene(3-(4-propylphenyl)-1-indenyl)(2,3,4,5-tetramethyl-1-cyclopentadienyl)zirconium dichloride;
dimethylsilylene(3-(4-butylphenyl)-1-indenyl)(2,3,4,5-tetramethyl-1-cyclopentadienyl)zirconium dichloride;
dimethylsilylene(3-(4-t-butylphenyl)-1-indenyl)(2,3,4,5-tetramethyl-1-cyclopentadienyl)zirconium dichloride;
dimethylsilylene(3-(4-biphenyl)-1-indenyl)(2,3,4,5-tetramethyl-1-cyclopentadienyl)zirconium dichloride;
dimethylsilylene(3-(3-biphenyl)-1-indenyl)(2,3,4,5-tetramethyl-1-cyclopentadienyl)zirconium dichloride;
dimethylsilylene(3-(2-biphenyl)-1-indenyl)(2,3,4,5-tetramethyl-1-cyclopentadienyl)zirconium dichloride;
dimethylsilylene(3-(3,5-diphenylphenyl)-1-indenyl)(2,3,4,5-tetramethyl-1-cyclopentadienyl)zirconium dichloride;
dimethylsilylene(3-(3,5-di-t-butylphenyl)-1-indenyl)(2,3,4,5-tetramethyl-1-cyclopentadienyl)zirconium dichloride;
dimethylsilylene(3-(2-fluorophenyl)-1-indenyl)(2,3,4,5-tetramethyl-1-cyclopentadienyl)zirconium dichloride;
dimethylsilylene(3-(3-fluorophenyl)-1-indenyl)(2,3,4,5-tetramethyl-1-cyclopentadienyl)zirconium dichloride;
dimethylsilylene(3-(4-fluorophenyl)-1-indenyl)(2,3,4,5-tetramethyl-1-cyclopentadienyl)zirconium dichloride;
dimethylsilylene(3-(2,3-difluorophenyl)-1-indenyl)(2,3,4,5-tetramethyl-1-cyclopentadienyl)zirconium dichloride;
dimethylsilylene(3-(2,4-difluorophenyl)-1-indenyl)(2,3,4,5-tetramethyl-1-cyclopentadienyl)zirconium dichloride;
dimethylsilylene(3-(2,5-difluorophenyl)-1-indenyl)(2,3,4,5-tetramethyl-1-cyclopentadienyl)zirconium dichloride;
dimethylsilylene(3-(2,6-difluorophenyl)-1-indenyl)(2,3,4,5-tetramethyl-1-cyclopentadienyl)zirconium dichloride;
dimethylsilylene(3-(3,4-difluorophenyl)-1-indenyl)(2,3,4,5-tetramethyl-1-cyclopentadienyl)zirconium dichloride;
dimethylsilylene(3-(3,5-difluorophenyl)-1-indenyl)(2,3,4,5-tetramethyl-1-cyclopentadienyl)zirconium dichloride;
dimethylsilylene(3-(2,3,4-trifluorophenyl)-1-indenyl)(2,3,4,5-tetramethyl-1-cyclopentadienyl)zirconium dichloride;
dimethylsilylene(3-(2,3,5-trifluorophenyl)-1-indenyl)(2,3,4,5-tetramethyl-1-cyclopentadienyl)zirconium dichloride;
dimethylsilylene(3-(2,3,6-trifluorophenyl)-1-indenyl)(2,3,4,5-tetramethyl-1-cyclopentadienyl)zirconium dichloride;
dimethylsilylene(3-(2,4,5-trifluorophenyl)-1-indenyl)(2,3,4,5-tetramethyl-1-cyclopentadienyl)zirconium dichloride;
dimethylsilylene(3-(2,4,6-trifluorophenyl)-1-indenyl)(2,3,4,5-tetramethyl-1-cyclopentadienyl)zirconium dichloride;
dimethylsilylene(3-(3,4,5-trifluorophenyl)-1-indenyl)(2,3,4,5-tetramethyl-1-cyclopentadienyl)zirconium dichloride;
dimethylsilylene(3-(2,3,4,5-tetrafluorophenyl)-1-indenyl)(2,3,4,5-tetramethyl-1-cyclopentadienyl)zirconium dichloride;
dimethylsilylene(3-(2,3,4,6-tetrafluorophenyl)-1-indenyl)(2,3,4,5-tetramethyl-1-cyclopentadienyl)zirconium dichloride;
dimethylsilylene(3-(2,3,5,6-tetrafluorophenyl)-1-indenyl)(2,3,4,5-tetramethyl-1-cyclopentadienyl)zirconium dichloride;
dimethylsilylene(3-(pentafluorophenyl)-1-indenyl)(2,3,4,5-tetramethyl-1-cyclopentadienyl)zirconium dichloride;
dimethylsilylene(3-(2-chlorophenyl)-1-indenyl)(2,3,4,5-tetramethyl-1-cyclopentadienyl)zirconium dichloride;
dimethylsilylene(3-(3-chlorophenyl)-1-indenyl)(2,3,4,5-tetramethyl-1-cyclopentadienyl)zirconium dichloride;
dimethylsilylene(3-(4-chlorophenyl)-1-indenyl)(2,3,4,5-tetramethyl-1-cyclopentadienyl)zirconium dichloride;
dimethylsilylene(3-(2,6-dichlorophenyl)-1-indenyl)(2,3,4,5-tetramethyl-1-cyclopentadienyl)zirconium dichloride;
dimethylsilylene(3-(3,5-dichlorophenyl)-1-indenyl)(2,3,4,5-tetramethyl-1-cyclopentadienyl)zirconium dichloride;
dimethylsilylene(3-(2,4,6-trichlorophenyl)-1-indenyl)(2,3,4,5-tetramethyl-1-cyclopentadienyl)zirconium dichloride;
dimethylsilylene(3-(2-trifluoromethylphenyl)-1-indenyl)(2,3,4,5-tetramethyl-1-cyclopentadienyl)zirconium dichloride;
dimethylsilylene(3-(3-trifluoromethylphenyl)-1-indenyl)(2,3,4,5-tetramethyl-1-cyclopentadienyl)zirconium dichloride;
dimethylsilylene(3-(4-trifluoromethylphenyl)-1-indenyl)(2,3,4,5-tetramethyl-1-cyclopentadienyl)zirconium dichloride;
dimethylsilylene(3-(3,5-bis(trifluoromethy)lphenyl)-1-indenyl)(2,3,4,5-tetramethyl-1-cyclopentadienyl)zirconium dichloride;
dimethylsilylene(3-(2-methoxyphenyl)-1-indenyl)(2,3,4,5-tetramethyl-1-cyclopentadienyl)zirconium dichloride;
dimethylsilylene(3-(3-methoxyphenyl)-1-indenyl)(2,3,4,5-tetramethyl-1-cyclopentadienyl)zirconium dichloride;
dimethylsilylene(3-(4-methoxyphenyl)-1-indenyl)(2,3,4,5-tetramethyl-1-cyclopentadienyl)zirconium dichloride;
dimethylsilylene(3-(2,6-dimethoxyphenyl)-1-indenyl)(2,3,4,5-tetramethyl-1-cyclopentadienyl)zirconium dichloride;
dimethylsilylene(3-(3,5-dimethoxyphenyl)-1-indenyl)(2,3,4,5-tetramethyl-1-cyclopentadienyl)zirconium dichloride;
dimethylsilylene(3-(2,4,6-trimethoxyphenyl)-1-indenyl)(2,3,4,5-tetramethyl-1-cyclopentadienyl)zirconium dichloride;
dimethylsilylene(3-(1-naphthyl)-1-indenyl)(2,3,4,5-tetramethyl-1-cyclopentadienyl)zirconium dichloride;
dimethylsilylene(3-(2-naphthyl)-1-indenyl)(2,3,4,5-tetramethyl-1-cyclopentadienyl)zirconium dichloride;
dimethylsilylene(2-methyl-3-(2-naphthyl)-1-indenyl)(2,3,4,5-tetramethyl-1-cyclopentadienyl)zirconium dichloride;
dimethylsilylene(3-(1-anthryl)-1-indenyl)(2,3,4,5-tetramethyl-1-cyclopentadienyl)zirconium dichloride;
dimethylsilylene(3-(2-anthryl)-1-indenyl)(2,3,4,5-tetramethyl-1-cyclopentadienyl)zirconium dichloride;
dimethylsilylene(3-(9-anthryl)-1-indenyl)(2,3,4,5-tetramethyl-1-cyclopentadienyl)zirconium dichloride;
dimethylsilylene(3-(9-phenanthryl)-1-indenyl)(2,3,4,5-tetramethyl-1-cyclopentadienyl)zirconium dichloride;
dimethylsilylene(3-(2-furanyl)-1-indenyl)(2,3,4,5-tetramethyl-1-cyclopentadienyl)zirconium dichloride;
dimethylsilylene(3-(2-furanyl)-2-methyl-1-indenyl)(2,3,4,5-tetramethyl-1-cyclopentadienyl)zirconium dichloride;
dimethylsilylene(3-(3-furanyl)-1-indenyl)(2,3,4,5-tetramethyl-1-cyclopentadienyl)zirconium dichloride;
dimethylsilylene(3-(3-furanyl)-2-methyl-1-indenyl)(2,3,4,5-tetramethyl-1-cyclopentadienyl)zirconium dichloride;

dimethylsilylene(3-(2-thiophenyl)-1-indenyl)(2,3,4,5-tetramethyl-1-cyclopentadienyl)zirconium dichloride;
dimethylsilylene(2-methyl-3-(2-thiophenyl)-1-indenyl)(2,3,4,5-tetramethyl-1-cyclopentadienyl)zirconium dichloride;
dimethylsilylene(3-(3-thiophenyl)-1-indenyl)(2,3,4,5-tetramethyl-1-cyclopentadienyl)zirconium dichloride;
dimethylsilylene(2-methyl-3-(3-thiophenyl)-1-indenyl)(2,3,4,5-tetramethyl-1-cyclopentadienyl)zirconium dichloride;
dimethylsilylene(3-(2-pyridyl)-1-indenyl)(2,3,4,5-tetramethyl-1-cyclopentadienyl)zirconium dichloride;
dimethylsilylene(2-methyl-3-(2-pyridyl)-1-indenyl)(2,3,4,5-tetramethyl-1-cyclopentadienyl)zirconium dichloride;
dimethylsilylene(3-(3-pyridyl)-1-indenyl)(2,3,4,5-tetramethyl-1-cyclopentadienyl)zirconium dichloride;
dimethylsilylene(2-methyl-3-(3-pyridyl)-1-indenyl)(2,3,4,5-tetramethyl-1-cyclopentadienyl)zirconium dichloride;
titanium and hafnium analogs of the above zirconium dichloride compounds wherein the zirconium transition metal is replaced with titanium or hafnium; and
dimethyl analogs of the above dichloride compounds wherein the chloride groups on the zirconium, hafnium, or titanium transition metal are replaced with methyl groups.

6. A catalyst system comprising:
(i) the bridged metallocene compound of paragraphs 1 to 4;
(ii) at least one activator (preferably, an alumoxane or a stoichiometric activator);
(iii) optionally, a support material (preferably, magnesia, titania, zirconia, montmorillonite, phyllosilicate, zeolites, talc, clays, and combinations of thereof; more preferably, silica-chromium, silica-alumina, silica-titania, $Al_2O_3$, $ZrO_2$, $SiO_2$, and combinations thereof, more preferably, $SiO_2$, $Al_2O_3$, or $SiO_2/Al_2O_3$);
(iv) optionally, a cocatalyst (preferably, organometallic compounds; preferably, triethylaluminum, tri-isobutylaluminum, tri-n-hexylaluminum, tri-n-octylaluminum, diethyl aluminum chloride, dibutyl zinc, and diethyl zinc).

In another embodiment, this invention relates to:
1A. A bridged metallocene compound represented by the following formula:

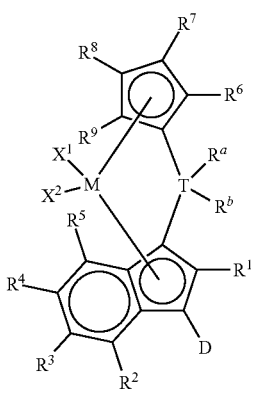

wherein:
M is a group 4 metal;
T is a group 14 atom;
D is a substituted or unsubstituted aromatic group;
$R^a$ and $R^b$ are independently, hydrogen, halogen, or a $C_1$ to $C_{20}$ substituted or unsubstituted hydrocarbyl, and $R^a$ and $R^b$ can form a cyclic structure including substituted or unsubstituted aromatic, partially saturated, or saturated cyclic or fused ring system;

each $X^1$ and $X^2$ is independently selected from the group consisting of $C_1$ to $C_{20}$ substituted or unsubstituted hydrocarbyl groups, hydrides, amides, amines, alkoxides, sulfides, phosphides, halides, dienes, phosphines, and ethers; and $X^1$ and $X^2$ can form a cyclic structure including aromatic, partially saturated, or saturated cyclic or fused ring system;
each of $R^1$, $R^2$, $R^3$, $R^4$, and $R^5$ is, independently, hydrogen, halide, alkoxide or a $C_1$ to $C_{40}$ substituted or unsubstituted hydrocarbyl group, and any of adjacent $R^2$, $R^3$, $R^4$, and/or $R^5$ groups may form a fused ring or multicenter fused ring systems, where the rings may be substituted or unsubstituted, and may be aromatic, partially unsaturated, or unsaturated; and
each of $R^6$, $R^7$, $R^8$, and $R^9$ is, each independently, hydrogen or a $C_1$ to $C_{40}$ substituted or unsubstituted hydrocarbyl group; further provided that at least two of $R^6$, $R^7$, $R^8$, and $R^9$ are $C_1$ to $C_{40}$ substituted or unsubstituted hydrocarbyl groups.
2A. The bridged metallocene compound of paragraph 1A, wherein M is zirconium or hafnium.
3A. The bridged metallocene compound of paragraph 1A or 2A, wherein D is selected from the group consisting of substituted or unsubstituted phenyl, naphthyl, biphenyl, cyclopropenyl, tropylium, cyclooctatetraenyl, furanyl, pyridinyl, borabenzyl, thiophenyl, azolyl, oxazolyl, and imidazolyl.
4A. The bridged metallocene compound of any of paragraph 1A to 3A, wherein T is silicon or germanium.
5A. The bridged metallocene compound of any of paragraph 1A to 4A, wherein each $R^a$ and $R^b$ is independently selected from the group consisting of halides, $C_1$ to $C_{20}$ substituted or unsubstituted hydrocarbyl groups, and cyclic structures where $R^a$ and $R^b$ form a heterocyclopentyl, heterocyclobutyl, or heterocyclohexyl structure with T being the heteroatom.
6A. The bridged metallocene compound of any of paragraph 1A to 5A, wherein each $X^1$ and $X^2$ is independently selected from the group consisting of halides and $C_1$ to $C_{20}$ substituted or unsubstituted hydrocarbyl groups.
7A. The bridged metallocene compound of any of paragraph 1A to 6A, wherein each of $R^1$, $R^2$, $R^3$, $R^4$, $R^5$, $R^6$, $R^7$, $R^8$, and $R^9$ is, independently, hydrogen or a $C_1$ to $C_{20}$ substituted or unsubstituted hydrocarbyl group.
8A. The bridged metallocene compound of any of paragraph 1A to 6A, wherein each of $R^6$, $R^7$, $R^8$, and $R^9$ is, independently, a $C_1$ to $C_{40}$ substituted or unsubstituted hydrocarbyl group.
9A. The bridged metallocene compound of paragraph 8A, wherein $R^6$ and $R^9$ are the same.
10A. The bridged metallocene compound of paragraph 8A, wherein $R^7$ and $R^8$ are the same.
11A. The bridged metallocene compound of any of paragraph 1A to 6A, wherein each of $R^6$, $R^7$, $R^8$, and $R^9$ is, independently, selected from the group consisting of methyl, ethyl, propyl, isopropyl, n-butyl, sec-butyl, t-butyl, pentyl, hexyl, heptyl, octyl, decyl, and undecyl groups, preferably a methyl group, an ethyl group, or an n-propyl group.
12A. The bridged metallocene compound of any of paragraph 1A to 6A, wherein adjacent $R^6$, $R^7$, $R^8$, and/or $R^9$ groups fuse together with the cyclopentadienyl group to form a substituted or unsubstituted fluorene.
13A. The bridged metallocene compound of any of paragraph 1A to 12A, wherein each $R^a$ and $R^b$ is each independently selected from the group consisting of chlorides, fluorides, methyl, and ethyl groups.
14A. A catalyst system comprising the bridged metallocene compounds of any of paragraphs 1A to 13A:
15A. The catalyst system of paragraph 14A, further comprising a support material.

16A. The catalyst system of claim 14A or 15A, wherein the activator is an alumoxane, preferably an alkyl alumoxane.
17A. The catalyst system of paragraphs 14A to 16A, wherein the activator is a stoichiometric activator, preferably an ionic stoichiometric activator.
18A. A process to polymerize olefins comprising contacting olefins with the bridged metallocene compound of any of paragraph 1 to 13A or catalyst systems of any of paragraphs 14A to 17A.
19A. The process of paragraph 18A wherein the polymerization is conducted in the gas phase.

Examples

The following abbreviations may be used below: eq. means equivalents.

All reagents were obtained from Sigma Aldrich (St. Louis, Mo.) and used as obtained, unless stated otherwise. All solvents were anhydrous. All reactions were performed under an inert nitrogen atmosphere, unless otherwise stated. All deuterated solvents were obtained from Cambridge Isotopes (Cambridge, Mass.) and dried over 3 Angstrom molecular sieves before use.

Products were characterized by $^1$H NMR as follows:
$^1$H NMR
$^1$H NMR data was collected at room temperature in a 5 mm probe using a Varian spectrometer with a $^1$H frequency of at least 400 MHz. Data was recorded using a maximum pulse width of 45° C., 8 seconds between pulses and signal averaging 120 transients.

Preparation of dimethyl(3-phenyl-1H-indenyl)(2,3,4, 5-tetramethylcyclopentadienyl) silane (Compound A)

To a solution of chlorodimethyl(2,3,4,5-tetramethylcyclopenta-2,4-dien-1-yl)silane (5.00 g, 23.3 mmol, 1.00 eq.) in ether (25 mL) at −35° C. was added lithium(1-phenylindenide) (4.85 g, 24.5 mmol, 1.05 eq.). The reaction was stirred for 23 hours, and the volatiles were then removed under vacuum. The residue was extracted with pentane (40 mL) and the extract was filtered. The resulting solution was evaporated under vacuum to give a thick oil. Yield 7.07 g (82%). $^1$H NMR(C$_6$D$_6$): δ 7.74 (d, 1H), 7.65 (d, 2H), 7.48 (d, 1H), 7.25 (m, 5H), 6.60 (s, 1H), 3.69, (s, 1H), 2.92 (br s, 1H), 1.93 (s, 3H), 1.90 (s, 3H), 1.82 (s, 3H), 1.821 (s, 3H), −0.09 (s, 3H), −0.39 (s, 3H).

Preparation of dilithium[tetramethylcyclopentadienidedimethylsilyl(3-phenylindenide) 1.10 etherate (Compound B)

To a solution of dimethyl(3-phenyl-1H-indenyl)(2,3,4,5-tetramethylcyclopentadienyl)silane (Compound A, 7.03 g, 19.0 mmol, 1.00 eq.) in ether (25 mL) at −35° C. was added 2.63M butyllithium in hexanes (14.8 mL, 38.9 mmol, 2.05 eq.). The reaction was stirred for 20 hours and then filtered to give a solid. The solid was washed with pentane (2×40 mL) and dried under vacuum. Yield 8.51 g (97%). $^1$H NMR (THF-d8): δ 7.70 (d, 1H), 7.54 (m, 3H), 7.12 (s, 1H), 7.03 (t, 2H), 6.57 (t, 1H), 6.48, (t, 1H), 6.43 (t, 1H), 3.39 (q, 4.4H), 2.20 (s, 6H), 1.91 (s, 6H), 1.13 (t, 6.5H), 0.64 (br s, 6H).

Preparation of dimethylsilylene(2,3,4,5-tetramethyl-1-cyclopentadienyl)(3-phenyl-1-indenyl)zirconium dichloride (Metallocene I)

To a suspension of zirconium tetrachloride bis(etherate) (2.00 g, 5.25 mmol, 1.00 eq.) in ether (25 mL) at −35° C. was added dilithium[tetramethylcyclopentadienidedimethylsilyl (3-phenylindenide) 1.10 etherate (Compound B, 2.43 g, 5.24 mmol, 1.00 eq.). The reaction was stirred for 16 hours and was then evaporated under vacuum, leaving a solid. The solid was extracted with dichloromethane (50 mL, then 3×10 mL) and the extracts were filtered. The resulting solution was evaporated under vacuum to yield a solid. The solid was washed with pentane (2×20 mL) and dried under vacuum. Yield 2.53 g (91%). $^1$H NMR (CD$_2$Cl$_2$): δ 7.90. (d, 1H), 7.60 (m, 3H), 7.49 (t, 2H), 7.38 (m, 2H), 7.10 (m, 1H), 6.00 (s, 1H), 2.00 (s, 3H), 1.96 (s, 3H), 1.92 (s, 3H), 1.89 (s, 3H), 1.23 (s, 3H), 1.00 (s, 3H).

Supported dimethylsilylene(2,3,4,5-tetramethyl-1-cyclopentadienyl)(3-phenyl-1-indenyl)zirconium dichloride (Supported Metallocene I)

30 wt % MAO in toluene (Albemarle, Baton Rouge, La., 6.25 g, 32.3 mmol, 120 eq.) and toluene (6.50 g) were combined and stirred for 15 minutes to give a clear solution. To this MAO solution was added dimethylsilylene(2,3,4,5-tetramethyl-1-cyclopentadienyl)(3-phenyl-1-indenyl)zirconium dichloride (Metallocene I, 0.147 g, 0.27 mmol, 1.00 eq.). The reaction was stirred for 15 minutes and then DAVISON™ 948 silica (5.00 g, dried at 600° C. for 16 hours) was added. The slurry was mixed for 10 minutes and then dried under vacuum for 22 hours. Yield 6.87 g (98%).

Preparation of dimethyl(2,3,4,5-tetramethylcyclopenta-2,4-dien-1-yl)silyl trifluoromethanesulfonate (Compound C)

To a solution of chlorodimethyl(2,3,4,5-tetramethylcyclopenta-2,4-dien-1-yl)silane (30.00 g, 140 mmol, 1.00 eq.) in toluene (100 mL) was added silver trifluoromethanesulfonate (38.00 g, 148 mmol, 1.06 equiv.). The reaction was stirred 3 hours and was then evaporated under vacuum. The residue was extracted with pentane (100 mL) and the extract was filtered. The resulting solution was evaporated under vacuum to give a liquid. Yield 44.72 g (98%). $^1$H NMR(C$_6$D$_6$): δ 2.78 (br s, 1H), 1.74 (s, 6H), 1.61 (s, 6H), 0.04 (s, 6H).

Preparation of (3-(4-(tert-Butyl)phenyl)-1H-inden-1-yl)dimethyl(2,3,4,5-tetramethylcyclopenta-2,4-dien-1-yl)silane (Compound D)

To a solution of dimethyl(2,3,4,5-tetramethylcyclopenta-2,4-dien-1-yl)silyl trifluoromethanesulfonate (Compound C, 7.50 g, 22.8 mmol, 1.00 eq.) in ether (25 mL) at −35° C. was added lithium (1-(4-t-butylphenyl)indenide) (6.20 g, 24.4 mmol, 1.07 eq.). The reaction was stirred for 18 hours, and was then evaporated under vacuum. The residue was extracted with pentane (40 mL) and the extract was filtered. The resulting solution was evaporated under vacuum to give a thick oil. Yield 10.11 g (104%). $^1$H NMR(C$_6$D$_6$): δ 7.83 (d, 1H), 7.67 (d, 2H), 7.50 (d, 1H), 7.41 (d, 2H), 7.26 (m, 2H), 6.64 (s, 1H), 3.71, (s, 1H), 2.95 (br s, 1H), 1.95 (s, 3H), 1.93 (s, 3H), 1.84 (s, 3H), 1.82 (s, 3H), 1.30 (s, 9H), −0.06 (s, 3H), −0.36 (s, 3H).

Preparation of dilithium[tetramethylcyclopentadienidedimethylsilyl(3-(4-t-butylphenyl)indenide) etherate (Compound E)

To a solution of (3-(4-(tert-butyl)phenyl)-1H-inden-1-yl) dimethyl(2,3,4,5-tetramethylcyclopenta-2,4-dien-1-yl)silane (Compound D, 10.01 g, 23.5 mmol, 1.00 eq.) in ether (35 mL) at −35° C. was added 2.56M butyllithium in hexanes (19.0 mL, 48.6 mmol, 2.07 eq.). The reaction was stirred for 18 hours and then evaporated under vacuum to give a solid. The solid was washed with pentane (2×40 mL) and dried under vacuum. Yield 11.67 g (97%). $^1$H NMR (THF-d8): δ 7.71 (d, 1H), 7.52 (m, 3H), 7.16 (d, 2H), 7.09 (s, 1H), 6.50 (t, 1H), 6.43, (t, 1H), 3.42 (q, 4H), 2.22 (s, 6H), 1.93 (s, 6H), 1.34 (s, 9H), 1.15 (t, 6H), 0.69 (br s, 6H).

Preparation of Dimethylsilylene(2,3,4,5-tetramethyl-1-cyclopentadienyl)(3-(4-t-butylphenyl)-1-indenyl) zirconium dichloride (Metallocene II)

To a suspension of zirconium tetrachloride bis(etherate) (2.00 g, 5.25 mmol, 1.00 eq.) in ether (35 mL) at −35° C. was added dilithium[tetramethylcyclopentadienidedimethylsilyl (3-(4-t-butylphenyl)indenide) etherate (Compound D, 2.43 g, 5.24 mmol, 1.00 eq.). The reaction was stirred for 17 hours and was then evaporated under vacuum, leaving a solid. The solid was extracted with dichloromethane (40 mL, then 2×10 mL) and the extracts were filtered. The resulting solution was evaporated under vacuum to yield a solid. The solid was washed with pentane (10 mL) and dried under vacuum. Yield 2.62 g (85%). $^1$H NMR (CD$_2$Cl$_2$): δ 7.81 (d, 1H), 7.59 (d, 1H), 7.52 (s, 4H), 7.38 (m, 1H), 7.08 (m, 1H), 5.98 (s, 1H), 1.99 (s, 3H), 1.95 (s, 3H), 1.92 (s, 3H), 1.89 (s, 3H), 1.38 (s, 9H), 1.22 (s, 3H), 0.96 (s, 3H).

Supported Dimethylsilylene(2,3,4,5-tetramethyl-1-cyclopentadienyl)(3-phenyl-1-indenyl)zirconium dichloride (Supported Metallocene II)

30 wt % MAO in toluene (6.27 g, 32.4 mmol, 120 eq.) and toluene (6.50 g) were combined and stirred for 15 minutes to give a clear solution. To this MAO solution was added dimethylsilylene(2,3,4,5-tetramethyl-1-cyclopentadienyl)(3-(4-t-butylphenyl)-1-indenyl)zirconium dichloride (Metallocene II, 0.158 g, 0.269 mmol, 1.00 eq.). The reaction was stirred for 15 minutes and then DAVISON™ 948 silica (5.00 g, dried at 600° C. for 16 hours) was added. The slurry was mixed for 10 minutes and then dried under vacuum for 24 hours. Yield 6.92 g (98%).

Preparation of (3-(3,5-dimethylphenyl)-1H-inden-1-yl)dimethyl(2,3,4,5-tetramethylcyclopenta-2,4-dien-1-yl)silane (Compound F)

To a solution of dimethyl(2,3,4,5-tetramethylcyclopenta-2,4-dien-1-yl)silyl trifluoromethanesulfonate (Compound C, 7.50 g, 22.8 mmol, 1.00 eq.) in ether (25 mL) at −35° C. was added lithium (1-(3,5-dimethylphenyl)indenide) (5.53 g, 24.4 mmol, 1.07 eq.). The reaction was stirred for 19 hours, and was then evaporated under vacuum. The residue was extracted with pentane (40 mL, then 2×20 mL) and the extract was filtered. The resulting solution was evaporated under vacuum to give a sticky solid. Yield 9.65 g (106%). $^1$H NMR (C$_6$D$_6$): δ 7.87 (d, 1H), 7.40 (s, 2H), 7.25 (m, 2H), 6.88 (s, 1H), 6.64 (s, 1H), 3.73, (s, 1H), 2.93 (br s, 1H), 2.23 (s, 6H), 1.93 (s, 3H), 1.92 (s, 3H), 1.84 (s, 3H), 1.82 (s, 3H), −0.07 (s, 3H), −0.36 (s, 3H).

Preparation of dilithium[tetramethylcyclopentadienidedimethylsilyl(3-(3,5-dimethylphenyl)indenide) etherate (Compound G)

To a solution of (3-(3,5-dimethylphenyl)-1H-inden-1-yl) dimethyl(2,3,4,5-tetramethylcyclopenta-2,4-dien-1-yl)si-lane (Compound F, 9.58 g, 24.0 mmol, 1.00 eq.) in ether (35 mL) at −35° C. was added 2.56M butyllithium in hexanes (19.5 mL, 49.9 mmol, 2.08 eq.). The reaction was stirred for 17 hours and then filtered to give a solid. The solid was washed with pentane (2×30 mL) and dried under vacuum. Yield 9.50 g (82%). $^1$H NMR (THF-d8): δ 7.72 (d, 1H), 7.53 (d, 1H), 7.23 (s, 2H), 7.12 (s, 1H), 6.48 (t, 1H), 6.41, (t, 1H), 6.31 (s, 1H), 3.40 (q, 4H), 2.24 (s, 3H), 2.21 (s, 3H), 1.92 (s, 6H), 1.13 (t, 6H), 0.66 (br s, 6H).

Preparation of dimethylsilylene(2,3,4,5-tetramethyl-1-cyclopentadienyl)(3-(3,5-dimethylphenyl)-1-indenyl)zirconium dichloride (Metallocene III)

To a suspension of zirconium tetrachloride bis(etherate) (2.00 g, 5.25 mmol, 1.00 eq.) in ether (25 mL) at −35° C. was added dilithium[tetramethylcyclopentadienidedimethylsilyl (3-(3,5-dimethylphenyl)indenide) etherate (Compound G, 2.54 g, 5.24 mmol, 1.00 eq.). The reaction was stirred for 18 hours and was then evaporated under vacuum, leaving a solid. The solid was extracted with dichloromethane (30 mL, then 2×10 mL) and the extracts were filtered. The resulting solution was evaporated under vacuum to yield a solid. The solid was washed with pentane (10 mL) and dried under vacuum. Yield 2.54 g (87%). $^1$H NMR (CD$_2$Cl$_2$): δ 7.89 (d, 1H), 7.59 (d, 1H), 7.38 (t, 1H), 7.20 (s, 2H), 7.09 (t, 1H), 5.98 (s, 1H), 2.40 (s, 6H), 1.99 (s, 3H), 1.96 (s, 3H), 1.92 (s, 3H), 1.89 (s, 3H), 1.22 (s, 3H), 1.00 (s, 3H).

Supported dimethylsilylene(2,3,4,5-tetramethyl-1-cyclopentadienyl)(3-(3,5-dimethylphenyl)-1-indenyl) zirconium dichloride (Supported Metallocene III)

30 wt % MAO in toluene (6.26 g, 32.4 mmol, 120 eq.) and toluene (6.50 g) were combined and stirred for 15 minutes to give a clear solution. To this MAO solution was added dimethylsilylene(2,3,4,5-tetramethyl-1-cyclopentadienyl)(3-(3, 5-dimethylphenyl)-1-indenyl)zirconium dichloride (Metallocene III, 0.151 g, 0.270 mmol, 1.00 eq.). The reaction was stirred for 15 minutes and then DAVISON™ 948 silica (5.00 g, dried at 60° C.) was added. The slurry was mixed for 10 minutes and then dried under vacuum for 23 hours. Yield 6.87 g (98%).

Preparation of (3-([1,1'-biphenyl]-4-yl)-1H-inden-1-yl)dimethyl(2,3,4,5-tetramethylcyclopenta-2,4-dien-1-yl)silane (Compound H)

To a solution of dimethyl(2,3,4,5-tetramethylcyclopenta-2,4-dien-1-yl)silyl trifluoromethanesulfonate (Compound C, 7.50 g, 22.8 mmol, 1.00 eq.) in ether (25 mL) at −35° C. was added lithium (1-(4-biphenyl)indenide) (6.70 g, 24.4 mmol, 1.07 eq.). The reaction was stirred for 23 hours, and was then evaporated under vacuum. The residue was extracted with pentane (50 mL, then 2×25 mL) and the extract was filtered. The resulting solution was evaporated under vacuum to give a thick oil. The oil was extracted with pentane and the extracts were filtered to give a solution. The solution was evaporated under vacuum to give a foam. Yield 10.07 g (93%). $^1$H NMR (C$_6$D$_6$): δ 7.82 (d, 1H), 7.72 (d, 2H), 7.59 (m, 4H) 7.51 (d, 1H), 7.26 (m, 5H), 6.67 (d, 1H), 3.73, (s, 1H), 2.94 (br s, 1H), 1.95 (s, 3H), 1.93 (s, 3H), 1.85 (s, 3H), 1.83 (s, 3H), −0.06 (s, 3H), −0.35 (s, 3H).

Preparation of dilithium[tetramethylcyclopentadienidedimethylsilyl(3-(4-biphenyl)indenide) etherate (Compound I)

To a solution of (3-([1,1'-biphenyl]-4-yl)-1H-inden-1-yl) dimethyl(2,3,4,5-tetramethylcyclopenta-2,4-dien-1-yl)silane (Compound H, 10.04 g, 22.5 mmol, 1.00 eq.) in ether (30 mL) at −35° C. was added 2.66M butyllithium in hexanes (17.5 mL, 46.6 mmol, 2.07 eq.). The reaction was stirred for 18 hours and then filtered to give a solid. The solid was washed with pentane (2×20 mL) and dried under vacuum. Yield 11.12 g (93%). $^1$H NMR (THF-d8): δ 7.74 (d, 1H), 7.64 (d, 2H), 7.55 (m, 3H), 7.36 (d, 2H), 7.30 (t, 2H), 7.21 (s, 1H), 7.10 (t, 1H), 6.51 (t, 1H), 6.41, (t, 1H), 3.39 (q, 4H), 2.19 (s, 6H), 1.92 (s, 6H), 1.12 (t, 6H), 0.61 (br s, 6H).

Preparation of dimethylsilylene(2,3,4,5-tetramethyl-1-cyclopentadienyl)(3-(4-biphenyl)-1-indenyl)zirconium dichloride (Metallocene IV)

To a suspension of zirconium tetrachloride bis(etherate) (2.00 g, 5.25 mmol, 1.00 eq.) in ether (25 mL) at −35° C. was added dilithium[tetramethylcyclopentadienidedimethylsilyl (3-(4-biphenyl)indenide) etherate (Compound I, 2.79 g, 5.24 mmol, 1.00 eq.). The reaction was stirred for 18 hours and was then evaporated under vacuum, leaving a solid. The solid was extracted with dichloromethane (10×100 mL) and the extracts were filtered. The resulting solution was evaporated under vacuum to yield a solid. The solid was washed with pentane (2×20 mL) and dried under vacuum. Yield 2.01 g (63%). $^1$H NMR (CD$_2$Cl$_2$): δ 7.94 (d, 1H), 7.74 (d, 2H), 7.63 (t, 3H), 7.59 (d, 1H), 7.39 (m, 5H), 7.11 (d, 1H), 6.04 (s, 1H), 2.00 (s, 3H), 1.96 (s, 3H), 1.93 (s, 3H), 1.90 (s, 3H), 1.22 (s, 3H), 1.01 (s, 3H).

Supported dimethylsilylene(2,3,4,5-tetramethyl-1-cyclopentadienyl)(3-(4-biphenyl)-1-indenyl)zirconium dichloride (Supported Metallocene IV)

30 wt % MAO in toluene (6.27 g, 32.4 mmol, 120 eq.) and toluene (6.50 g) were combined and stirred for 15 minutes to give a clear solution. To this MAO solution was added dimethylsilylene(2,3,4,5-tetramethyl-1-cyclopentadienyl)(3-(4-biphenyl)-1-indenyl)zirconium dichloride (Metallocene IV, 0.164 g, 0.270 mmol, 1.00 eq.). The reaction was stirred for 15 minutes and then DAVISON™ 948 silica (5.00 g, dried at 600° C.) was added. The solid was mixed for 10 minutes and then dried under vacuum for 23 hours. Yield 6.94 g (98%).

Preparation of dimethyl(3-(naphthalen-2-yl)-1H-inden-1-yl)(2,3,4,5-tetramethylcyclopenta-2,4-dien-1-yl)silane (Compound J)

To a solution of dimethyl(2,3,4,5-tetramethylcyclopenta-2,4-dien-1-yl)silyl trifluoromethanesulfonate (Compound C, 7.50 g, 22.8 mmol, 1.00 eq.) in ether (25 mL) at −35° C. was added lithium (1-(2-naphthyl)indenide) (6.05 g, 24.4 mmol, 1.07 eq.). The reaction was stirred for 19 hours, and was then evaporated under vacuum. The residue was extracted with pentane (40 mL, then 2×20 mL) and the extract was filtered. The resulting solution was evaporated under vacuum to give a foam. The foam was extracted with pentane and the extracts were filtered to give a solution. The solution was evaporated under vacuum to give thick oil. Yield 9.44 g (98%). $^1$H NMR (C$_6$D$_6$): δ 8.20 (s, 1H), 7.84 (d, 1H), 7.76 (m, 2H), 7.70 (m, 2H) 7.51 (d, 1H), 7.27 (m, 4H), 6.71 (s, 1H), 3.75, (s, 1H), 2.94 (br s, 1H), 1.95 (s, 3H), 1.93 (s, 3H), 1.84 (s, 3H), 1.82 (s, 3H), −0.04 (s, 3H), −0.34 (s, 3H).

Preparation of dilithium[tetramethylcyclopentadien-idedimethylsilyl(3-(2-naphthyl)indenide)etherate (Compound K)

To a solution of dimethyl(3-(naphthalen-2-yl)-1H-inden-1-yl)(2,3,4,5-tetramethylcyclopenta-2,4-dien-1-yl)silane (Compound J, 9.40 g, 22.3 mmol, 1.00 eq.) in ether (30 mL) at −35° C. was added 2.66M butyllithium in hexanes (17.5 mL, 46.6 mmol, 2.078 eq.). The reaction was stirred for 25 hours and then evaporated under vacuum to give a solid. The solid was washed with pentane (2×40 mL) and dried under vacuum. Yield 11.04 g (97%). $^1$H NMR (THF-d8): δ 7.87 (m, 2H), 7.81 (s, 1H), 7.63 (m, 4H), 7.28 (s, 1H), 7.12 (t, 1H), 6.92 (t, 1H), 6.54 (t, 1H), 6.43 (t, 1H), 3.40 (q, 4H), 2.19 (s, 6H), 1.92 (s, 6H), 1.13 (t, 6H), 0.61 (br s, 6H).

Preparation of dimethylsilylene(2,3,4,5-tetramethyl-1-cyclopentadienyl)(3-(2-naphthyl)-1-indenyl)zirconium dichloride (Metallocene V)

To a suspension of zirconium tetrachloride bis(etherate) (2.00 g, 5.25 mmol, 1.00 eq.) in ether (25 mL) at −35° C. was added dilithium[tetramethylcyclopentadienidedimethylsilyl (3-(2-naphthyl)indenide) etherate (Compound K, 2.66 g, 5.25 mmol, 1.00 eq.). The reaction was stirred for 21 hours and was then evaporated under vacuum, leaving a solid. The solid was extracted with dichloromethane (40 ml, then 2×10 mL) and the extracts were filtered. The resulting solution was evaporated under vacuum to yield a solid. The solid was washed with pentane (2×20 mL) and dried under vacuum. Yield 2.68 g (88%). $^1$H NMR (CD$_2$Cl$_2$): δ 8.01 (m, 2H), 7.81 (m, 3H), 7.77 (d, 1H), 7.63 (d, 1H), 7.51 (m, 2H), 7.43 (m, 1H), 7.12 (m, 1H), 6.13 (s, 1H), 2.01 (s, 3H), 1.94 (s, 3H), 1.93 (s, 3H), 1.90 (s, 3H), 1.25 (s, 3H), 1.03 (s, 3H).

Supported dimethylsilylene(2,3,4,5-tetramethyl-1-cyclopentadienyl)(3-(2-naphthyl)-1-indenyl)zirconium dichloride (Supported Metallocene V)

30 wt % MAO in toluene (6.27 g, 32.4 mmol, 120 eq.) and toluene (6.50 g) were combined and stirred for 15 minutes to give a clear solution. To this MAO solution was added dimethylsilylene(2,3,4,5-tetramethyl-1-cyclopentadienyl)(3-(2-naphthyl)-1-indenyl)zirconium dichloride (Metallocene V, 0.157 g, 0.270 mmol, 1.00 eq.). The reaction was stirred 15 for minutes and then DAVISON™ 948 silica (5.00 g, dried at 600° C. for 16 hours) was added. The slurry was mixed for 10 minutes and then dried under vacuum for 23 hours. Yield 6.83 g (97%).

Preparation of (4,7-Dimethyl-3-phenyl-1H-inden-1-yl)dimethyl(2,3,4,5-tetramethylcyclopenta-2,4-dien-1-yl)silane (Compound L)

To a solution of dimethyl(2,3,4,5-tetramethylcyclopenta-2,4-dien-1-yl)silyl trifluoromethanesulfonate (Compound C, 7.50 g, 22.8 mmol, 1.00 eq.) in ether (25 mL) at −35° C. was added lithium (4,7-dimethyl-1-phenylindenide) (5.53 g, 24.4 mmol, 1.07 eq.). The reaction was stirred for 25 hours, and was then evaporated under vacuum. The residue was extracted with pentane (3×40 mL) and the extract was filtered. The resulting solution was evaporated under vacuum to give a thick oil. Yield 9.07 g (100%). $^1$H NMR(C$_6$D$_6$): δ 7.41 (d, 2H), 7.19 (m, 2H), 6.97 (s, 3H), 6.45 (d, 1H), 3.78, (s, 1H), 2.86 (br s, 1H), 2.30 (s, 3H), 2.13 (s, 3H), 1.96 (s, 3H), 1.89 (s, 3H), 1.78 (s, 3H), 1.77 (s, 3H), −0.04 (s, 3H), −0.32 (s, 3H).

Preparation of dilithium[tetramethylcyclopentadien-idedimethylsilyl(4,7-dimethyl-3-phenylindenide) 1.10 etherate (Compound M)

To a solution of (4,7-dimethyl-3-phenyl-1H-inden-1-yl) dimethyl(2,3,4,5-tetramethylcyclopenta-2,4-dien-1-yl)silane (Compound L, 8.98 g, 22.5 mmol, 1.00 eq.) in ether (40 mL) at −35° C. was added 2.56M butyllithium in hexanes (18.0 mL, 46.1 mmol, 2.05 eq.). The reaction was stirred for 17 hours and then filtered to give a solid. The solid was washed with pentane (2×20 mL) and dried under vacuum. Yield 9.62 g (87%). $^1$H NMR (THF-d8): δ 7.30 (d, 2H), 7.12 (t, 2H), 6.89 (m, 2H), 6.22 (s, 2H), 3.39 (q, 4.3H), 2.65 (s, 3H), 2.24 (s, 3H), 2.00 (s, 6H), 1.91 (s, 6H), 1.12 (t, 6.6H), 0.56 (br s, 6H).

Preparation of dimethylsilylene(2,3,4,5-tetramethyl-1-cyclopentadienyl)(4,7-dimethyl-3-phenyl-1-indenyl)zirconium dichloride (Metallocene VI)

To a suspension of zirconium tetrachloride bis(etherate) (2.00 g, 5.25 mmol, 1.00 eq.) in ether (25 mL) at −35° C. was added dilithium[tetramethylcyclopentadienidedimethylsilyl (4,7-dimethyl-3-phenylindenide) 1.10 etherate (Compound M, 2.58 g, 5.24 mmol, 1.00 eq.). The reaction was stirred for 16 hours and was then evaporated under vacuum, leaving a solid. The solid was extracted with dichloromethane (50 mL, then 2×10 mL) and the extracts were filtered. The resulting solution was evaporated under vacuum to yield a solid. The solid was washed with pentane (2×20 mL) and dried under vacuum. Yield 2.53 g (86%). $^1$H NMR (CD$_2$Cl$_2$): δ 7.39 (m, 2H), 7.32 (d, 1H), 7.24 (d, 2H), 7.02 (d, 2H), 6.93 (d, 1H), 6.25 (s, 1H), 2.37 (s, 3H), 2.27 (s, 3H), 2.19 (s, 3H), 2.03 (s, 3H), 1.97 (s, 3H), 1.95 (s, 3H), 1.10 (s, 3H), 1.02 (s, 3H).

Supported Dimethylsilylene(2,3,4,5-tetramethyl-1-cyclopentadienyl)(4,7-dimethyl-3-phenyl-1-indenyl)zirconium dichloride (Supported Metallocene VI)

30 wt % MAO in toluene (6.26 g, 32.4 mmol, 120 eq.) and toluene (6.50 g) were combined and stirred for 15 minutes to give a clear solution. To this MAO solution was added dimethylsilylene(2,3,4,5-tetramethyl-1-cyclopentadienyl)(4,7-dimethyl-3-phenyl-1-indenyl)zirconium dichloride (Metallocene VI, 0.151 g, 0.270 mmol, 1.00 eq.). The reaction was stirred for 15 minutes and then DAVISON™ 948 silica (5.00 g, dried at 600° C.) was added. The slurry was mixed for 10 minutes and then dried under vacuum for 23 hours. Yield 6.93 g (99%).

Preparation of (5,6-Dimethyl-3-phenyl-1H-inden-1-yl)dimethyl(2,3,4,5-tetramethylcyclopenta-2,4-dien-1-yl)silane (Compound N)

To a solution of dimethyl(2,3,4,5-tetramethylcyclopenta-2,4-dien-1-yl)silyl trifluoromethanesulfonate (Compound C, 7.50 g, 22.8 mmol, 1.00 eq.) in ether (25 mL) at −35° C. was added lithium (5,6-dimethyl-1-phenylindenide) (5.53 g, 24.4 mmol, 1.07 eq.). The reaction was stirred for 24 hours, and was then evaporated under vacuum. The residue was extracted with pentane (40 mL, then 2×25 mL) and the extract was filtered. The resulting solution was evaporated under vacuum to give a sticky solid. Yield 9.34 g (103%). $^1$H NMR (C$_6$D$_6$): δ 7.71 (d, 2H), 7.62 (s, 1H), 7.36 (s, 1H), 7.31 (t, 2H), 7.20 (m, 1H), 6.57 (s, 1H), 3.70, (s, 1H), 2.98 (br s, 1H), 2.23 (s, 3H), 2.17 (s, 3H), 1.97 (s, 3H), 1.95 (s, 3H), 1.84 (s, 6H), −0.04 (s, 3H), −0.32 (s, 3H).

Preparation of dilithium[tetramethylcyclopentadienidedimethylsilyl(5,6-dimethyl-3-phenylindenide) etherate (Compound O)

To a solution of (5,6-dimethyl-3-phenyl-1H-inden-1-yl) dimethyl(2,3,4,5-tetramethylcyclopenta-2,4-dien-1-yl)silane (Compound N, 9.52 g, 23.9 mmol, 1.00 eq.) in ether (40 mL) at −35° C. was added 2.56M butyllithium in hexanes (19.0 mL, 48.6 mmol, 2.04 eq.). The reaction was stirred for 18 hours and then filtered to give a solid. The solid was washed with pentane (2×20 mL) and dried under vacuum. Yield 9.68 g (84%). $^1$H NMR (THF-d8): δ 7.55 (m, 3H), 7.34 (s, 1H), 7.04 (m, 3H), 6.58 (t, 1H), 3.40 (q, 4H), 2.27 (s, 3H), 2.25 (s, 3H), 2.21 (s, 6H), 1.90 (s, 6H), 1.13 (t, 6H), 0.65 (br s, 6H).

Preparation of dimethylsilylene(2,3,4,5-tetramethyl-1-cyclopentadienyl)(5,6-dimethyl-3-phenyl-1-indenyl)zirconium dichloride (Metallocene VII)

To a suspension of zirconium tetrachloride bis(etherate) (2.00 g, 5.25 mmol, 1.00 eq.) in ether (25 mL) at −35° C. was added dilithium[tetramethylcyclopentadienidedimethylsilyl (5,6-dimethyl-3-phenylindenide) etherate (Compound O, 2.54 g, 5.24 mmol, 1.00 eq.). The reaction was stirred for 17 hours and was then evaporated under vacuum, leaving a solid. The solid was extracted with dichloromethane (50 mL, then 2×10 mL) and the extracts were filtered. The resulting solution was evaporated under vacuum to yield a solid. The solid was washed with pentane (2×20 mL) and dried under vacuum. Yield 2.67 g (91%). $^1$H NMR (CD$_2$Cl$_2$): δ 7.69. (s, 1H), 7.59 (d, 2H), 7.48 (t, 2H), 7.34 (m, 2H), 5.87 (s, 1H), 2.41 (s, 3H), 2.27 (s, 3H), 1.99 (s, 3H), 1.94 (s, 3H), 1.92 (s, 3H), 1.86 (s, 3H), 1.22 (s, 3H), 0.97 (s, 3H).

Supported dimethylsilylene(2,3,4,5-tetra methyl-1-cyclopentadienyl)(5,6-dimethyl-3-phenyl-1-indenyl)zirconium dichloride (Supported Metallocene VII)

30 wt % MAO in toluene (6.26 g, 32.4 mmol, 120 eq.) and toluene (6.50 g) were combined and stirred for 15 minutes to give a clear solution. To this MAO solution was added dimethylsilylene(2,3,4,5-tetramethyl-1-cyclopentadienyl)(5,6-dimethyl-3-phenyl-1-indenyl)zirconium dichloride (Metallocene VII, 0.151 g, 0.270 mmol, 1.00 eq.). The reaction was stirred for 15 minutes and then DAVISON™ 948 silica (5.00 g, dried at 600° C. for 16 hours) was added. The solid was mixed for 10 minutes and then dried under vacuum for 23 hours. Yield 6.91 g (98%).

All documents described herein are incorporated by reference herein, including any priority documents and/or testing procedures to the extent they are not inconsistent with this text, provided however that any priority document not named in the initially filed application or filing documents is NOT incorporated by reference herein. As is apparent from the foregoing general description and the specific embodiments, while forms of the invention have been illustrated and described, various modifications can be made without departing from the spirit and scope of the invention. Accordingly, it is not intended that the invention be limited thereby. Likewise, the term "comprising" is considered synonymous with the term "including" for purposes of Australian law. Likewise, "comprising" encompasses the terms "consisting essentially of," "is," and "consisting of" and anyplace "comprising" is used "consisting essentially of," "is," or "consisting of" may be substituted therefor.

What is claimed is:

1. A bridged metallocene compound represented by the following formula:

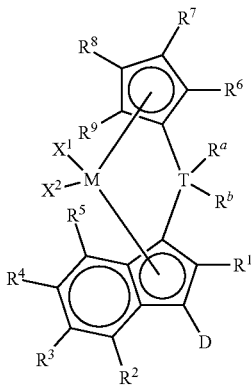

wherein:
M is a group 4 metal;
T is a group 14 atom;
D is a substituted or unsubstituted aromatic group;
$R^a$ and $R^b$ are independently, hydrogen, halogen, or a $C_1$ to $C_{20}$ substituted or unsubstituted hydrocarbyl, and $R^a$ and $R^b$ optionally form a cyclic structure including substituted or unsubstituted aromatic, partially saturated, or saturated cyclic or fused ring system;
each $X^1$ and $X^2$ is independently selected from the group consisting of $C_1$ to $C_{20}$ substituted or unsubstituted hydrocarbyl groups, hydrides, amides, amines, alkoxides, sulfides, phosphides, halides, dienes, phosphines, and ethers; and $X^1$ and $X^2$ optionally form a cyclic structure including aromatic, partially saturated, or saturated cyclic or fused ring system;
each of $R^1$, $R^2$, $R^3$, $R^4$, and $R^5$ is, independently, hydrogen, halide, alkoxide or a $C_1$ to $C_{40}$ substituted or unsubstituted hydrocarbyl group, and any of adjacent $R^2$, $R^3$, $R^4$, and/or $R^5$ groups optionally form a fused ring or multicenter fused ring systems, where the rings are substituted or unsubstituted, and are optionally aromatic, partially unsaturated, or unsaturated; and
each of $R^6$, $R^7$, $R^8$, and $R^9$ is, each independently, hydrogen or a methyl, ethyl, propyl, isopropyl, n-butyl, sec-butyl, t-butyl, pentyl, hexyl, heptyl, octyl, decyl, or undecyl group;
further provided that at least two of $R^6$, $R^7$, $R^8$, and $R^9$ are methyl, ethyl, propyl, isopropyl, n-butyl, sec-butyl, t-butyl, pentyl, hexyl, heptyl, octyl, decyl, or undecyl group.

2. The bridged metallocene compound of claim 1, wherein M is zirconium or hafnium.

3. The bridged metallocene compound of claim 1, wherein D is selected from the group consisting of substituted or unsubstituted phenyl, naphthyl, biphenyl, cyclopropenyl, tropylium, cyclooctatetraenyl, furanyl, pyridinyl, borabenzyl, thiophenyl, azolyl, oxazolyl, and imidazolyl.

4. The bridged metallocene compound of claim 1, wherein T is silicon or germanium.

5. The bridged metallocene compound of claim 1, wherein each $R^a$ and $R^b$ is independently selected from the group consisting of halides, $C_1$ to $C_{20}$ substituted or unsubstituted hydrocarbyl groups, and cyclic structures where $R^a$ and $R^b$ form a heterocyclopentyl, heterocyclobutyl, or heterocyclohexyl structure with T being the heteroatom.

6. The bridged metallocene compound of claim 1, wherein each $X^1$ and $X^2$ is independently selected from the group consisting of halides and $C_1$ to $C_{20}$ substituted or unsubstituted hydrocarbyl groups.

7. The bridged asymmetric metallocene compound of claim 1, wherein the metallocene compound is one or more of:
dimethylsilylene(3-phenyl-1-indenyl)(2,3,4,5-tetramethyl-1-cyclopentadienyl)zirconium dichloride;
dimethylsilylene(3-phenyl-1-indenyl)(2,5-dimethyl-1-cyclopentadienyl)zirconium dichloride;
dimethylsilylene(3-phenyl-1-indenyl)(3,4-dimethyl-1-cyclopentadienyl)zirconium dichloride;
dimethylsilylene(3-phenyl-1-indenyl)(2,3,4,5-tetraethyl-1-cyclopentadienyl)zirconium dichloride;
dimethylsilylene(3-phenyl-1-indenyl)(2,3,4,5-tetrapropyl-1-cyclopentadienyl)zirconium dichloride;
diethylsilylene(3-phenyl-1-indenyl)(2,3,4,5-tetramethyl-1-cyclopentadienyl)zirconium dichloride;
dipropylsilylene(3-phenyl-1-indenyl)(2,3,4,5-tetramethyl-1-cyclopentadienyl)zirconium dichloride;
dibutylsilylene(3-phenyl-1-indenyl)(2,3,4,5-tetramethyl-1-cyclopentadienyl)zirconium dichloride;
diphenylsilylene(3-phenyl-1-indenyl)(2,3,4,5-tetramethyl-1-cyclopentadienyl)zirconium dichloride;
silacyclobutylidene(3-phenyl-1-indenyl)(2,3,4,5-tetramethyl-1-cyclopentadienyl)zirconium dichloride;
silacyclopentylidene(3-phenyl-1-indenyl)(2,3,4,5-tetramethyl-1-cyclopentadienyl)zirconium dichloride;
silacyclohexylidene(3-phenyl-1-indenyl)(2,3,4,5-tetramethyl-1-cyclopentadienyl)zirconium dichloride;
dimethylgermylene(3-phenyl-1-indenyl)(2,3,4,5-tetramethyl-1-cyclopentadienyl)zirconium dichloride;
diethylgermylene(3-phenyl-1-indenyl)(2,3,4,5-tetramethyl-1-cyclopentadienyl)zirconium dichloride;
dipropylgermylene(3-phenyl-1-indenyl)(2,3,4,5-tetramethyl-1-cyclopentadienyl)zirconium dichloride;
dibutylgermylene(3-phenyl-1-indenyl)(2,3,4,5-tetramethyl-1-cyclopentadienyl)zirconium dichloride;
diphenylgermylene(3-phenyl-1-indenyl)(2,3,4,5-tetramethyl-1-cyclopentadienyl)zirconium dichloride;
isopropylidene(3-phenyl-1-indenyl)(2,3,4,5-tetramethyl-1-cyclopentadienyl)zirconium dichloride;
diphenylmethylene(3-phenyl-1-indenyl)(2,3,4,5-tetramethyl-1-cyclopentadienyl)zirconium dichloride;
dimethylsilylene(2-methyl-3-phenyl-1-indenyl)(2,3,4,5-tetramethyl-1-cyclopentadienyl)zirconium dichloride;
dimethylsilylene(2-ethyl-3-phenyl-1-indenyl)(2,3,4,5-tetramethyl-1-cyclopentadienyl)zirconium dichloride;
dimethylsilylene(2-propyl-3-phenyl-1-indenyl)(2,3,4,5-tetramethyl-1-cyclopentadienyl)zirconium dichloride;
dimethylsilylene(2-isopropyl-3-phenyl-1-indenyl)(2,3,4,5-tetramethyl-1-cyclopentadienyl)zirconium dichloride;
dimethylsilylene(4-methyl-3-phenyl-1-indenyl)(2,3,4,5-tetramethyl-1-cyclopentadienyl)zirconium dichloride;
dimethylsilylene(4,7-dimethyl-3-phenyl-1-indenyl)(2,3,4,5-tetramethyl-1-cyclopentadienyl)zirconium dichloride;
dimethylsilylene(5,6-dimethyl-3-phenyl-1-indenyl)(2,3,4,5-tetramethyl-1-cyclopentadienyl)zirconium dichloride;
dimethylsilylene(2,4-dimethyl-3-phenyl-1-indenyl)(2,3,4,5-tetramethyl-1-cyclopentadienyl)zirconium dichloride;

dimethylsilylene(2,6-dimethyl-3-phenyl-1-indenyl)(2,3,4,5-tetramethyl-1-cyclopentadienyl)zirconium dichloride;
dimethylsilylene(3-phenyl-2,4,6-trimethyl-1-indenyl)(2,3,4,5-tetramethyl-1-cyclopentadienyl)zirconium dichloride;
dimethylsilylene(3-phenyl-2,4,7-trimethyl-1-indenyl)(2,3,4,5-tetramethyl-1-cyclopentadienyl)zirconium dichloride;
dimethylsilylene(3-phenyl-2,5,6-trimethyl-1-indenyl)(2,3,4,5-tetramethyl-1-cyclopentadienyl)zirconium dichloride;
dimethylsilylene(3-phenyl-4,5,6,7-tetramethyl-1-indenyl)(2,3,4,5-tetramethyl-1-cyclopentadienyl)zirconium dichloride;
dimethylsilylene(2,4,5,6,7-pentamethyl-3-phenyl-1-indenyl)(2,3,4,5-tetramethyl-1-cyclopentadienyl)zirconium dichloride;
dimethylsilylene(6-chloro-3-phenyl-1-indenyl)(2,3,4,5-tetramethyl-1-cyclopentadienyl)zirconium dichloride;
dimethylsilylene(7-chloro-3-phenyl-1-indenyl)(2,3,4,5-tetramethyl-1-cyclopentadienyl)zirconium dichloride;
dimethylsilylene(4,6-dichloro-3-phenyl-1-indenyl)(2,3,4,5-tetramethyl-1-cyclopentadienyl)zirconium dichloride;
dimethylsilylene(5,7-dichloro-2-methyl-3-phenyl-1-indenyl)(2,3,4,5-tetramethyl-1-cyclopentadienyl)zirconium dichloride;
dimethylsilylene(2-butyl-7-chloro-3-phenyl-1-indenyl)(2,3,4,5-tetramethyl-1-cyclopentadienyl)zirconium dichloride;
dimethylsilylene(7-chloro-3-phenyl-2-propyl-1-indenyl)(2,3,4,5-tetramethyl-1-cyclopentadienyl)zirconium dichloride;
dimethylsilylene(7-chloro-2-ethyl-3-phenyl-1-indenyl)(2,3,4,5-tetramethyl-1-cyclopentadienyl)zirconium dichloride;
dimethylsilylene(5-fluoro-3-phenyl-1-indenyl)(2,3,4,5-tetramethyl-1-cyclopentadienyl)zirconium dichloride;
dimethylsilylene(5,7-difluoro-3-phenyl-1-indenyl)(2,3,4,5-tetramethyl-1-cyclopentadienyl)zirconium dichloride;
dimethylsilylene(4,6-difluoro-3-phenyl-1-indenyl)(2,3,4,5-tetramethyl-1-cyclopentadienyl)zirconium dichloride;
dimethylsilylene(5,7-difluoro-2-methyl-3-phenyl-1-indenyl)(2,3,4,5-tetramethyl-1-cyclopentadienyl)zirconium dichloride;
dimethylsilylene(3-phenyl-1,5,6,7-tetrahydro-s-1-indacenyl)(2,3,4,5-tetramethyl-1-cyclopentadienyl)zirconium dichloride;
dimethylsilylene(2-methyl-3-phenyl-1,5,6,7-tetrahydro-s-1-indacenyl)(2,3,4,5-tetramethyl-1-cyclopentadienyl)zirconium dichloride;
dimethylsilylene(6,6-dimethyl-3-phenyl-1,5,6,7-tetrahydro-s-1-indacenyl)(2,3,4,5-tetramethyl-1-cyclopentadienyl)zirconium dichloride;
dimethylsilylene(3-phenyl-2,6,6-trimethyl-1,5,6,7-tetrahydro-s-1-indacenyl)(2,3,4,5-tetramethyl-1-cyclopentadienyl)zirconium dichloride;
dimethylsilylene(3-pheny-5,5,8,8-tetramethyl-5,6,7,8-tetrahydrobenz[f]-1-indenyl)(2,3,4,5-tetramethyl-1-cyclopentadienyl)zirconium dichloride;
dimethylsilylene(3-phenylbenz[f]-1-indenyl)(2,3,4,5-tetramethyl-1-cyclopentadienyl)zirconium dichloride;
dimethylsilylene(2-methyl-3-phenylbenz[f]-1-indenyl)(2,3,4,5-tetramethyl-1-cyclopentadienyl)zirconium dichloride;
dimethylsilylene(2,5,5,8,8-pentamethyl-3-phenyl-5,6,7,8-tetrahydrobenz[f]-1-indenyl)(2,3,4,5-tetramethyl-1-cyclopentadienyl)zirconium dichloride;
dimethylsilylene(3-phenylbenz[e]-1-indenyl)(2,3,4,5-tetramethyl-1-cyclopentadienyl)zirconium dichloride;
dimethylsilylene(2-methyl-3-phenylbenz[e]-1-indenyl)(2,3,4,5-tetramethyl-1-cyclopentadienyl)zirconium dichloride;
dimethylsilylene(3-(4-methylphenyl)-1-indenyl)(2,3,4,5-tetramethyl-1-cyclopentadienyl)zirconium dichloride;
dimethylsilylene(3-(3,5-dimethylphenyl)-1-indenyl)(2,3,4,5-tetramethyl-1-cyclopentadienyl)zirconium dichloride;
dimethylsilylene(3-(2,6-dimethylphenyl)-1-indenyl)(2,3,4,5-tetramethyl-1-cyclopentadienyl)zirconium dichloride;
dimethylsilylene(3-(2,4-dimethylphenyl)-1-indenyl)(2,3,4,5-tetramethyl-1-cyclopentadienyl)zirconium dichloride;
dimethylsilylene(3-(3,4-dimethylphenyl)-1-indenyl)(2,3,4,5-tetramethyl-1-cyclopentadienyl)zirconium dichloride;
dimethylsilylene(3-(2,3-dimethylphenyl)-1-indenyl)(2,3,4,5-tetramethyl-1-cyclopentadienyl)zirconium dichloride;
dimethylsilylene(3-(2,5-dimethylphenyl)-1-indenyl)(2,3,4,5-tetramethyl-1-cyclopentadienyl)zirconium dichloride;
dimethylsilylene(3-(2,4,6-trimethylphenyl)-1-indenyl)(2,3,4,5-tetramethyl-1-cyclopentadienyl)zirconium dichloride;
dimethylsilylene(3-(2,3,4-trimethylphenyl)-1-indenyl)(2,3,4,5-tetramethyl-1-cyclopentadienyl)zirconium dichloride;
dimethylsilylene(3-(3,4,5-trimethylphenyl)-1-indenyl)(2,3,4,5-tetramethyl-1-cyclopentadienyl)zirconium dichloride;
dimethylsilylene(3-(2,3,5-trimethylphenyl)-1-indenyl)(2,3,4,5-tetramethyl-1-cyclopentadienyl)zirconium dichloride;
dimethylsilylene(3-(2,3,6-trimethylphenyl)-1-indenyl)(2,3,4,5-tetramethyl-1-cyclopentadienyl)zirconium dichloride;
dimethylsilylene(3-(2,4,5-trimethylphenyl)-1-indenyl)(2,3,4,5-tetramethyl-1-cyclopentadienyl)zirconium dichloride;
dimethylsilylene(3-(2,3,4,5-tetramethylphenyl)-1-indenyl)(2,3,4,5-tetramethyl-1-cyclopentadienyl)zirconium dichloride;
dimethylsilylene(3-(2,3,4,5-tetramethylphenyl)-1-indenyl)(2,3,4,5-tetramethyl-1-cyclopentadienyl)zirconium dichloride;
dimethylsilylene(3-(2,3,4,6-tetramethylphenyl)-1-indenyl)(2,3,4,5-tetramethyl-1-cyclopentadienyl)zirconium dichloride;
dimethylsilylene(3-(2,3,5,6-tetramethylphenyl)-1-indenyl)(2,3,4,5-tetramethyl-1-cyclopentadienyl)zirconium dichloride;
dimethylsilylene(3-(2,3,4,5,6-pentamethylphenyl)-1-indenyl)(2,3,4,5-tetramethyl-1-cyclopentadienyl)zirconium dichloride;
dimethylsilylene(3-(2-methylphenyl)-1-indenyl)(2,3,4,5-tetramethyl-1-cyclopentadienyl)zirconium dichloride;

dimethylsilylene(3-(2-ethylphenyl)-1-indenyl)(2,3,4,5-tetramethyl-1-cyclopentadienyl)zirconium dichloride;
dimethylsilylene(3-(2-propylphenyl)-1-indenyl)(2,3,4,5-tetramethyl-1-cyclopentadienyl)zirconium dichloride;
dimethylsilylene(3-(2-butylphenyl)-1-indenyl)(2,3,4,5-tetramethyl-1-cyclopentadienyl)zirconium dichloride;
dimethylsilylene(3-(3-methylphenyl)-1-indenyl)(2,3,4,5-tetramethyl-1-cyclopentadienyl)zirconium dichloride;
dimethylsilylene(3-(3-ethylphenyl)-1-indenyl)(2,3,4,5-tetramethyl-1-cyclopentadienyl)zirconium dichloride;
dimethylsilylene(3-(3-propylphenyl)-1-indenyl)(2,3,4,5-tetramethyl-1-cyclopentadienyl)zirconium dichloride;
dimethylsilylene(3-(3-butylphenyl)-1-indenyl)(2,3,4,5-tetramethyl-1-cyclopentadienyl)zirconium dichloride;
dimethylsilylene(3-(3-t-butylphenyl)-1-indenyl)(2,3,4,5-tetramethyl-1-cyclopentadienyl)zirconium dichloride;
dimethylsilylene(3-(4-methylphenyl)-1-indenyl)(2,3,4,5-tetramethyl-1-cyclopentadienyl)zirconium dichloride;
dimethylsilylene(3-(4-ethylphenyl)-1-indenyl)(2,3,4,5-tetramethyl-1-cyclopentadienyl)zirconium dichloride;
dimethylsilylene(3-(4-propylphenyl)-1-indenyl)(2,3,4,5-tetramethyl-1-cyclopentadienyl)zirconium dichloride;
dimethylsilylene(3-(4-butylphenyl)-1-indenyl)(2,3,4,5-tetramethyl-1-cyclopentadienyl)zirconium dichloride;
dimethylsilylene(3-(4-t-butylphenyl)-1-indenyl)(2,3,4,5-tetramethyl-1-cyclopentadienyl)zirconium dichloride;
dimethylsilylene(3-(4-biphenyl)-1-indenyl)(2,3,4,5-tetramethyl-1-cyclopentadienyl)zirconium dichloride;
dimethylsilylene(3-(3-biphenyl)-1-indenyl)(2,3,4,5-tetramethyl-1-cyclopentadienyl)zirconium dichloride;
dimethylsilylene(3-(2-biphenyl)-1-indenyl)(2,3,4,5-tetramethyl-1-cyclopentadienyl)zirconium dichloride;
dimethylsilylene(3-(3,5-diphenylphenyl)-1-indenyl)(2,3,4,5-tetramethyl-1-cyclopentadienyl)zirconium dichloride;
dimethylsilylene(3-(3,5-di-t-butylphenyl)-1-indenyl)(2,3,4,5-tetramethyl-1-cyclopentadienyl)zirconium dichloride;
dimethylsilylene(3-(2-fluorophenyl)-1-indenyl)(2,3,4,5-tetramethyl-1-cyclopentadienyl)zirconium dichloride;
dimethylsilylene(3-(3-fluorophenyl)-1-indenyl)(2,3,4,5-tetramethyl-1-cyclopentadienyl)zirconium dichloride;
dimethylsilylene(3-(4-fluorophenyl)-1-indenyl)(2,3,4,5-tetramethyl-1-cyclopentadienyl)zirconium dichloride;
dimethylsilylene(3-(2,3-difluorophenyl)-1-indenyl)(2,3,4,5-tetramethyl-1-cyclopentadienyl)zirconium dichloride;
dimethylsilylene(3-(2,4-difluorophenyl)-1-indenyl)(2,3,4,5-tetramethyl-1-cyclopentadienyl)zirconium dichloride;
dimethylsilylene(3-(2,5-difluorophenyl)-1-indenyl)(2,3,4,5-tetramethyl-1-cyclopentadienyl)zirconium dichloride;
dimethylsilylene(3-(2,6-difluorophenyl)-1-indenyl)(2,3,4,5-tetramethyl-1-cyclopentadienyl)zirconium dichloride;
dimethylsilylene(3-(3,4-difluorophenyl)-1-indenyl)(2,3,4,5-tetramethyl-1-cyclopentadienyl)zirconium dichloride;
dimethylsilylene(3-(3,5-difluorophenyl)-1-indenyl)(2,3,4,5-tetramethyl-1-cyclopentadienyl)zirconium dichloride;
dimethylsilylene(3-(2,3,4-trifluorophenyl)-1-indenyl)(2,3,4,5-tetramethyl-1-cyclopentadienyl)zirconium dichloride;
dimethylsilylene(3-(2,3,5-trifluorophenyl)-1-indenyl)(2,3,4,5-tetramethyl-1-cyclopentadienyl)zirconium dichloride;
dimethylsilylene(3-(2,3,6-trifluorophenyl)-1-indenyl)(2,3,4,5-tetramethyl-1-cyclopentadienyl)zirconium dichloride;
dimethylsilylene(3-(2,4,5-trifluorophenyl)-1-indenyl)(2,3,4,5-tetramethyl-1-cyclopentadienyl)zirconium dichloride;
dimethylsilylene(3-(2,4,6-trifluorophenyl)-1-indenyl)(2,3,4,5-tetramethyl-1-cyclopentadienyl)zirconium dichloride;
dimethylsilylene(3-(3,4,5-trifluorophenyl)-1-indenyl)(2,3,4,5-tetramethyl-1-cyclopentadienyl)zirconium dichloride;
dimethylsilylene(3-(2,3,4,5-tetrafluorophenyl)-1-indenyl)(2,3,4,5-tetramethyl-1-cyclopentadienyl)zirconium dichloride;
dimethylsilylene(3-(2,3,4,6-tetrafluorophenyl)-1-indenyl)(2,3,4,5-tetramethyl-1-cyclopentadienyl)zirconium dichloride;
dimethylsilylene(3-(2,3,5,6-tetrafluorophenyl)-1-indenyl)(2,3,4,5-tetramethyl-1-cyclopentadienyl)zirconium dichloride;
dimethylsilylene(3-(pentafluorophenyl)-1-indenyl)(2,3,4,5-tetramethyl-1-cyclopentadienyl)zirconium dichloride;
dimethylsilylene(3-(2-chlorophenyl)-1-indenyl)(2,3,4,5-tetramethyl-1-cyclopentadienyl)zirconium dichloride;
dimethylsilylene(3-(3-chlorophenyl)-1-indenyl)(2,3,4,5-tetramethyl-1-cyclopentadienyl)zirconium dichloride;
dimethylsilylene(3-(4-chlorophenyl)-1-indenyl)(2,3,4,5-tetramethyl-1-cyclopentadienyl)zirconium dichloride;
dimethylsilylene(3-(2,6-dichlorophenyl)-1-indenyl)(2,3,4,5-tetramethyl-1-cyclopentadienyl)zirconium dichloride;
dimethylsilylene(3-(3,5-dichlorophenyl)-1-indenyl)(2,3,4,5-tetramethyl-1-cyclopentadienyl)zirconium dichloride;
dimethylsilylene(3-(2,4,6-trichlorophenyl)-1-indenyl)(2,3,4,5-tetramethyl-1-cyclopentadienyl)zirconium dichloride;
dimethylsilylene(3-(2-trifluoromethylphenyl)-1-indenyl)(2,3,4,5-tetramethyl-1-cyclopentadienyl)zirconium dichloride;
dimethylsilylene(3-(3-trifluoromethylphenyl)-1-indenyl)(2,3,4,5-tetramethyl-1-cyclopentadienyl)zirconium dichloride;
dimethylsilylene(3-(4-trifluoromethylphenyl)-1-indenyl)(2,3,4,5-tetramethyl-1-cyclopentadienyl)zirconium dichloride;
dimethylsilylene(3-(3,5-bis(trifluoromethy)lphenyl)-1-indenyl)(2,3,4,5-tetramethyl-1-cyclopentadienyl)zirconium dichloride;
dimethylsilylene(3-(2-methoxyphenyl)-1-indenyl)(2,3,4,5-tetramethyl-1-cyclopentadienyl)zirconium dichloride;
dimethylsilylene(3-(3-methoxyphenyl)-1-indenyl)(2,3,4,5-tetramethyl-1-cyclopentadienyl)zirconium dichloride;
dimethylsilylene(3-(4-methoxyphenyl)-1-indenyl)(2,3,4,5-tetramethyl-1-cyclopentadienyl)zirconium dichloride;
dimethylsilylene(3-(2,6-dimethoxyphenyl)-1-indenyl)(2,3,4,5-tetramethyl-1-cyclopentadienyl)zirconium dichloride;

dimethylsilylene(3-(3,5-dimethoxyphenyl)-1-indenyl)(2,3,4,5-tetramethyl-1-cyclopentadienyl)zirconium dichloride;
dimethylsilylene(3-(2,4,6-trimethoxyphenyl)-1-indenyl)(2,3,4,5-tetramethyl-1-cyclopentadienyl)zirconium dichloride;
dimethylsilylene(3-(1-naphthyl)-1-indenyl)(2,3,4,5-tetramethyl-1-cyclopentadienyl)zirconium dichloride;
dimethylsilylene(3-(2-naphthyl)-1-indenyl)(2,3,4,5-tetramethyl-1-cyclopentadienyl)zirconium dichloride;
dimethylsilylene(2-methyl-3-(2-naphthyl)-1-indenyl)(2,3,4,5-tetramethyl-1-cyclopentadienyl)zirconium dichloride;
dimethylsilylene(3-(1-anthryl)-1-indenyl)(2,3,4,5-tetramethyl-1-cyclopentadienyl)zirconium dichloride;
dimethylsilylene(3-(2-anthryl)-1-indenyl)(2,3,4,5-tetramethyl-1-cyclopentadienyl)zirconium dichloride;
dimethylsilylene(3-(9-anthryl)-1-indenyl)(2,3,4,5-tetramethyl-1-cyclopentadienyl)zirconium dichloride;
dimethylsilylene(3-(9-phenanthryl)-1-indenyl)(2,3,4,5-tetramethyl-1-cyclopentadienyl)zirconium dichloride;
dimethylsilylene(3-(2-furanyl)-1-indenyl)(2,3,4,5-tetramethyl-1-cyclopentadienyl)zirconium dichloride;
dimethylsilylene(3-(2-furanyl)-2-methyl-1-indenyl)(2,3,4,5-tetramethyl-1-cyclopentadienyl)zirconium dichloride;
dimethylsilylene(3-(3-furanyl)-1-indenyl)(2,3,4,5-tetramethyl-1-cyclopentadienyl)zirconium dichloride;
dimethylsilylene(3-(3-furanyl)-2-methyl-1-indenyl)(2,3,4,5-tetramethyl-1-cyclopentadienyl)zirconium dichloride;
dimethylsilylene(3-(2-thiophenyl)-1-indenyl)(2,3,4,5-tetramethyl-1-cyclopentadienyl)zirconium dichloride;
dimethylsilylene(2-methyl-3-(2-thiophenyl)-1-indenyl)(2,3,4,5-tetramethyl-1-cyclopentadienyl)zirconium dichloride;
dimethylsilylene(3-(3-thiophenyl)-1-indenyl)(2,3,4,5-tetramethyl-1-cyclopentadienyl)zirconium dichloride;
dimethylsilylene(2-methyl-3-(3-thiophenyl)-1-indenyl)(2,3,4,5-tetramethyl-1-cyclopentadienyl)zirconium dichloride;
dimethylsilylene(3-(2-pyridyl)-1-indenyl)(2,3,4,5-tetramethyl-1-cyclopentadienyl)zirconium dichloride;
dimethylsilylene(2-methyl-3-(2-pyridyl)-1-indenyl)(2,3,4,5-tetramethyl-1-cyclopentadienyl)zirconium dichloride;
dimethylsilylene(3-(3-pyridyl)-1-indenyl)(2,3,4,5-tetramethyl-1-cyclopentadienyl)zirconium dichloride;
dimethylsilylene(2-methyl-3-(3-pyridyl)-1-indenyl)(2,3,4,5-tetramethyl-1-cyclopentadienyl)zirconium dichloride;
titanium and hafnium analogs of the above zirconium dichloride compounds wherein the zirconium transition metal is replaced with titanium or hafnium; and
dimethyl analogs of the above dichloride compounds wherein the chloride groups on the zirconium, hafnium, or titanium transition metal are replaced with methyl groups.

8. The bridged metallocene compound of claim 1, wherein each of $R^1$, $R^2$, $R^3$, $R^4$, and $R^5$, is, independently, hydrogen or a $C_1$ to $C_{20}$ substituted or unsubstituted hydrocarbyl group.

9. The bridged metallocene compound of claim 1, wherein $R^6$ and $R^9$ are the same.

10. The bridged metallocene compound of claim 1, wherein $R^7$ and $R^8$ are the same.

11. The bridged metallocene compound of claim 1, wherein each of $R^6$, $R^7$, $R^8$, and $R^9$ is, independently, a methyl group, an ethyl group, or an n-propyl group.

12. The bridged metallocene compound of claim 1, wherein each $R^a$ and $R^b$ is each independently selected from the group consisting of chlorides, fluorides, methyl, and ethyl groups.

13. A catalyst system comprising:
(i) a bridged metallocene compound represented by the following formula:

wherein:
M is a group 4 metal;
T is a group 14 atom;
D is a substituted or unsubstituted aromatic group;
$R^a$ and $R^b$ are independently, hydrogen, halogen, or a $C_1$ to $C_{20}$ substituted or unsubstituted hydrocarbyl, and $R^a$ and $R^b$ optionally form a cyclic structure including substituted or unsubstituted aromatic, partially saturated, or saturated cyclic or fused ring system;
each $X^1$ and $X^2$ is independently selected from the group consisting of $C_1$ to $C_{20}$ substituted or unsubstituted hydrocarbyl groups, hydrides, amides, amines, alkoxides, sulfides, phosphides, halides, dienes, phosphines, and ethers; and $X^1$ and $X^2$ optionally form a cyclic structure including aromatic, partially saturated, or saturated cyclic or fused ring system;
each of $R^1$, $R^2$, $R^3$, $R^4$, and $R^5$ is, independently, hydrogen, halide, alkoxide or a $C_1$ to $C_{40}$ substituted or unsubstituted hydrocarbyl group, and any of adjacent $R^2$, $R^3$, $R^4$, and/or $R^5$ groups optionally form a fused ring or multicenter fused ring systems, where the rings are substituted or unsubstituted, and are optionally aromatic, partially unsaturated, or unsaturated; and
each of $R^6$, $R^7$, $R^8$, and $R^9$ is, each independently, hydrogen or a methyl, ethyl, propyl, isopropyl, n-butyl, sec-butyl, t-butyl, pentyl, hexyl, heptyl, octyl, decyl, or undecyl group;
further provided that at least two of $R^6$, $R^7$, $R^8$, and $R^9$ are methyl, ethyl, propyl, isopropyl, n-butyl, sec-butyl, t-butyl, pentyl, hexyl, heptyl, octyl, decyl, or undecyl groups; and
(ii) at least one activator.

14. The catalyst system of claim 13, further comprising a support material.

15. The catalyst system of claim 13, wherein the activator is an alumoxane.

16. The catalyst system of claim 15, wherein the activator is an alkyl alumoxane.

17. The catalyst system of claim 13, wherein the activator is a stoichiometric activator.

18. The catalyst system of claim 17, wherein the activator is an ionic stoichiometric activator.

19. The catalyst system of claim 13, wherein M is zirconium or hafnium.

20. The catalyst system of claim 13, wherein D is selected from the group consisting of substituted or unsubstituted phenyl, naphthyl, biphenyl, cyclopropenyl, tropylium, cyclooctatetraenyl, furanyl, pyridinyl, borabenzyl, thiophenyl, azolyl, oxazolyl, and imidazolyl.

21. The catalyst system of claim 13, wherein T of the bridged metallocene compound is silicon or germanium; each $R^a$ and $R^b$ is each independently selected from the group consisting of halides, $C_1$ to $C_{20}$ substituted or unsubstituted hydrocarbyl groups, and cyclic structures where $R^a$ and $R^b$ form a heterocyclopentyl, heterocyclobutyl, or heterocyclohexyl structure with T being the heteroatom; and each $R^1$, $R^2$, $R^3$, $R^4$, and $R^5$, independently, is hydrogen or a $C_1$ to $C_{20}$ substituted or unsubstituted hydrocarbyl group.

22. A catalyst system comprising the bridged metallocene compound of claim 7.

23. The catalyst system of claim 13, wherein $R^6$ and $R^9$ are the same.

24. The catalyst system of claim 13, wherein $R^7$ and $R^8$ are the same.

25. The catalyst system of claim 13, wherein each of $R^6$, $R^7$, $R^8$, and $R^9$ is, independently, a methyl group, an ethyl group, or an n-propyl group.

26. A process to polymerize olefins comprising contacting olefins with the bridged metallocene compound of claim 1.

27. A process to polymerize olefins comprising contacting olefins with the catalyst systems of claim 1.

28. The process of claim 26 or 27, wherein the polymerization is conducted in the gas phase.

29. A supported catalyst compound comprising the bridged metallocene compound of claim 1 and a support.

30. The supported catalyst compound of claim 29, wherein the support comprises silica.

31. The supported catalyst compound of claim 29, wherein the support comprises a zeolite, clay, organoclay, or mixture thereof.

32. The catalyst system of claim 13, wherein the catalyst system is supported.

33. The catalyst system of claim 32, wherein the support comprises silica.

34. The catalyst system of claim 32, wherein the support comprises a zeolite, clay, organoclay, or mixture thereof.

35. The process of claim 26, wherein the bridged metallocene compound is supported.

36. The process of claim 27, wherein the catalyst system is supported.

37. The process of claim 35, wherein the support comprises a zeolite, clay, organoclay, or mixture thereof.

38. The process of claim 36, wherein the support comprises a zeolite, clay, organoclay, or mixture thereof.

* * * * *